United States Patent
Ishida et al.

(10) Patent No.: US 9,643,951 B2
(45) Date of Patent: May 9, 2017

(54) COMPOUND HAVING SOMATOSTATIN RECEPTOR AGONISTIC ACTIVITY AND PHARMACEUTICAL USE THEREOF

(71) Applicant: ONO PHARMACEUTICAL CO., LTD., Osaka (JP)

(72) Inventors: Akiharu Ishida, Osaka (JP); Takeshi Matsushita, Osaka (JP); Tetsuya Sekiguchi, Osaka (JP); Yasuyuki Okabe, Osaka (JP); Tatsuya Komagata, Osaka (JP); Takuya Nishio, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/025,739

(22) PCT Filed: Sep. 29, 2014

(86) PCT No.: PCT/JP2014/075794
§ 371 (c)(1),
(2) Date: Mar. 29, 2016

(87) PCT Pub. No.: WO2015/046482
PCT Pub. Date: Apr. 2, 2015

(65) Prior Publication Data
US 2016/0311794 A1    Oct. 27, 2016

(30) Foreign Application Priority Data

Sep. 30, 2013  (JP) ................................. 2013-205027
Dec. 26, 2013  (JP) ................................. 2013-268902

(51) Int. Cl.
| C07D 401/14 | (2006.01) |
| C07D 498/04 | (2006.01) |
| A61K 31/5383 | (2006.01) |
| A61K 45/06 | (2006.01) |
| A61K 31/4545 | (2006.01) |
| C07D 401/04 | (2006.01) |

(52) U.S. Cl.
CPC ........ *C07D 401/04* (2013.01); *A61K 31/4545* (2013.01); *A61K 31/5383* (2013.01); *A61K 45/06* (2013.01); *C07D 401/14* (2013.01); *C07D 498/04* (2013.01)

(58) Field of Classification Search
None
See application file for complete search history.

(56) References Cited

U.S. PATENT DOCUMENTS

| 2004/0006089 A1 | 1/2004 | Thurieau et al. |
| 2005/0239796 A1 | 10/2005 | Thurieau et al. |
| 2009/0149652 A1 | 6/2009 | Thurieau et al. |
| 2009/0196912 A1 | 8/2009 | Eickhoff et al. |
| 2009/0258853 A1 | 10/2009 | Eastman et al. |
| 2011/0059971 A1 | 3/2011 | Thurieau et al. |
| 2011/0190297 A1 | 8/2011 | McDonald et al. |
| 2015/0232478 A1 | 8/2015 | Ishida et al. |

FOREIGN PATENT DOCUMENTS

| CN | 101258152 A | 9/2008 |
| FR | 2802206 | 6/2001 |
| WO | 01/44191 A1 | 6/2001 |
| WO | 2006/010637 A2 | 2/2006 |
| WO | 2007/004958 A1 | 1/2007 |
| WO | 2008/019967 A2 | 2/2008 |
| WO | 2008/051272 A2 | 5/2008 |

(Continued)

OTHER PUBLICATIONS

Wolkenberg, et al.; "Design, Synthesis, and Evaluation of Novel 3,6-Diaryl-4-Aminoalkoxyquinolines as Selective Agonists of Somatostatin Receptor Subtype 2", Journal of Medicinal Chemistry, Mar. 2011, vol. 54, 8 pages total.

Contour-Galcera, et al.; "3-Thio-1,2,4-Triazoles, Novel Somatostatin SST₂/SST₅ Agonists", Bioorganic & Medicinal Chemistry Letters, May 2005, vol. 15, 5 pages total.

Search Report dated Nov. 18, 2014, issued by the International Searching Authority in counterpart International Application No. PCT/JP2014/075794 (PCT/ISA/210).

Written Opinion dated Nov. 18, 2014, issued by the International Searching Authority in counterpart International Application No. PCT/JP2014/075794 (PCT/ISA/237).

(Continued)

*Primary Examiner* — Kristin Vajda
(74) *Attorney, Agent, or Firm* — Sughrue Mion, PLLC

(57) ABSTRACT

The present invention provides a somatostatin receptor subtype 2 agonist. A disclosed compound represented by the general formula (I):

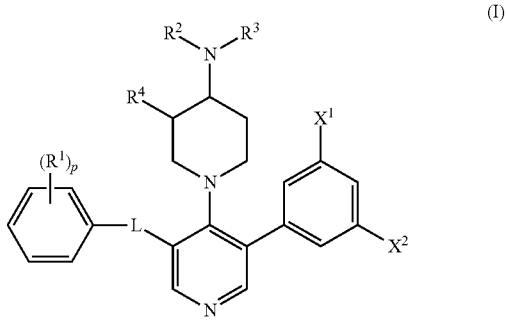

wherein all symbols have the same definitions as described in the specification;
a salt thereof, an N-oxide thereof or a solvate thereof, or a prodrug of the foregoing is a low-molecular compound having strong somatostatin receptor subtype 2 agonistic activity, and thus can be administered in a simple manner, has high stability and has low toxicity. Therefore, the present compound is useful for prophylaxis and/or therapy of somatostatin-related diseases such as acromegaly and gastrointestinal obstruction.

13 Claims, No Drawings

(56) References Cited

FOREIGN PATENT DOCUMENTS

WO     2010/041054 A1     4/2010
WO     2014/007228 A1     1/2014

OTHER PUBLICATIONS

Communication, dated Dec. 20, 2016, issued by the State Intellectual Property Office of P.R. China in counterpart Chinese Patent Application No. 201480053967.4.
Communication, dated Feb. 8, 2017, issued by the European Patent Office in counterpart European Patent Application No. 14847684.9.
Communication, dated Feb. 27, 2017, issued by the Intellectual property Office of Singapore in counterpart Singaporean Patent Application No. 11201602477Y.

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Synthetic oligonucleotide primer hSSTR2_F1_XhoI

```
<400> SEQUENCE: 1
caccctcgag gacatggcgg atgagccact caat                       34

<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide primer
      hSSTR2_R1_EcoRI

<400> SEQUENCE: 2
ccttgaattc gatactggtt tggaggtctc catt                       34
```

COMPOUND HAVING SOMATOSTATIN RECEPTOR AGONISTIC ACTIVITY AND PHARMACEUTICAL USE THEREOF

TECHNICAL FIELD

The present invention relates to a compound represented by the general formula (I) described hereinbelow having a somatostatin receptor, particularly, somatostatin receptor subtype 2 agonistic activity, a salt thereof, an N-oxide thereof or a solvate thereof, or a prodrug of the foregoing, and pharmaceutical use thereof.

BACKGROUND ART

Acromegaly is a hormonal disorder resulting from excess secretion of growth hormones from a pituitary gland caused by pituitary adenoma and the like. The affected patients have hypertrophy of heads, bones in hands and feet and soft tissues. The prevalence of acromegaly is about 60 patients per 1 million people, which is not necessarily high. However, the disease impacts the lives of the patients due to aberrations in parts of the body and is a serious disease having an increased risk of mortality because of cardiac diseases which occur in one-third of the patients.

Patients with acromegaly are currently treated by, in addition to surgical excision of adenoma secreting growth hormone and radiotherapy, drug therapy for exogenously administering an analogue of somatostatin, a hormone which suppresses secretion of growth hormone. Somatostatin analogues include octreotide acetate (Sandostatin®) by Novartis Pharmaceuticals and lanreotide acetate (Somatuline®) by Ipsen Pharma S.A.S., of which usefulness has been recognised and assured. Meanwhile the drugs are peptide drugs and thus require administration by injection, and it is reported that intramuscular injection of the sustained-release formulation thereof once in a few weeks is accompanied by significant pain. In order to solve the problem, it is believed to be the best choice to obtain a non-peptidic, orally administrable low-molecular compound rather than a peptide drug that requires injection.

Meanwhile, it has been revealed that there are 5 somatostatin receptor subtypes, SSTR1 to SSTR5, and it is reported that octreotide acetate and lanreotide acetate bind to somatostatin receptor subtype 2 (SSTR2) with high affinity. It has also been reported that the drugs bind to somatostatin receptor subtype 3 (SSTR3) and somatostatin receptor subtype 5 (SSTR5) with moderate affinity and do not bind to somatostatin receptor subtype 1 (SSTR1) or somatostatin receptor subtype 4 (SSTR4).

As the difference in affinity of octreotide acetate and lanreotide acetate towards the receptor subtypes has been scientifically revealed, a few non-peptidic, low-molecular somatostatin receptor agonists have been synthesised.

For example, PTL 1 discloses that the compound represented by the general formula (A):

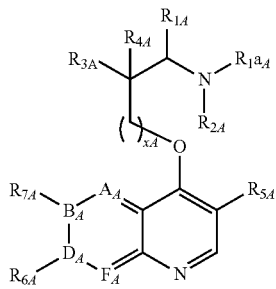

wherein $B_A$ and $D_A$ independently represent a carbon or a nitrogen; $A_A$ and $F_A$ independently represent CH or a nitrogen, provided that only two or less of $A_A$, $B_A$, $D_A$ and $F_A$ are simultaneously nitrogen; $R_{1A}$ and $R_{1aA}$ independently represent a hydrogen, a C1-12 alkyl or the like; $R_{2A}$ represents a hydrogen, a C1-12 alkyl or the like; $R_{3A}$ and $R_{4A}$ independently represent a hydrogen, a halogen, a C1-12 alkyl or the like; $R_{5A}$ represents a $(CH_2)_{mA}$ C6-10 aryl or a $(CH_2)_{mA}$ C5-10 heterocyclyl; $R_{6A}$ represents a hydrogen, a halogen, CN or the like; $R_{7A}$ represents a hydrogen, a halogen, a C1-6 alkyl or the like; mA is an integer of 0 to 6; and xA is an integer of 1 to 3;
and a pharmaceutically acceptable salt, ester, enantiomer, diastereomer or a mixture thereof (the definitions of respective groups are abstracted) is a SSTR2-specific agonist and is useful for treatment of diabetes and related lesions (retinopathy, neuropathy, nephropathy, etc.).

NPL 1 discloses that the compound represented by the following formula (B):

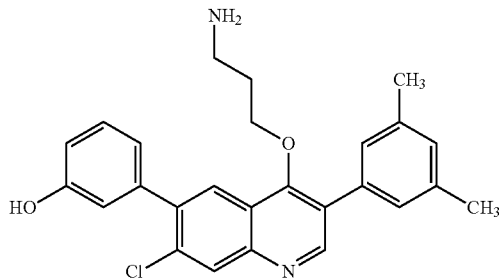

has SSTR2 agonistic activity and suppresses secretion of growth hormone by systemic administration and suppresses ophthalmic angiogenic lesions by local administration.

In addition, PTL 2 discloses that the compound represented by the general formula (C):

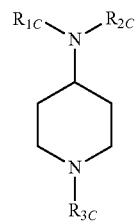

wherein $R_{1C}$ represents a linear or branched (C1-C16) alkyl group, an alkenyl group, an alkynyl group or the like;

$R_{2C}$ represents a group represented by $-C(Y_C)NHX_{1C}$, $-C(O)X_{2C}$ or $-SO_2X_{3C}$; $Y_C$ represents an oxygen atom or a sulphur atom; $R_{3C}$ represents a hydrogen atom, an alkyl group which may be substituted, an alkenyl group, an alkynyl group, an aralkyl group which may be substituted, a heteroarylalkyl group which may be substituted or the like; $X_{1C}$ represents a linear or branched (C1-C15)alkyl group, an alkenyl group, an alkynyl group or the like; $X_{2C}$ represents a linear or branched (C1-C10)alkyl group, an alkenyl group which may be substituted with a phenyl group or the like; $X_{3C}$ represents a linear or branched (C1-C10)alkyl group, an alkenyl group which may be substituted with a phenyl group or the like;

or an addition salt thereof with a pharmaceutically acceptable inorganic or organic acid (the definitions of respective groups are abstracted) shows a preferable affinity towards somatostatin receptors and is particularly useful for treating pathological conditions and illness in which somatostatin receptors are involved.

NPL 2 discloses that the 3-thio-1,2,4-triazole compound represented by the following formula (D):

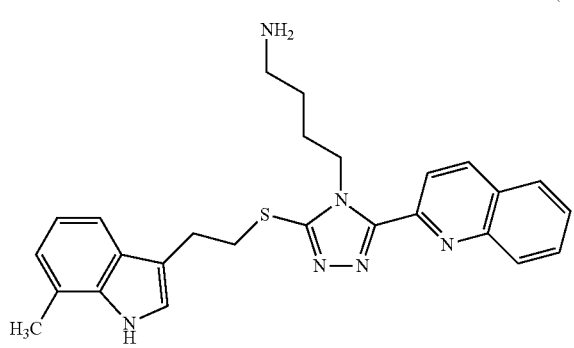

(D)

is an SSTR2 and SSTR5 agonist.

Further, PTL 3 discloses that the compound having a pyridine-piperidine skeleton represented by the following formula (E):

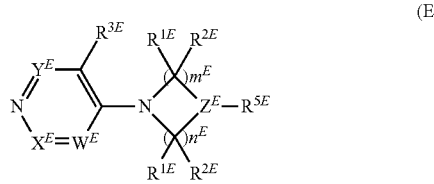

(E)

wherein $W^E$, $X^E$ and $Y^E$ respectively and independently represent CH, $C(R^{4E})$ or N; $Z^E$ represents $C(R^{6E})$ or N; $R^{1E}$ and $R^{2E}$ respectively and independently represents a hydrogen atom or a C1-6 alkyl; $R^{3E}$ and $R^{4E}$ respectively and independently represent a halogen or a group selected from a C1-6 alkyl, a C1-6 alkoxy, a carbocycle and a heterocycle, any of which may be substituted with 1 to 5 $R^{aE}$ groups; when $Z^E$ is $C(R^{6E})$, $R^{5E}$ represents a hydrogen atom, CN, $-N(R^{6E}) R^{7E}$, $-C(O)N(R^{7E}) R^{8E}$ or the like; $R^{6E}$ represents a hydrogen atom, a C1-6 alkyl or the like; $R^{7E}$ and $R^{8E}$ respectively and independently represent a hydrogen atom or a group selected from a C1-6 alkyl which may contain 1 to 3 hetero atoms, a carbocycle and a heterocycle, any of which may be substituted with 1 to 5 $R^{aE}$ groups; each $R^{aE}$ independently represents a halogen, trifluoromethyl, oxo, $-N(R^{bE})R^{cE}$, $R^{dE}$ or the like; $R^{bE}$ and $R^{cE}$ respectively and independently represent a hydrogen or $R^{dE}$; $R^{dE}$ is selected from a hydrocarbon, a carbocycle, a carbocycle-C1-6 alkyl or a heterocycle, any of which may be substituted with 1 to 5 substituents selected from a halogen, cyano, hydroxy and the like; $m^E$ and $n^E$ respectively and independently represent 1 to 3;

is a compound inhibiting Wnt signalling.

However, none of the background art documents disclose the compound described herein, a salt thereof, an N-oxide thereof or a solvate thereof, or a prodrug of the foregoing, or pharmaceutical use thereof, which may not be deduced from any combination of background art documents.

PRIOR ARTS

Patent Literature

[PTL 1] WO 2008/051272
[PTL 2] French Patent Application Publication No. 2802206
[PTL 3] WO 2010/041054

Non Patent Literature

[NPL 1] Journal of Medicinal Chemistry, 2011, Vol. 54, p. 2351-2358
[NPL 2] Bioorganic & Medicinal Chemistry Letters, 2005, Vol. 15, p. 3555-3559

SUMMARY OF INVENTION

Technical Problem

A problem of the present invention is to provide a low-molecular compound which is not a peptide drug requiring injection for administration thereof such as conventional somatostatin receptor agonists and which has somatostatin receptor agonistic activity, particularly SSTR2 agonistic activity, can be administered in a simple manner, has high stability and has low toxicity.

Solution to Problem

The inventors of the present invention have carried out extensive studies in order to achieve the above object, and as a result, found that the compound represented by the general formula (I) described hereinafter, a salt thereof, an N-oxide thereof or a solvate thereof, or a prodrug of the foregoing can achieve the above object. The inventors have carried out further researches and completed the present invention.

Thus specific embodiments disclosed herein encompass, for example, the following:

[A01] a compound represented by the general formula (I):

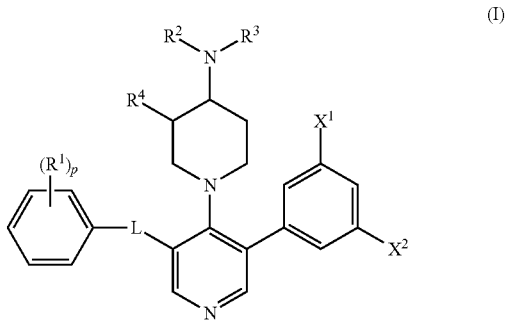

(I)

wherein R¹ represents (1) a halogen atom, (2) a cyano group, (3) a C1-4 alkyl, (4) a C1-4 alkoxy or (5) a C3-8 cycloalkyl, wherein the C1-4 alkyl, the C1-4 alkoxy and the C3-8 cycloalkyl may be respectively and independently substituted with 1 to 3 halogen atoms and/or cyano groups; p represents an integer of 0 to 2; when p is 2, a plurality of R¹ may be the same or different; R² and R³ respectively and independently represent a hydrogen atom or a C1-4 alkyl; R⁴ represents a hydrogen atom; or R² and R⁴ together with an atom to which the R² and R⁴ are bound may form a 5- to 8-membered nitrogen-containing saturated heterocycle; L represents (1) a bond, (2) —CR$^A$═CR$^B$→ or (3) —C(═O)—NR$^D$→(wherein in each group, the arrow indicates the site of binding to the pyridine ring); R$^A$, R$^B$ and R$^D$ respectively and independently represent a hydrogen atom or a C1-4 alkyl; X¹ and X² respectively and independently represent a halogen atom;

a salt thereof, an N-oxide thereof or a solvate thereof, or a prodrug of the foregoing;

[A02] a compound, represented by the general formula (I-1):

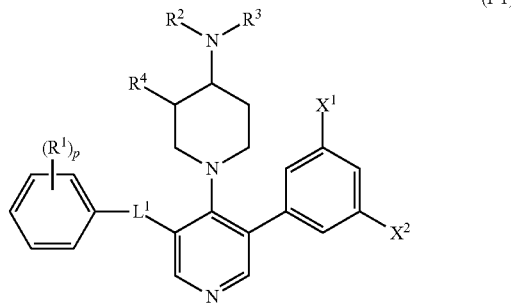

(I-1)

wherein L¹ represents (1) —CR$^A$═CR$^B$→ or (2) —C(═O)—NR$^D$→ (wherein in each group, the arrow indicates the binding site to the pyridine ring); and other symbols have the same meanings as described in [A01], a salt thereof, an N-oxide thereof or a solvate thereof, or a prodrug of the foregoing;

[A03] the compound according to [A02], which is selected from the group consisting of the following compounds:
(1) N-[4-(4-amino-1-piperidinyl)-5-(3-chloro-5-fluorophenyl)-3-pyridinyl]-3-chlorobenzamide;
(2) 1-{3-(3-chloro-5-fluorophenyl)-5-[(E)-2-(3-chlorophenyl)vinyl]-4-pyridinyl}-4-piperidineamine;
(3) 3-{(E)-2-[4-(4-amino-1-piperidinyl)-5-(3,5-dichlorophenyl)-3-pyridinyl]vinyl}benzonitrile;
(4) (4aS,8aS)-6-{3-(3,5-dichlorophenyl)-5-[(E)-2-(3-fluorophenyl)vinyl]-4-pyridinyl}octahydro-1H-pyrido[3,4-b][1,4]oxazine;
(5) 1-{3-(3,5-dichlorophenyl)-5-[(1E)-2-(3-fluorophenyl)-1-propen-1-yl]-4-pyridinyl}-4-piperidineamine;
(6) 3-[(E)-2-{5-(3,5-dichlorophenyl)-4-[4-(ethylamino)-1-piperidin yl]-3-pyridinyl}vinyl]benzonitrile;
(7) 1-{3-(3,5-dichlorophenyl)-5-[(1E)-2-(3-fluorophenyl)-1-propen-1-yl]-4-pyridinyl}-N-ethyl-4-piperidineamine;
(8) 3-{(1E)-1-[4-(4-amino-1-piperidinyl)-5-(3,5-dichlorophenyl)-3-pyridinyl]-1-propen-2-yl}benzonitrile;
(9) 3-[(1E)-1-{5-(3,5-dichlorophenyl)-4-[4-(ethylamino)-1-piperidinyl]-3-pyridinyl}-1-propen-2-yl]benzonitrile; and
(10) N-[4-(4-amino-1-piperidinyl)-5-(3,5-dichlorophenyl)-3-pyridinyl]-5-fluoro-2-methoxybenzamide, a salt thereof, an N-oxide thereof or a solvate thereof, or a prodrug of the foregoing;

[A04] a compound selected from the group consisting of the following compounds:
(1) (3S,4R)-4-amino-1-{3-(3,5-dichlorophenyl)-5-[4-(trifluoromethyl)phenyl]-4-pyridinyl}-3-piperidinol;
(2) rac-(3R,4R)-1-{3-(3,5-dichlorophenyl)-5-[4-(trifluoromethyl)phenyl]-4-pyridinyl}-3-methoxy-4-piperidineamine; and
(3) rac-(3R,4S)-1-{3-(3,5-dichlorophenyl)-5-[4-(trifluoromethyl)phenyl]-4-pyridinyl}-3-methoxy-4-piperidineamine, a salt thereof, an N-oxide thereof or a solvate thereof, or a prodrug of the foregoing;

[A05] a compound which is 1-(4-{5-(3,5-dichlorophenyl)-4-[(4aS,8aS)-octahydro-6H-pyrido[3,4-b][1,4]oxazin-6-yl]-3-pyridinyl}phenyl)cyclopropanecarbonitrile, a salt thereof, an N-oxide thereof or a solvate thereof, or a prodrug of the foregoing;

[A06] a compound represented by the general formula (I-4):

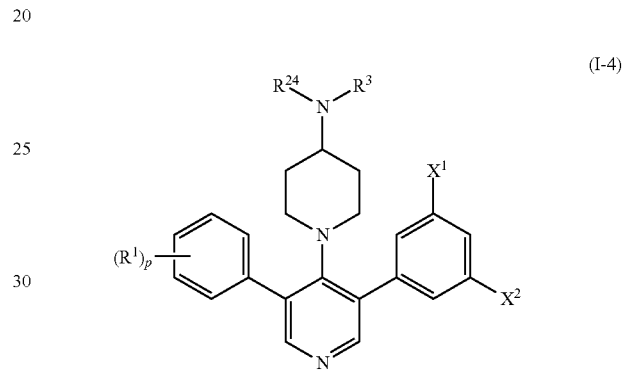

(I-4)

wherein R²⁴ represents a hydrogen atom or a C1-4 alkyl; and other symbols have the same meanings as described in [A01], a salt thereof, an N-oxide thereof or a solvate thereof, or a prodrug of the foregoing;

[A07] the compound according to [A06], which is selected from the group consisting of the following compounds:
(1) 1-{3-(3-chloro-5-fluorophenyl)-5-[4-(trifluoromethyl)phenyl]-4-pyridinyl}-4-piperidineamine;
(2) 1-{3-(3,5-dichlorophenyl)-5-[4-(trifluoromethyl)phenyl]-4-pyridinyl}-4-piperidineamine;
(3) 1-{3-(3-chloro-5-fluorophenyl)-5-[4-(difluoromethoxy)phenyl]-4-pyridinyl}-4-piperidineamine;
(4) 1-{4-[4-(4-amino-1-piperidinyl)-5-(3,5-dichlorophenyl)-3-pyridinyl]phenyl}cyclopropanecarbonitrile;
(5) 1-{3-(3,5-dichlorophenyl)-5-[4-(difluoromethoxy)phenyl]-4-pyridinyl}-4-piperidineamine;
(6) 1-(4-{5-(3,5-dichlorophenyl)-4-[4-(ethylamino)-1-piperidinyl]-3-pyridinyl}phenyl)cyclopropanecarbonitrile;
(7) 2-{4-[4-(4-amino-1-piperidinyl)-5-(3,5-dichlorophenyl)-3-pyridinyl]phenyl}-2-methylpropanenitrile;
(8) 2-(4-{5-(3,5-dichlorophenyl)-4-[4-(ethylamino)-1-piperidinyl]-3-pyridinyl}phenyl)-2-methylpropanenitrile;
(9) 1-{3-(3,5-dichlorophenyl)-5-[4-(trifluoromethyl)phenyl]-4-pyridinyl}-N-ethyl-4-piperidineamine; and
(10) 1-{3-(3,5-dichlorophenyl)-5-[4-(difluoromethoxy)phenyl]-4-pyridinyl}-N-ethyl-4-piperidineamine, a salt thereof, an N-oxide thereof or a solvate thereof, or a prodrug of the foregoing;

[B01] a compound selected from the group consisting of the following compounds:

(1) N-[4-(4-amino-1-piperidinyl)-5-(3-chloro-5-fluorophenyl)-3-pyridinyl]-3-chlorobenzamide;
(2) 1-{3-(3-chloro-5-fluorophenyl)-5-[(E)-2-(3-chlorophenyl)vinyl]-4-pyridinyl}-4-piperidineamine;
(3) 3-{(E)-2-[4-(4-amino-1-piperidinyl)-5-(3,5-dichlorophenyl)-3-pyridinyl]vinyl}benzonitrile;
(4) (4aS,8aS)-6-{3-(3,5-dichlorophenyl)-5-[(E)-2-(3-fluorophenyl)vinyl]-4-pyridinyl}octahydro-1H-pyrido[3,4-b][1,4]oxazine;
(5) 1-{3-(3,5-dichlorophenyl)-5-[(1E)-2-(3-fluorophenyl)-1-propen-1-yl]-4-pyridinyl}-4-piperidineamine;
(6) 3-[(E)-2-{5-(3,5-dichlorophenyl)-4-[4-(ethylamino)-1-piperidin yl]-3-pyridinyl}vinyl]benzonitrile;
(7) 1-{3-(3,5-dichlorophenyl)-5-[(1E)-2-(3-fluorophenyl)-1-propen-1-yl]-4-pyridinyl}-N-ethyl-4-piperidineamine;
(8) 3-{(1E)-1-[4-(4-amino-1-piperidinyl)-5-(3,5-dichlorophenyl)-3-pyridinyl]-1-propen-2-yl}benzonitrile;
(9) 3-[(1E)-1-{5-(3,5-dichlorophenyl)-4-[4-(ethylamino)-1-piperidinyl]-3-pyridinyl}-1-propen-2-yl]benzonitrile;
(10) N-[4-(4-amino-1-piperidinyl)-5-(3,5-dichlorophenyl)-3-pyridinyl]-5-fluoro-2-methoxybenzamide;
(11) (3S,4R)-4-amino-1-{3-(3,5-dichlorophenyl)-5-[4-(trifluoromethyl)phenyl]-4-pyridinyl}-3-piperidinol;
(12) 1-(4-{5-(3,5-dichlorophenyl)-4-[(4aS,8aS)-octahydro-6H-pyrido[3,4-b][1,4]oxazin-6-yl]-3-pyridinyl}phenyl)cyclopropanecarbonitrile;
(13) 1-{3-(3-chloro-5-fluorophenyl)-5-[4-(trifluoromethyl)phenyl]-4-pyridinyl}-4-piperidineamine;
(14) 1-{3-(3,5-dichlorophenyl)-5-[4-(trifluoromethyl)phenyl]-4-pyridinyl}-4-piperidineamine;
(15) 1-{3-(3-chloro-5-fluorophenyl)-5-[4-(difluoromethoxy)phenyl]-4-pyridinyl}-4-piperidineamine;
(16) 1-{4-[4-(4-amino-1-piperidinyl)-5-(3,5-dichlorophenyl)-3-pyridinyl]phenyl}cyclopropanecarbonitrile;
(17) 1-{3-(3,5-dichlorophenyl)-5-[4-(difluoromethoxy)phenyl]-4-pyridinyl}-4-piperidineamine;
(18) 1-(4-{5-(3,5-dichlorophenyl)-4-[4-(ethylamino)-1-piperidinyl]-3-pyridinyl}phenyl)cyclopropanecarbonitrile;
(19) 2-{4-[4-(4-amino-1-piperidinyl)-5-(3,5-dichlorophenyl)-3-pyridinyl]phenyl}-2-methylpropanenitrile;
(20) 2-(4-{5-(3,5-dichlorophenyl)-4-[4-(ethylamino)-1-piperidinyl]-3-pyridinyl}phenyl)-2-methylpropanenitrile;
(21) 1-{3-(3,5-dichlorophenyl)-5-[4-(trifluoromethyl)phenyl]-4-pyridinyl}-N-ethyl-4-piperidineamine;
(22) 1-{3-(3,5-dichlorophenyl)-5-[4-(difluoromethoxy)phenyl]-4-pyridinyl}-N-ethyl-4-piperidineamine;
(23) rac-(3R,4R)-1-{3-(3,5-dichlorophenyl)-5-[4-(trifluoromethyl)phenyl]-4-pyridinyl}-3-methoxy-4-piperidineamine; and
(24) rac-(3R,4S)-1-{3-(3,5-dichlorophenyl)-5-[4-(trifluoromethyl)phenyl]-4-pyridinyl}-3-methoxy-4-piperidineamine,
a salt thereof, an N-oxide thereof or a solvate thereof, or a prodrug of the foregoing;
[B02] the compound according to [B01], which is selected from the group consisting of the following compounds:
(1) N-[4-(4-amino-1-piperidinyl)-5-(3-chloro-5-fluorophenyl)-3-pyridinyl]-3-chlorobenzamide;
(2) 3-{(E)-2-[4-(4-amino-1-piperidinyl)-5-(3,5-dichlorophenyl)-3-pyridinyl]vinyl}benzonitrile;
(3) 1-{3-(3,5-dichlorophenyl)-5-[(1E)-2-(3-fluorophenyl)-1-propen-1-yl]-4-pyridinyl}-N-ethyl-4-piperidineamine;
(4) 3-[(1E)-1-{5-(3,5-dichlorophenyl)-4-[4-(ethylamino)-1-piperidinyl]-3-pyridinyl}-1-propen-2-yl]benzonitrile;
(5) N-[4-(4-amino-1-piperidinyl)-5-(3,5-dichlorophenyl)-3-pyridinyl]-5-fluoro-2-methoxybenzamide;
(6) (3S,4R)-4-amino-1-{3-(3,5-dichlorophenyl)-5-[4-(trifluoromethyl)phenyl]-4-pyridinyl}-3-piperidinol;
(7) 1-(4-{5-(3,5-dichlorophenyl)-4-[(4aS,8aS)-octahydro-6H-pyrido[3,4-b][1,4]oxazin-6-yl]-3-pyridinyl}phenyl)cyclopropanecarbonitrile;
(8) 1-{4-[4-(4-amino-1-piperidinyl)-5-(3,5-dichlorophenyl)-3-pyridinyl]phenyl}cyclopropanecarbonitrile; and
(9) 2-{4-[4-(4-amino-1-piperidinyl)-5-(3,5-dichlorophenyl)-3-pyridinyl]phenyl}-2-methylpropanenitrile,
a salt thereof, an N-oxide thereof or a solvate thereof, or a prodrug of the foregoing;
[B03] the compound according to [B01], which is selected from the group consisting of the following compounds:
(1) 1-{3-(3-chloro-5-fluorophenyl)-5-[(E)-2-(3-chlorophenyl)vinyl]-4-pyridinyl}-4-piperidineamine;
(2) (4aS,8aS)-6-{3-(3,5-dichlorophenyl)-5-[(E)-2-(3-fluorophenyl)vinyl]-4-pyridinyl}octahydro-1H-pyrido[3,4-b][1,4]oxazine;
(3) 3-[(E)-2-{5-(3,5-dichlorophenyl)-4-[4-(ethylamino)-1-piperidinyl]-3-pyridinyl}vinyl]benzonitrile;
(4) 1-{3-(3-chloro-5-fluorophenyl)-5-[4-(trifluoromethyl)phenyl]-4-pyridinyl}-4-piperidineamine;
(5) 1-{3-(3-chloro-5-fluorophenyl)-5-[4-(difluoromethoxy)phenyl]-4-pyridinyl}-4-piperidineamine;
(6) 1-{3-(3,5-dichlorophenyl)-5-[4-(difluoromethoxy)phenyl]-4-pyridinyl}-4-piperidineamine;
(7) 1-(4-{5-(3,5-dichlorophenyl)-4-[4-(ethylamino)-1-piperidinyl]-3-pyridinyl}phenyl)cyclopropanecarbonitrile;
(8) 1-{3-(3,5-dichlorophenyl)-5-[4-(trifluoromethyl)phenyl]-4-pyridinyl}-N-ethyl-4-piperidineamine;
(9) 1-{3-(3,5-dichlorophenyl)-5-[4-(difluoromethoxy)phenyl]-4-pyridinyl}-N-ethyl-4-piperidineamine;
(10) rac-(3R,4R)-1-{3-(3,5-dichlorophenyl)-5-[4-(trifluoromethyl)phenyl]-4-pyridinyl}-3-methoxy-4-piperidineamine; and
(11) rac-(3R,4S)-1-{3-(3,5-dichlorophenyl)-5-[4-(trifluoromethyl)phenyl]-4-pyridinyl}-3-methoxy-4-piperidineamine,
a salt thereof, an N-oxide thereof or a solvate thereof, or a prodrug of the foregoing;
[B04] the compound according to [B01], which is selected from the group consisting of the following compounds:
(1) 1-{3-(3,5-dichlorophenyl)-5-[(1E)-2-(3-fluorophenyl)-1-propen-1-yl]-4-pyridinyl}-4-piperidineamine;
(2) 3-{(1E)-1-[4-(4-amino-1-piperidinyl)-5-(3,5-dichlorophenyl)-3-pyridinyl]-1-propen-2-yl}benzonitrile;
(3) 1-{3-(3,5-dichlorophenyl)-5-[4-(trifluoromethyl)phenyl]-4-pyridinyl}-4-piperidineamine; and
(4) 2-(4-{5-(3,5-dichlorophenyl)-4-[4-(ethylamino)-1-piperidinyl]-3-pyridinyl}phenyl)-2-methylpropanenitrile,
a salt thereof, an N-oxide thereof or a solvate thereof, or a prodrug of the foregoing;
[C01] a pharmaceutical composition including a compound represented by the general formula (I), a salt thereof, an N-oxide thereof or a solvate thereof, or a prodrug of the foregoing and a pharmaceutically acceptable carrier;
[C02] the pharmaceutical composition according to [C01], which is a prophylactic and/or therapeutic agent for a somatostatin-related disease;
[C03] the pharmaceutical composition according to [C02], wherein the somatostatin-related disease is acromegaly or a gastrointestinal symptom accompanying gastrointestinal obstruction;
[D01] a medicament including a compound represented by the general formula (I), a salt thereof, an N-oxide thereof or a solvate thereof, or a prodrug of the foregoing in combination with at least one drug selected from the group consisting of pegvisomant, bromocriptine and cabergoline;

[D02] a medicament including a compound represented by the general formula (I), a salt thereof, an N-oxide thereof or a solvate thereof, or a prodrug of the foregoing in combination with at least one drug selected from the group consisting of prochlorperazine, levomepromazine, risperidone, metoclopramide, domperidone, diphenhydramine, chlorpheniramine, dimenhydrinate, promethazine, diprophylline, famotidine, cimetidine, scopolamine, tropisetron, granisetron, ondansetron, azasetron, ramosetron, indisetron, palonosetron, cisapride, mosapride, dexamethasone, betamethasone, prednisolone, aprepitant, olanzapine, quetiapine, perospirone, methylnaltrexone and morphine;

[E01] a compound represented by the general formula (I), a salt thereof, an N-oxide thereof or a solvate thereof, or a prodrug of the foregoing for prophylaxis and/or therapy of a somatostatin-related disease;

[F01] use of a compound represented by the general formula (I), a salt thereof, an N-oxide thereof or a solvate thereof, or a prodrug of the foregoing for producing a prophylactic and/or therapeutic agent for a somatostatin-related disease;

[Z01] a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1-piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing;

[Z02] a pharmaceutical composition including a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1-piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing and a pharmaceutically acceptable carrier;

[Z03] the pharmaceutical composition according to [Z02], which is a prophylactic and/or therapeutic agent for a somatostatin-related disease;

[Z04] the pharmaceutical composition according to [Z03], wherein the somatostatin-related disease is acromegaly or a gastrointestinal symptom accompanying gastrointestinal obstruction;

[Z05] a medicament including a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1-piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing in combination with at least one drug selected from the group consisting of pegvisomant, bromocriptine and cabergoline;

[Z06] a medicament including a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1-piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing in combination with at least one drug selected from the group consisting of prochlorperazine, levomepromazine, risperidone, metoclopramide, domperidone, diphenhydramine, chlorpheniramine, dimenhydrinate, promethazine, diprophylline, famotidine, cimetidine, scopolamine, tropisetron, granisetron, ondansetron, azasetron, ramosetron, indisetron, palonosetron, cisapride, mosapride, dexamethasone, betamethasone, prednisolone, aprepitant, olanzapine, quetiapine, perospirone, methylnaltrexone and morphine;

[Z07] a method for prophylaxis and/or therapy of a somatostatin-related disease, including administering to a mammal an effective amount of a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1-piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing;

[Z08] a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1-piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing for prophylaxis and/or therapy of a somatostatin-related disease; and

[Z09] use of a compound selected from the group consisting of (1) 1-{3-(3,5-dichlorophenyl)-5-[4-(trifluoromethyl)phenyl]-4-pyridinyl}-4-piperidineamine, (2) 1-{3-(3,5-dichlorophenyl)-5-[(1E)-2-(3-fluorophenyl)-1-propen-1-yl]-4-pyridinyl}-4-piperidineamine, (3) 3-{(1E)-1-[4-(4-amino-1- piperidinyl)-5-(3,5-dichlorophenyl)-3-pyridinyl]-1-propen-2-yl}benzonitrile, (4) 3-[(1E)-1-{5-(3,5-dichlorophenyl)-4-[4-(ethylamino)-1-piperidinyl]-3-pyridinyl}-1-propen-2-yl]benzonitrile, (5) (3S,4R)-4-amino-1-{3-(3,5-dichlorophenyl)-5-[4-(trifluoromethyl)phenyl]-4-pyridinyl}-3-piperidinol and (6) 1-{3-(3-chloro-5-fluorophenyl)-5-[4-(trifluoromethyl)phenyl]-4-pyridinyl}-4-piperidineamine, a salt thereof, an N-oxide thereof or a solvate thereof, or a prodrug of the foregoing for producing a prophylactic and/or therapeutic agent for a somatostatin-related disease.

Effects of Invention

The compound represented by the general formula (I), a salt thereof, an N-oxide thereof or a solvate thereof, or a prodrug of the foregoing (hereinafter collectively referred to as the present compound) as disclosed herein is a low-molecular compound having strong agonistic activity particularly for, among somatostatin receptors, somatostatin receptor subtype 2 (SSTR2), and can be administered by oral or transdermal administration. Therefore, the present compound does not require intramuscular injection that is required for administration of existing peptide medicaments typically including octreotide acetate and lanreotide acetate, and can be easily administered and can alleviate pain accompanied by the therapy of patients. The present compound is also characterised by low toxicity thereof, and thus can be safely used for patients with somatostatin-related diseases in need of administration thereof, particularly for patients with acromegaly and gastrointestinal obstruction.

DESCRIPTION OF EMBODIMENTS

Examples of the "halogen atom" as used herein include fluorine, chlorine, bromine and iodine atoms.

The "C1-4 alkyl" as used herein includes methyl, ethyl, propyl, isopropyl, butyl, sec-butyl, tert-butyl and isobutyl groups.

The "C1-4 alkoxy" as used herein includes methoxy, ethoxy, propoxy, isopropoxy, butoxy, sec-butoxy, tert-butoxy and isobutoxy groups.

The "C3-8 cycloalkyl" as used herein includes cyclopropyl, cyclobutyl, cyclopentyl, cyclohexyl, cycloheptyl and cyclooctyl groups.

As used herein, examples of the "5- to 8-membered nitrogen-containing saturated heterocycle" formed by $R^2$ and $R^4$ together with an atom to which they are attached include oxazolidine, morpholine, 1,4-oxazepam, 1,4-oxazocane and the like. When $R^2$ and $R^4$ together with an atom to which they are bound form such a ring, the general formula (I) may be, for example, represented by the general formula (I-Q):

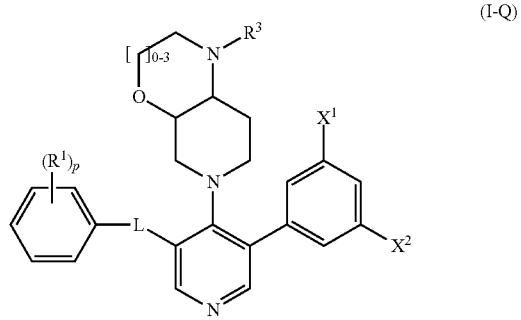

(I-Q)

wherein all symbols have the same meanings as above.

In the present invention, unless particularly stated, the symbol:

indicates that the bond projects below the plane of the paper (i.e. α-configuration), the symbol:

indicates that the bond projects above the plane of the paper (i.e. β-configuration), and the symbol:

indicates that the bond is the α-configuration, the β-configuration or the mixture of these configurations at arbitrary proportions, as apparent to a person skilled in the art.

In the present invention, rings, groups and atoms which represent $R^1$, $R^2$, $R^3$, $R^4$, L, $X^1$ and $X^2$ are all preferred, and the compounds represented by the general formula (I) including combinations of the preferred rings, groups and atoms are more preferred and the compounds described in Examples are particularly preferred. Preferred rings, preferred groups and preferred atoms are described herein. The symbols used herein all have the same meanings as above.

In the present invention, $R^1$ is preferably, for example, a halogen atom, a cyano group, a C1-4 alkyl group substituted with 1 to 3 halogen atoms, a C1-4 alkoxy group which may be substituted with 1 to 3 halogen atoms, a C3-8 cycloalkyl group substituted with a cyano group, a C1-4 alkyl group substituted with a cyano group and the like. Particularly, a halogen atom, a cyano group, a trifluoromethyl group, a difluoromethoxy group, a methoxy group, a 1-cyanocyclopropyl group and a 2-cyanopropan-2-yl group and the like are preferred.

In the present invention, $R^2$ and $R^3$ are preferably a hydrogen atom, a methyl group, an ethyl group and the like. Particularly, a combination of a hydrogen atom and a hydrogen atom and a combination of a hydrogen atom and an ethyl group are preferred.

In the present invention, L is preferably any of a bond, $-CR^A=CR^B-$ and $-C(=O)-NR^D-$. $R^A$, $R^B$ and $R^D$ are preferably, for example, a hydrogen atom, a methyl group and the like. Particularly, L is preferably a bond, $-C(CH_3)=CH-$, $-CH=CH-$ and $-C(=O)-NH-$.

In the present invention, $X^1$ and $X^2$ are preferably, for example, a chlorine atom, a fluorine atom, an iodine atom and the like.

In the present invention, examples of preferred embodiments of the compound represented by the general formula (I) include a compound represented by the general formula (I-1) and a compound represented by the general formula (I-4).

[Isomers]

The present invention encompasses all isomers unless otherwise particularly stated. For example, the alkyl group or alkoxy group includes linear and branched groups. Moreover, the present invention encompasses isomers for double bonds, rings and condensed rings (E-forms, Z-forms, cis forms and trans forms), isomers due to asymmetrical carbon atoms (R and S forms, α and β configurations, enantiomers and diastereomers), optically active substances having optical rotating activity (D, L, d and l forms), polar substances which can be separated by chromatography (high polarity substances and low polarity substances), equilibrium compounds, rotamers, mixtures thereof at arbitrary proportions and racemic mixtures. The present invention also encompasses tautomers.

The designation of a compound as used herein including "rac" is a well-known manner of indication that the compound is racemic substances (see, for example, Pure and Applied Chemistry, 1996, Vol. 68, No. 12, p. 2193-2222 (particularly p. 2216)).

[Salt, N-Oxide and Solvate]

A salt of the compound represented by the general formula (I) disclosed herein encompasses all pharmacologically acceptable salts. The pharmacologically acceptable salt is preferably a water-soluble salt with low toxicity. Examples of appropriate salts include salts of alkali metals (such as potassium, sodium and lithium), salts of alkaline earth metals (such as calcium and magnesium), ammonium salts (such as tetramethylammonium salts and tetrabutylammonium salts), salts of organic amines (such as alkylamines [examples: methylamine, dimethylamine, trimethylamine, triethylamine and the like], heterocyclic amines [examples: pyridine, picoline, piperidine and the like], alkanolamines [examples: monoethanolamine, diethanolamine, triethanolamine and the like], cyclopentylamine, cyclohexylamine, dicyclohexylamine, benzylamine, dibenzylamine, phenethylamine, N,N'-dibenzylethylenediamine, tris(hydroxymethyl)methylamine, N-methyl-D-glucamine, basic natural amino acids [examples: arginine, lysine, ornithine, histidine and the like] and the like), acid addition salts (such as inorganic acid salt [examples: hydrochloride, hydrobromide, hydroiodide, sulphate, phosphate, nitrate and the like], organic acid salts [examples: acetate, trifluoroacetate, lactate, tartrate, oxalate, fumarate, maleate, benzoate, citrate, methanesulphonate, ethanesulphonate, benzenesulphonate, toluenesulphonate, isethionate, glucuronate, gluconate and the like], salts with acidic natural amino acids [examples: aspartate, glutamate and the like] and the like) and the like.

A salt also encompasses quaternary ammonium salts. The quaternary ammonium salt represents a compound represented by the general formula (I) in which a nitrogen atom thereof is quaternised with an $R^0$ group. The $R^0$ group as used herein represents, for example, a C1-8 alkyl group which may be substituted with a phenyl group.

An N-oxide of the compound represented by the general formula (I) represents a compound represented by the general formula (I) in which a nitrogen atom thereof is oxidised. The N-oxide may form salts such as salts of alkali metals, salts of alkaline earth metals, ammonium salts, salts of organic amines and acid addition salts as described above.

The compound represented by the general formula (I), a salt thereof or an N-oxide thereof may form a solvate with, for example, water or an alcoholic solvent (such as ethanol). The solvate preferably has low toxicity and is water soluble.

The compound represented by the general formula (I) can be converted to the salt, N-oxide and solvate according to well-known methods.

[Prodrug]

The prodrug of the compound represented by the general formula (I) refers to a compound which is converted in vivo to the compound represented by the general formula (I) by the reaction with enzymes, gastric acid and the like. Examples of the prodrug of the compound represented by the general formula (I) include, when the compound represented by the general formula (I) has an amino group, compounds in which the amino group is acylated, alkylated or phosphorylated (e.g. compounds represented by the general formula (I) in which the amino group thereof is converted to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl or the like); when the compound represented by the general formula (I) has a hydroxy group, compounds in which the hydroxy group is acylated, alkylated, phosphorylated or converted to borate (e.g. compounds represented by the general formula (I) in which the hydroxy group thereof is converted to acetyl, palmitoyl, propanoyl, pivaloyl, succinyl, fumaryl, alanyl, dimethylaminomethylcarbonyl or the like); when the compound represented by the general formula (I) has a carboxy group, compounds in which the carboxy group is esterified or amidated (e.g. compounds represented by the general formula (I) in which the carboxy group thereof is converted to methyl ester, ethyl ester, isopropyl ester, phenyl ester, carboxymethyl ester, dimethylaminomethyl ester, pivaloyloxymethyl ester, phthalidyl ester, 1-{(ethoxycarbonyl)oxy}ethyl ester, (5-methyl-2-oxo-1,3-dioxolen-4-yl)methyl ester, 1-{[(cyclohexyloxy)carbonyl]oxy}ethyl ester, methylamide or the like) and the like. The prodrug of the compound represented by the general formula (I) may be the one which is converted to the compound represented by the general formula (I) under the physiological condition such as those disclosed in "Iyakuhin no Kaihatsu", vol. 7 "Bunshi Sekkei", p. 163-198, 1990, Hirokawa Shoten Co. The prodrug of the compound represented by the general formula (I) can be produced by the methods well known per se. The prodrug of the compound represented by the general formula (I) may form, similarly to the compound represented by the general formula (I), for example, salts of alkali metals, salts of alkaline earth metals, ammonium salts, salts of organic amines and acid addition salts, or may form solvates with water or an alcoholic solvent (such as ethanol).

[Labelled Compound]

In the present invention, the compound represented by the general formula (I), a salt thereof, an N-oxide thereof or a solvate thereof, or a prodrug of the foregoing encompasses a so-called labelled compound in which some or all atoms constituting the compound is substituted with an isotope thereof. The labelled compound may be produced according to the methods well known per se. Examples of isotopes which may be used for labelling suitably include, but are not limited to, $^2H$, $^3H$, $^{13}C$, $^{14}C$, $^{15}N$, $^{16}N$, $^{17}O$, $^{18}O$, $^{35}S$, $^{36}Cl$, $^{77}Br$, $^{125}I$ and the like.

[Production Method]

The compound represented by the general formula (I), a salt thereof, an N-oxide thereof or a solvate thereof, or a prodrug of the foregoing may be produced by well-known methods, for example, methods described in the following [A1] to [A5], methods equivalent to these methods, methods described in Examples, methods equivalent to those described in Examples, or methods described in Comprehensive Organic Transformations: A Guide to Functional Group Preparations, 2nd Edition (Richard C. Larock, John Wiley & Sons Inc., 1999), methods adapted from the foregoing or methods combining the foregoing without limitation. In the production methods described hereinbelow, raw material compounds may be those forming salts. Examples of the salts include those mentioned above as salts of the compound represented by the general formula (I).

[A1]

Among the present compounds represented by the general formula (I), the compound wherein L represents —C(=O)—NR$^D$→ (wherein in the group, R$^D$ represents a hydrogen atom or a C1-4 alkyl and the arrow indicates the binding site to the pyridine ring), namely the compound represented by the general formula (I-P1):

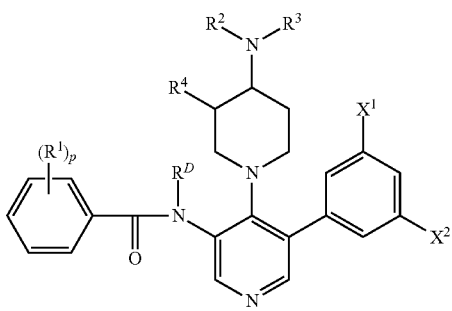

(I-P1)

wherein all symbols have the same meanings as above; can be produced by subjecting a compound represented by the general formula (I-P2):

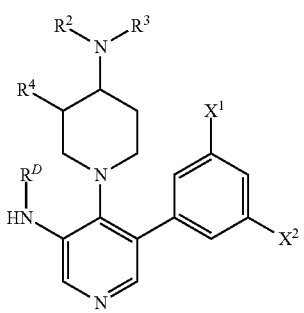

(I-P2)

wherein all symbols have the same meanings as above; and a compound represented by the general formula (I-P3):

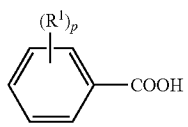

(I-P3)

wherein all symbols have the same meanings as above; to amidation reaction. Upon amidation, a functional group may be optionally protected and/or deprotected.

The amidation reaction is well known. Examples thereof include:
(1) a method using an acid halide;
(2) a method using a mixed acid anhydride;
(3) a method using a condensation agent;
and the like.

These methods are specifically described.

(1) A method using an acid halide may be carried out by, for example, subjecting a carboxylic acid to the reaction with an acid halide forming agent (examples: oxalyl chloride, thionyl chloride and the like) in an organic solvent (examples: chloroform, dichloromethane, diethyl ether, tetrahydrofuran or mixed solvents thereof) or without any solvent at −20° C. to reflux temperature and subjecting the resulting acid halide to the reaction with, in the presence of a base (examples: pyridine, triethylamine, dimethylaniline, dimethylaminopyridine, diisopropylethylamine and the like), an amine in an organic solvent (examples: chloroform, dichloromethane, diethyl ether, tetrahydrofuran or mixed solvents thereof) at a temperature of 0 to 40° C. The method may alternatively be carried out by subjecting the resulting acid halide to the reaction with an amine in an organic solvent (examples: dioxane, tetrahydrofuran or mixed solvents thereof) using an alkali aqueous solution (examples: aqueous sodium bicarbonate or sodium hydroxide solution) at 0 to 40° C.

(2) A method using a mixed acid anhydride may be carried out by, for example, subjecting a carboxylic acid to the reaction with an acid halide (examples: pivaloyl chloride, tosyl chloride, mesyl chloride and the like) or an acid derivative (examples: ethyl chloroformate, isobutyl chloroformate and the like) in an organic solvent (examples: chloroform, dichloromethane, diethyl ether, tetrahydrofuran or mixed solvents thereof) or without any solvent, in the presence of a base (examples: pyridine, triethylamine, dimethylaniline, dimethylaminopyridine, diisopropylethylamine and the like), at 0 to 40° C. and subjecting the resulting mixed acid anhydride to the reaction with an amine in an organic solvent (examples: chloroform, dichloromethane, diethyl ether, tetrahydrofuran or mixed solvents thereof) at 0 to 40° C.

(3) A method using a condensation agent may be carried out by, for example, subjecting a carboxylic acid to the reaction with an amine in an organic solvent (examples: chloroform, dichloromethane, dimethylformamide, diethyl ether, tetrahydrofuran or mixed solvents thereof) or without any solvent, in the presence or absence of a base (examples: pyridine, triethylamine, dimethylaniline, dimethylaminopyridine and the like) using a condensation agent (examples: 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propanephosphonic acid cyclic anhydride (PPA), (benzotriazol-1-yloxy)tris(dimethylamino)phosphonium hexafluorophosphate (BOP), (benzotriazol-1-yloxy)tripyrrolidinophosphonium hexafluorophosphate (pyBOP) and the like) and optionally using 1-hydroxybenzotriazole (HOBt) at 0 to 40° C.

The reactions (1), (2) and (3) are desirably carried out in an inert gas (argon, nitrogen and the like) atmosphere and under an anhydrous condition.

When the present compound represented by the general formula (I-P1) and the raw material compound represented by the general formula (I-P2) or the general formula (I-P3) have a hydroxy group, a carboxy group, an amino group or a mercapto group, the functional group may be appropriately protected before amidation reaction followed by deprotection of the protecting group to produce the present compound, as readily envisaged by a person skilled in the art.

Examples of the protecting group of a hydroxy group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group and the like.

Examples of the protecting group of a carboxy group include a methyl group, an ethyl group, a t-butyl group, an allyl group, a phenacyl group, a benzyl group and the like.

Examples of the protecting group of an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group, 2-nitrobenzenesulphonyl group and the like.

Examples of the protecting group of a mercapto group include a benzyl group, a methoxybenzyl group, a methoxymethyl (MOM) group, a 2-tetrahydropyranyl (THP) group, a diphenylmethyl group, an acetyl (Ac) group and the like.

Protecting groups of a hydroxy group, carboxy group, amino group or mercapto group are not limited to those described above as far as they are readily and selectively detached. Those described in Protective Groups in Organic Synthesis (T. W. Greene, John Wiley & Sons Inc., 1999) may be for example used.

Deprotection reactions of a hydroxy group, carboxy group, amino group or mercapto group are well known and examples thereof include:

(1) deprotection reaction by alkaline hydrolysis;
(2) deprotection reaction under an acidic condition;
(3) deprotection reaction by hydrogenolysis;
(4) deprotection reaction using a metal chelate;
(5) deprotection reaction using a metal;
(6) deprotection reaction of a silyl group;
and the like.

The methods are specifically described.

(1) A deprotection reaction by alkaline hydrolysis (such as deprotection reaction of a trifluoroacetyl group and the like) can be carried out by, for example, in an organic solvent (examples: methanol, tetrahydrofuran, 1, 4-dioxane or mixed solvents thereof), using a hydroxide of an alkali metal (examples: sodium hydroxide, potassium hydroxide, lithium hydroxide and the like), a hydroxide of an alkaline earth metal (examples: barium hydroxide, calcium hydroxide and the like) or a carbonate salt (examples: sodium carbonate, potassium carbonate and the like) or an aqueous solution thereof or a mixture thereof at a temperature of 0 to 40° C.

(2) A deprotection reaction under an acidic condition (such as deprotection reaction of a t-butoxycarbonyl group, a trityl group and the like) can be carried out in, for example, water or an organic solvent (examples: dichloromethane, chloroform, 1,4-dioxane, ethyl acetate, anisole or mixed solvents thereof) and in an organic acid (examples: acetic acid, trifluoroacetic acid, methanesulphonic acid and the like), an inorganic acid (examples: hydrochloric acid, sulphuric acid and the like) or a mixture thereof (examples: hydrogen bromide/acetic acid and the like) at a temperature of 0 to 100° C.

(3) A deprotection reaction by hydrogenolysis (such as deprotection reaction of a benzyl group, a benzhydryl group, a benzyloxycarbonyl group, an allyloxycarbonyl group and the like) can be carried out, for example, in a solvent (examples: ether solvents (examples: tetrahydrofuran, 1,4-dioxane, dimethoxyethane, diethyl ether and the like), alcoholic solvents (examples: methanol, ethanol and the like), benzene solvents (examples: benzene, toluene and the like), ketone solvents (examples: acetone, methyl ethyl ketone and the like), nitrile solvents (examples: acetonitrile and the like), amide solvents (examples: N,N-dimethylformamide and the like), water, ethyl acetate, acetic acid or mixed solvents thereof) in the presence of a catalyst (examples: palladium-carbon, palladium black, palladium hydroxide, platinum oxide, Raney nickel and the like) under normal or increased pressure in a hydrogen atmosphere or in the presence of ammonium formate at a temperature of 0 to 200° C.

(4) A deprotection reaction using a metal chelate (such as deprotection reaction of an allyloxycarbonyl group) can be carried out by, for example, in an organic solvent (examples: dichloromethane, N,N-dimethylformamide, tetrahydrofuran, ethyl acetate, acetonitrile, 1,4-dioxane, ethanol and the like), water or a mixed solvent thereof, in the presence of a trap reagent (examples: tributyltin hydride, triethylsilane, dimedone, morpholine, diethylamine, pyrrolidine and the like), an organic acid (examples: acetic acid, formic acid, 2-ethylhexanoic acid and the like) and/or an organic acid salt (examples: sodium 2-ethylhexanoate, potassium 2-ethylhexanoate and the like), in the presence or absence of a phosphine-based reagent (examples: triphenylphosphine and the like), using a metal chelate (examples: tetrakis (triphenylphosphine)palladium(0), bis(triphenylphosphine) palladium(II) dichloride, palladium(II) acetate, tris(triphenylphosphine)rhodium(I) chloride and the like) at a temperature of 0 to 40° C.

(5) A deprotection reaction using a metal can be carried out by, for example, in an acidic solvent (examples: acetic acid, a buffer of pH 4.2 to 7.2 or a mixed solution of the foregoing with an organic solvent such as tetrahydrofuran) and in the presence of zinc powder, optionally applying ultrasound waves at a temperature of 0 to 40° C.

(6) A deprotection reaction of a silyl group can be carried out by, for example, in a water-miscible organic solvent (examples: tetrahydrofuran, acetonitrile or mixed solvents thereof), using tetrabutylammonium fluoride at a temperature of 0 to 40° C.

A desired present compound may be readily produced by appropriately employing any of the deprotection reactions according to the purpose, as readily envisaged by a person skilled in the art.

If necessary, the reaction may further be followed by a procedure for converting the product to a desired salt according to well-known methods.

[A2]

Among the present compounds represented by the general formula (I), the compound wherein L represents a bond, namely the compound represented by the general formula (I-P4):

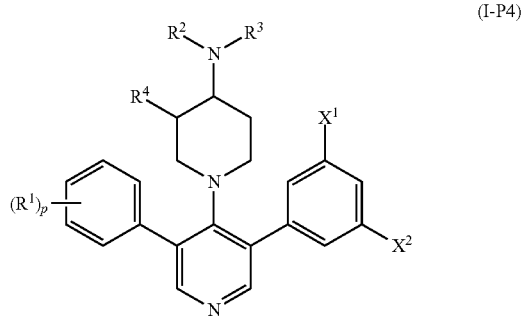

(I-P4)

wherein all symbols have the same meanings as above; can be produced by subjecting a compound represented by the general formula (I-P5):

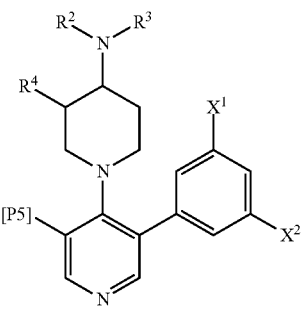

(I-P5)

wherein [P5] represents a leaving group (examples: a halogen atom, mesylate, triflate and the like) and other symbols have the same meanings as above;
to the reaction with a compound represented by the general formula (I-P6):

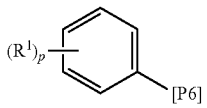

(I-P6)

wherein [P6] represents a boronic acid group (—B(OH)$_2$) or a boronic ester group (—B(ORi) (ORii) (wherein in the group, Ri and Rii respectively and independently represent a C1-3 alkyl or may together form a ring) (e.g. 4,4,5,5-tetramethyl-1,3,2-dioxaborolan-2-yl group and the like) and other symbols have the same meanings as above;
or by subjecting a compound represented by the general formula (I-P7):

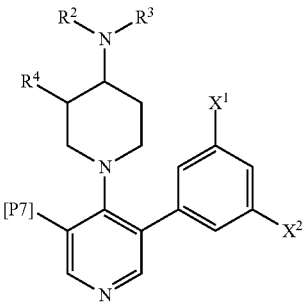

(I-P7)

wherein [P7] represents a boronic acid group (—B(OH)$_2$) or a boronic ester group (—B(ORi) (ORii) (wherein in the group, Ri and Rii respectively and independently represent a C1-3 alkyl or may together form a ring) (e.g. 4,4,5,5-tetramethyl-1,3,2-dioxaborolan-2-yl group and the like) and other symbols have the same meanings as above;
to the reaction with a compound represented by the general formula (I-P8):

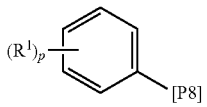

(I-P8)

wherein [P8] represents a leaving group (examples: a halogen atom, mesylate, triflate and the like) and other symbols have the same meanings as above. Upon the reaction, a functional group may be optionally protected and/or deprotected as described above.

The above reaction is well known. For example, the reaction can be carried out in an organic solvent (examples: benzene, toluene, dimethylformamide, dioxane, tetrahydrofuran, methanol, acetonitrile, dimethoxyethane, acetone or mixed solvents thereof), in the presence of a base (examples: sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide, tetrabutylammonium fluoride and the like) or an aqueous solution thereof or a mixture thereof and a catalyst (examples: bis(di-tert-butyl(4-dimethylaminophenyl)phosphine)dichloropalladium(II) ((A-taPhos)$_2$PdCl$_2$), tetrakis(triphenylphosphine)palladium (Pd(PPh$_3$)$_4$), bis(triphenylphosphine)palladium dichloride (PdCl$_2$(PPh$_3$)$_2$), palladium acetate (Pd(OAc)$_2$), palladium black, 1,1'-bis(diphenylphosphinoferrocene)dichloropalladium (PdCl$_2$(dppf)$_2$), diallylpalladium dichloride (PdCl$_2$(allyl)$_2$), phenylbis(triphenylphosphine)palladium iodide (PhPdI(PPh$_3$)$_2$) and the like) at room temperature to 120° C.

Protection and/or deprotection reaction of a functional group may be carried out according to the methods described above.

[A3]

Among the present compounds represented by the general formula (I), the compound wherein L represents —CR$^A$═CR$^B$→ (wherein in the group, R$^A$ and R$^B$ respectively and independently represent a hydrogen atom or a C1-4 alkyl and the arrow indicates the binding site to the pyridine ring), namely the compound represented by the general formula (I-P9):

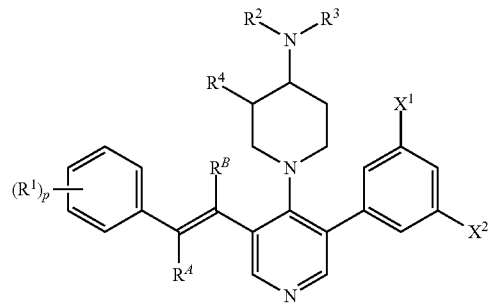

(I-P9)

wherein all symbols have the same meanings as above; can be produced by subjecting a compound represented by the general formula (I-P10):

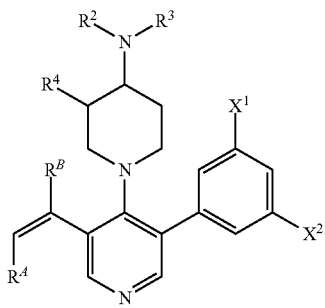

(I-P10)

wherein all symbols have the same meanings as above; to the reaction with a compound represented by the general formula (I-P11):

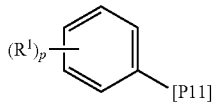

(I-P11)

wherein [P11] represents a halogen atom and other symbols have the same meanings as above;
or by subjecting a compound represented by the general formula (I-P12):

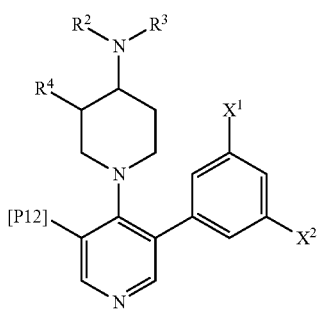

(I-P12)

wherein [P12] represents a halogen atom and other symbols have the same meanings as above;
to a reaction with a compound represented by the general formula (I-P13):

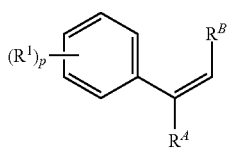

(I-P13)

wherein all symbols have the same meanings as above. Upon the reaction, a functional group may be optionally protected and/or deprotected as described above.

The above reaction is well known. For example, the reaction can be carried out in an organic solvent (examples: dioxane, toluene, dimethylacetamide, dimethylformamide, dimethyl sulphoxide, nitromethane, methanol, ethanol, acetonitrile or mixed solvents thereof) or a mixed solvent of the organic solvent with water, in the presence of abase (examples: dicyclohexylmethylamine, tripotassium phosphate, potassium carbonate, sodium carbonate, silver carbonate, calcium carbonate, sodium hydrogen carbonate, potassium hydrogen carbonate, triethylamine, tributylamine, sodium acetate, cesium carbonate, potassium tert-butoxide, sodium tert-butoxide, lithium hydroxide and the like) or an aqueous solution thereof or a mixture thereof and a catalyst (examples: tetrakis(triphenylphosphine)palladium (Pd (PPh$_3$)$_4$), bis(tri-tert-butylphosphine)palladium(0) (Pd (tBu$_3$P)$_2$), palladium, palladium acetate (Pd(OAc)$_2$), tris (dibenzylideneacetone)dipalladium(0) (Pd(dba)$_2$), dichloro (1,2-bis(diphenylphosphino)ethane)palladium(II) (PdCl$_2$ (dppe)), palladium chloride (PdCl$_2$), diallylpalladium dichloride (PdCl$_2$(allyl)$_2$), copper acetate (Cu(OAc)$_2$), tributylphosphine (PBu$_3$), triphenylphosphine (PPh$_3$), tri-o-tolylphosphine (P(o-tolyl)$_3$) or a mixed catalyst thereof at room temperature to 160° C.

Protection and/or deprotection reaction of a functional group may be carried out according to the methods described above.

[A4]

The compound represented by the general formula (I-P9) can alternatively be produced by subjecting a compound represented by the general formula (I-P14):

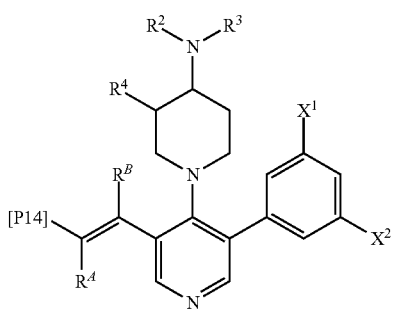

(I-P14)

wherein [P14] represents a boronic acid group (—B(OH)$_2$) or a boronic ester group (—B(ORi)(ORii) (wherein in the group, Ri and Rii respectively and independently represent a C1-3 alkyl or may together form a ring) (e.g. 4,4,5,5-tetramethyl-1,3,2-dioxaborolan-2-yl group and the like) and other symbols have the same meanings as above;
to the reaction with a compound represented by the general formula (I-p15):

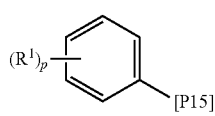

(I-p15)

wherein [P15] represents a leaving group (examples: a halogen atom, mesylate, triflate and the like) and other symbols have the same meanings as above;
or by subjecting a compound represented by the general formula (I-P16):

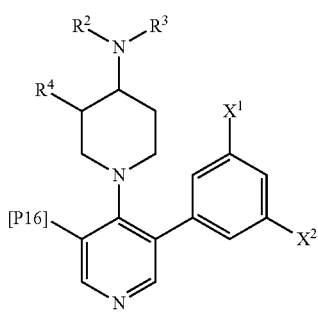

(I-P16)

wherein [P16] represents a leaving group (examples: a halogen atom, mesylate, triflate and the like) and other symbols have the same meanings as above;

to the reaction with a compound represented by the general formula (I-P17):

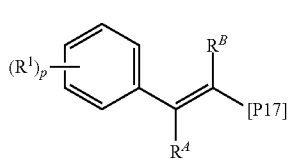

(I-P17)

wherein [P17] represents a boronic acid group (—B(OH)₂) or a boronic ester group (—B(ORi)(ORii) (wherein in the group, Ri and Rii respectively and independently represent a C1-3 alkyl or may together form a ring) (e.g. 4,4,5,5-tetramethyl-1,3,2-dioxaborolan-2-yl group and the like) and other symbols have the same meanings as above. Upon the reaction, a functional group may be optionally protected and/or deprotected as described above.

The above reaction can be carried out by the similar manner as the reaction described in [A2].

Protection and/or deprotection reaction of a functional group may be carried out according to the methods described above.

[A5]

The present compound represented by the general formula (I) can be produced by subjecting a compound represented by the general formula (I-P18):

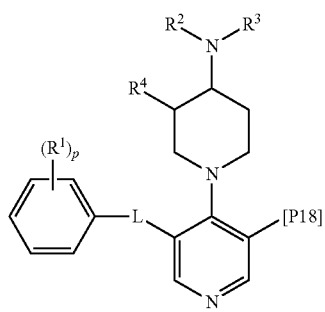

(I-P18)

wherein [P18] represents a leaving group (examples: a halogen atom, mesylate, triflate and the like) and other symbols have the same meanings as above;
to the reaction with a compound represented by the general formula (I-P19):

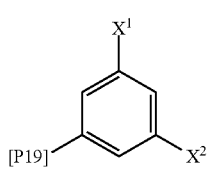

(I-P19)

wherein [P19] represents a boronic acid group (—B(OH)₂) or a boronic ester group (—B(ORi)(ORii) (wherein in the group, Ri and Rii respectively and independently represent a C1-3 alkyl or may together form a ring) (e.g. 4,4,5,5-tetramethyl-1,3,2-dioxaborolan-2-yl group and the like) and other symbols have the same meanings as above;

or by subjecting a compound represented by the general formula (I-P20):

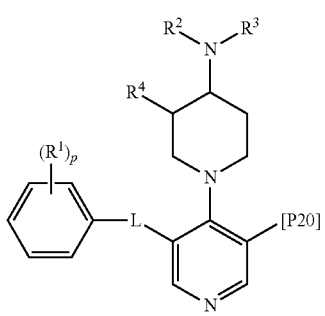

(I-P20)

wherein [P20] represents a boronic acid group (—B(OH)₂) or a boronic ester group (—B(ORi)(ORii) (wherein in the group, Ri and Rii respectively and independently represent a C1-3 alkyl or may together form a ring) (e.g. 4,4,5,5-tetramethyl-1,3,2-dioxaborolan-2-yl group and the like) and other symbols have the same meanings as above;
to the reaction with a compound represented by the general formula (I-P21):

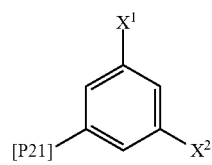

(I-P21)

wherein [P21] represents a leaving group (examples: a halogen atom, mesylate, triflate and the like) and other symbols have the same meanings as above. Upon the reaction, a functional group may be optionally protected and/or deprotected as described above.

The above reaction can be carried out by the similar manner as the reaction described in [A2].

Protection and/or deprotection reaction of a functional group may be carried out according to the methods described above.

Among the present compounds, optically active compounds may be produced with an optically active starting material or reagent, or produced by resolving a racemic intermediate and leading the resolved product to the present compound or by resolving a racemic present compound.

The method for resolution is well known and examples thereof include a method in which a salt or a chelate is formed with a different optically active compound followed by recrystallisation and isolation of a desired compound or a method in which separation is directly carried out with a chiral column and the like.

The starting compounds, i.e. the compounds represented by the general formulae (I-P2), (I-P3), (I-P5), (I-P6), (I-P7), (I-P8), (I-P10), (I-P11), (I-P12), (I-P13), (I-P14), (I-P15), (I-P16), (I-P17), (I-P18), (I-P19), (I-P20) and (I-P21), are well known per se, or can be readily produced by methods well known per se or a combination of methods described in, for example, Comprehensive Organic Transformations: A Guide to Functional Group Preparations, 2nd Edition (Richard C. Larock, John Wiley & Sons Inc., 1999) and the like.

In the reactions exemplified herein, any heating means such as water bath, oil bath, sand bath and microwave may be used.

In the reactions exemplified herein, a solid phase-supported reagent supported on a polymer (such as polystyrene, polyacrylamide, polypropylene and polyethylene glycol) may be used, if appropriate.

The products from the reactions exemplified herein may be purified by a conventional purification means, for example, distillation under normal or reduced pressure, chromatography (such as high performance liquid chromatography, thin layer chromatography or column chromatography) using silica gel, an ion exchange resin, an scavenger resin or magnesium silicate, or by washing or recrystallization. Purification may be carried out after each reaction step or after a series of reactions.

[Toxicity]

The present compound has low toxicity and thus can be safely used as a medicament.

[Application to Medicaments]

The present compound has somatostatin receptor agonistic activity, and thus can be used as an agent for prophylaxis and/or therapy of somatostatin-related diseases (diseases in which somatostatin per se or a hormone modulated by somatostatin is involved) in mammals, particularly in humans.

Examples of such diseases include hormonal diseases (examples: acromegaly, gigantism, pituitary gigantism, Cushing's disease, Graves' disease, hyperthyroidism and the like), ateliosis (examples: skeletal dysplasia, Noonan syndrome, obesity, ateliosis accompanying obesity, uterine hypoplasia, kidney failure accompanying ateliosis, syndrome X and the like), cancer or adenoma (examples: leukaemia, chondrosarcoma, melanoma, lipoma, meningioma, neuroblastoma, pituitary adenoma, headache accompanying pituitary adenoma, growth hormone-secreting adenoma, growth hormone-releasing factor-secreting adenoma, gonadotropin-secreting adenoma, prolactinoma, thyrotropinoma, VIPoma, ACTH-secreting adenoma, thyroid cancer, medullary thyroid cancer, lung cancer, breast cancer, liver cancer, gastrointestinal and pancreatic neuroendocrine adenoma, gastrinoma, carcinoid syndrome, colorectal cancer, pancreatic cancer, islet cell carcinoma, insulin-secreting carcinoma, glucagonoma, prostate cancer, cancerous cachexia, colorectal haemangioma and the like), gastrointestinal diseases (examples: gastrointestinal symptoms accompanying gastrointestinal obstruction, gastroesophageal reflux disease, gastroduodenal reflux disease, excess gastric acid secretion, peptic ulcer, Zollinger-Ellison syndrome, protein-losing gasteroenteropathy, dumping syndrome, short bowel syndrome, inflammatory bowel disease, Crohn's disease, irritable bowel syndrome, irritable colon syndrome, enterocutaneous fistula, functional dyspepsia, nausea, vomiting, bloating and the like), diarrhea (examples: watery diarrhoea syndrome, chronic secondary diarrhoea, chemotherapy-induced diarrhoea, intractable diarrhoea accompanying acquired immune deficiency syndrome, diarrhoea accompanying irritable bowel syndrome, diarrhoea after surgery and the like), vascular diseases (examples: proliferative retinopathy, macular degeneration, age-related macular degeneration, gastrointestinal bleeding, bleeding accompanying gastroduodenal ulcer, bleeding oesophageal varices, bleeding varices of cirrhosis patients, portal hypertension, bleeding vascular graft, restenosis, scarring, psoriasis, systemic sclerosis (scleroderma), chronic rejection of allografts, hypotension, atherosclerosis, post-PTCA restenosis, hypertrophic cardiomyopathy, arteriosclerosis, cardiac valvulopathy, myocardial infarction and the like), fibrosis (examples: skin fibrosis, central nerve system fibrosis, nasal fibrosis, pulmonary fibrosis, hepatic fibrosis, kidney fibrosis, chemotherapy-induced fibrosis and the like), diabetes and diabetic complications (examples: diabetes, insulin-dependent diabetes, diabetic retinopathy, diabetic nephropathy, diabetic neuropathy, dawn phenomenon, insulin resistance, hyperinsulinemia, hyperlipidaemia and the like), inflammatory diseases (examples: arthritis, rheumatoid arthritis, psoriasis, localized inflammation, sunburn, eczema and the like), central nervous system diseases (examples: dementia, Alzheimer's disease, epilepsy and the like), respiratory diseases (examples: sleep apnoea syndrome and the like), pancreatic diseases (examples: pancreatitis, acute pancreatitis, chronic pancreatitis, pancreatic cutaneous fistula, pancreatic pseudocyst, ascites, pancreatic fistula, symptoms related to pancreatic surgery and the like), hepatic diseases (examples: hepatic cyst and the like), renal diseases (examples: hepatorenal syndrome, renal cyst, nephropathy and the like), ovarian diseases (examples: polycystic ovary syndrome and the like), bone and joint diseases (examples: osteoporosis, osteoarthritis and the like), pain, headache and the like. The present compound may also be used for, after introducing a radioactive substance (examples: $^{123}$I, $^{125}$I, $^{111}$In and the like) to the compound directly or via an appropriate spacer, imaging of tumours having somatostatin receptors. The present compound may be used for, after introducing an antitumor drug to the compound directly or via an appropriate spacer, targeting tumours having somatostatin receptors.

Among others, the present compound is useful for prophylaxis and/or therapy of acromegaly, gigantism, pituitary gigantism, pituitary adenoma, headache accompanying pituitary adenoma, growth hormone-secreting adenoma, gastrointestinal and pancreatic neuroendocrine adenoma, gastrinoma, carcinoid syndrome, insulin-secreting carcinoma, glucagonoma, gastrointestinal symptoms accompanying gastrointestinal obstruction, renal cyst, hepatic cyst, bleeding oesophageal varices, portal hypertension, diabetic retinopathy, dementia, Alzheimer's disease, pain and headache. The present compound is particularly suitable for prophylaxis and/or therapy of acromegaly and gastrointestinal symptoms accompanying gastrointestinal obstruction.

Examples of gastrointestinal symptoms accompanying gastrointestinal obstruction as used herein include gastrointestinal symptoms accompanying gastrointestinal obstruction observed in palliative care for patients with advanced and recurrent cancers, which may be alleviated by the present compound.

Examples of test methods other than those described in Examples for evaluating the pharmacological activity of the present compounds include an evaluation system of suppression of gastric acid secretion using rats. For example, suppression of gastric acid secretion by the present compounds may be evaluated by using the following method.

(Evaluation of Suppression of Gastric Acid Secretion Using Rats)

Rats (7-week old male Crl:CD(SD) IGS rats (Charles River Laboratories Japan, Inc.)) are fasted overnight and deprived of water over 2 hours before the evaluation. An indwelling needle is placed in the tail of rats anesthetised with isoflurane. After they awake, rats are continuously and intravenously administered with a medium (saline (Otsuka Normal Saline, Otsuka Pharmaceutical Factory, Inc.)) or a test compound dissolved in the medium through the indwelling needle. One hour after initiation of administration, the abdomens of rats are opened under isoflurane anaesthesia and the gastric pylorus is ligated with a thread. After closing the abdomen, rats are awoken. At 5 hours after initiation of administration (4 hours after pyloric ligation), the abdomen of rats are opened again under isoflurane anaesthesia, the gastric cardia is clamped with forceps and the rats are sacrificed by bleeding. The gastric content is centrifuged at 500×g for 15 minutes, the supernatant is recovered as the gastric juice and the amount of the gastric juice per body weight (mL/100 g-BW) is determined. The acid concentration (mmol/mL) of the gastric juice is determined by back titration using a COM-1600ST automatic titrator (Hitachi High-Technologies Corporation (Hiranuma Sangyo Co., Ltd.)). The product of the amount of the gastric juice and the acid concentration is determined as the amount of gastric acid secretion (mol/100 g-BW), and then the percentage (%) of suppression of gastric acid secretion is determined according to the equation: {[percentage of suppression of gastric acid secretion (%)]=([the amount of gastric acid secretion of the group administered with the medium]−[the amount of gastric acid secretion of the group administered with a test compound])/[the amount of gastric acid secretion of the group administered with the medium]×100}. The inventors of the present invention have found that according to this evaluation system, octreotide, for example, exhibits the percentage of suppression of gastric acid secretion of 39% at the administration rate of 1 mcg (microgram)/kg/h.

Other than the diseases listed above, the present compounds may also be used for prophylaxis and/or therapy of various pathological conditions in which somatostatin is involved, for example, diseases described in Life Sciences, 1987, Vol. 40, p. 419-437; and The European Journal of Medicine, 1993, Vol. 2, p. 97-105.

Upon using the present compound for pharmaceutical purposes, the present compound may be used not only as a single drug but also as a combined drug with an additional active component, for example those listed hereinbelow, for the purposes of, for example, (1) supplementing and/or enhancement of the effect thereof for prophylaxis, therapy and/or amelioration of symptoms, (2) improvement of the kinetics and absorption, reduction of the dosage thereof and/or (3) alleviation of side-effects thereof.

When the present compound is used for prophylaxis and/or therapy of acromegaly, examples of the drugs which may be used with the present compound in combination include somatostatin analogues, growth hormone receptor antagonists, dopamine receptor agonists and the like.

Patients with acromegaly are often associated with diseases related to lifestyle such as diabetes, hypertension, hyperlipidaemia and obesity and various other diseases. Therefore, the present compound may be used in combination with, for example, therapeutic agents for diabetes (examples: insulin-sensitising agents, insulin secretion promoting agents (examples: sulphonylurea and the like), biguanide, insulin, α-glucosidase inhibitors, β3 adrenaline receptor agonists, dipeptidyl peptidase IV inhibitors, amylin agonists, phosphotyrosine phosphatase inhibitors, glycogenesis inhibitors, SGLT (sodium-glucose co-transporter) inhibitors and other therapeutic agents for diabetes), therapeutic agents for diabetic complications (examples: aldose reductase inhibitors, glycation inhibitors, protein kinase C inhibitors, neurotrophic factors, neurotrophic factor increasing agents, nerve regeneration promoting agents and other therapeutic agents for diabetic complications), therapeutic agents for hypertension (examples: angiotensin-converting enzyme inhibitors, calcium antagonists, potassium channel openers, angiotensin II antagonists and the like), therapeutic agents for hyperlipidaemia (examples: HMG-CoA reductase inhibitors, fibrate compounds, squalene synthase inhibitors, antioxidants and the like), anti-obesity agents (examples: pancreatic lipase inhibitors, central acting anti-obesity agents, peptidic appetite suppressants, cholecystokinin agonists and other anti-obesity agents), therapeutic agents for arthritis, anti-anxiety agents, antidepressants, therapeutic agents for osteoporosis, anti-epilepsy drugs, chemotherapeutic agents, immunotherapeutic agents, antithrombotic agents, therapeutic agents for dementia, therapeutic agents for erectile dysfunction, therapeutic agents for urinary incontinent/frequent urination, therapeutic agents for dysuria, nonsteroidal antiinflammatory agents, local anaesthetics, vitamins and the like. The present compound may also be used in combination with hormones which promote secretion of other growth hormones (examples: GHRHs), GH, IGF-1, cytokines and agents for enhancing effects of cytokines.

When the present compound is used for prophylaxis and/or therapy of a gastrointestinal symptom accompanying gastrointestinal obstruction, examples of the drugs which may be used with the present compound in combination include somatostatin analogues, dopamine D2 receptor antagonists, histamine H1 receptor antagonists, concomitant drugs of histamine H1 receptor antagonists and PDE inhibitors, histamine H2 receptor antagonists, anticholinergic agents, serotonin 5HT3 receptor antagonists, serotonin 5HT4 receptor antagonists, corticosteroid, NK1 receptor antagonists, atypical antipsychotics (MARTAs), opioid, opioid antagonists and the like. The present compound may alternatively be used in combination with, for example, prochlorperazine, levomepromazine and the like.

Examples of somatostatin analogues include octreotide, lanreotide, pasireotide and the like.

Examples of growth hormone receptor antagonists include pegvisomant and the like.

Examples of dopamine receptor agonists include bromocriptine, cabergoline and the like.

Examples of insulin-sensitising agents include balaglitazone, netoglitazone, pioglitazone, rivoglitazone, rosiglitazone, farglitazar, muraglitazar, naveglitazar, ragaglitazar, tesaglitazar, reglixane, BM-13.1258, FK-614, KRP-297, LM-4156, LY-510929, MBX-102, MX-6054, R-119702, T-131, THR-0921, compounds disclosed in WO 2001/038325, compounds disclosed in WO 1999/058510 (such as (E)-4-[4-(5-methyl-2-phenyl-4-oxazolylmethoxy)benzyloxyimino]-4-phenylbutyric acid) and the like.

Examples of sulphonylurea include acetohexamide, chlorpropamide, glibenclamide, gliclazide, glimepiride, glipizide, glybuzole, glyclopyramide, mitiglinide, nateglinide, repaglinide, senaglinide, tolazamide, tolbutamide, JTT-608 and the like.

Examples of biguanide include buformin, fenformin, metformin and the like.

Examples of insulin include animal-derived insulin extracted from bovine or porcine pancreas, semi-synthetic human insulin synthesised from insulin extracted from porcine pancreas, human insulin synthesised by genetic engineering manners using *Escherichia coli* or yeasts, insulin-zinc containing 0.45 to 0.9 (w/w) % of zinc, protamine zinc-insulin produced from zinc chloride, protamine sulphate and insulin and the like. Insulin may be a fragment or derivative (examples: INS-1 and the like) thereof and may be an oral insulin formulation. Insulin includes various type such as ultra-rapid-acting, rapid-acting, biphasic, intermediate-acting and long acting insulins, all of which may be used by appropriately selecting the type according to the pathological conditions of patients.

Examples of α-glucosidase inhibitors include acarbose, emiglitate, miglitol, voglibose and the like.

Examples of β3 adrenaline receptor agonists include AJ-9677, AZ40140 and the like.

Examples of dipeptidyl peptidase IV inhibitors include sitagliptin, alogliptin, vildagliptin, linagliptin, anagliptin, saxagliptin, teneligliptin, bisegliptin, carmegliptin, evogliptin, omarigliptin, denagliptin, dutogliptin, gemigliptin, gosogliptin, melogliptin, NVP-DPP-728, PT-100, P32/98, TS-021, TA-6666, KRP-104, DSP-7238, SYR-472 (trelagliptin), TAK-100 and the like.

Examples of amylin agonists include pramlintide and the like.

Examples of phosphotyrosine phosphatase inhibitors include sodium vanadate and the like.

Examples of glycogenesis inhibitors include glycogen phosphorylase inhibitors, glucose-6-phosphatase inhibitors, glucagon antagonists and the like.

Examples of SGLT (sodium-glucose co-transporter) inhibitors include ipragliflozin, luseogliflozin, tofogliflozin, canagliflozin, dapagliflozin and the like.

Examples of therapeutic agents for diabetes other than those mentioned above include bromocriptine, leptin, BAY-27-9955, GLP-1 receptor agonists (examples: GLP-1, GLP-1MR, liraglutide, AC-2993 (exendin-4), BIM-51077, Aib(8, 35)hGLP-1(7,37)NH$_2$, CJC-1131, exenatide and the like), GPR40 agonists (examples: TK-875 and the like), GPR119 agonists, 11β-hydroxysteroid dehydrogenase inhibitors (examples: BVT-3498 and the like), adiponectin or agonists thereof, IKK inhibitors (examples: AS-2868 and the like), leptin-sensitising agents, somatostatin receptor agonists (examples: compounds disclosed in WO 2001/025228, WO 2003/042204, WO 1998/044921, WO 1998/045285, WO 1999/022735 and the like), glucokinase activating agents (examples: RO-28-1675 and the like) and the like.

Examples of aldose reductase inhibitors include tolrestat, epalrestat, imirestat, zenarestat, fidarestat, zopolrestat, minalrestat, ranirestat, CT-112 and the like.

Examples of glycation inhibitors include pimagedine, ALT-946, ALT766, EXO-226 and the like.

Examples of protein kinase C inhibitors include ruboxistaurin mesylate and the like.

Examples of neurotrophic factors include NGF, NT-3, BDNF and the like.

Examples of neurotrophic factor increasing agents include neurotrophin production/secretion-promoting agents disclosed in WO 2001/014372 (examples: 4-(4-chlorophenyl)-2-(2-methyl-1-imidazolyl)-5-[3-(2-methylphenoxy)propyl]oxazole and the like).

Examples of nerve regeneration promoting agents include Y-128, VX-853, prosaptide and the like.

Examples of other therapeutic agents for diabetic complications other than those mentioned above include alprostadil, tiapride, cilostazol, mexiletine, ethyl icosapentate, memantine, pimagedline, AGE inhibitors (examples: ALT-946, alagebrium, pyridorin, pyridoxamine and the like), reactive oxygen eliminating agents (examples: thioctic acid and the like), somatostatin receptor agonists (examples: BIM-23190), apoptosis signal regulating kinase-1 (ASK-1) inhibitors and the like.

Examples of angiotensin-converting enzyme inhibitors include captopril, enalapril, alacepril, delapril, lisinopril, imidapril, benazepril, cilazapril, temocapril, trandolapril and the like.

Examples of calcium antagonists include manidipine, nifedipine, amlodipine, efonidipine, nicardipine and the like.

Examples of potassium channel openers include levcromakalim, AL0671, NIP-121 and the like.

Examples of angiotensin II antagonists include losartan, candesartan cilexetil, eprosartan, valsartan, irbesartan, olmesartan medoxomil, E4177, 1-[[2'-(2,5-dihydro-5-oxo-4H-1,2,4-oxadiazol-3-yl)biphenyl-4-yl]methyl]-2-ethoxy-1H-benzimidazole-7-carboxylic acid and the like.

Examples of HMG-CoA reductase inhibitors include pravastatin, simvastatin, atorvastatin, fluvastatin, pitavastatin, rosuvastatin and the like.

Examples of fibrate compounds include bezafibrate, clinofibrate, clofibrate, simfibrate, fenofibrate and the like.

Examples of squalene synthase inhibitors include compounds disclosed in WO 1997/010224 (examples: N-[[(3R, 5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid and the like) and the like.

Examples of antioxidants include lipoic acid, probucol and the like.

Examples of pancreatic lipase inhibitors include orlistat, cetilistat and the like.

Examples of central-acting anti-obesity agents include mazindol, dexfenfluramine, fluoxetine, sibutramine, fenfluramine, phentermine, amfepramone, dexamfetamine, phenylpropanolamine, clobenzorex and the like.

Examples of peptidic apetite suppressants include leptin, CNTFs (ciliary neurotrophic factors) and the like.

Examples of cholecystokinin agonists include lintitript, FPL-15849 and the like.

Examples of anti-obesity agents other than those mentioned above include lipstatin, MCH receptor antagonists (examples: SB-568849, SNAP-7941, compounds disclosed in WO 2001/082925, compounds disclosed in WO 2001/087834 and the like), neuropeptide Y antagonists (examples: CP-422935 and the like), cannabinoid receptor antagonists (examples: SR-141716, rimonabant and the like), ghrelin antagonists, 11β-hydroxysteroid dehydrogenase inhibitors (examples: BVT-3498 and the like), β3 agonists (examples: AJ-9677, AZ40140 and the like), antifeedants (examples: P-57 and the like) and the like.

Examples of therapeutic agents for arthritis include ibuprofen and the like.

Examples of anti-anxiety agents include chlordiazepoxide, diazepam, oxazolam, medazepam, cloxazolam, bromazepam, lorazepam, alprazolam, fludiazepam and the like.

Examples of antidepressants include fluoxetine, fluvoxamine, imipramine, paroxetine, sertraline and the like.

Examples of therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of anti-epilepsy drugs include gabapentin, trileptal, keppra, zonegran, pregabalin, harkoseride, carbamazepine and the like.

Examples of chemotherapeutic agents include alkylating agents (examples: cyclophosphamide, ifosfamide and the like), anti-metabolites (examples: methotrexate, 5-fluorouracil, 5-fluorouracil derivatives (examples: doxifluridine and the like) and the like), anti-cancer antibiotics (examples: mitomycin, doxorubicin and the like), plant-derived anti-cancer agents (examples: vincristine, vindesine, paclitaxel and the like), cisplatin, carboplatin, etoposide and the like.

Examples of immunotherapeutic agents include components of microorganisms or bacteria (examples: muramyl dipeptide derivatives, picibanil and the like), polysaccharides having immunostimulating activity (examples: lentinan, sizofiran, Krestin® and the like), cytokines obtained by genetic engineering procedures (examples: interferons, interleukins (IL) (examples: IL-1, IL-2, IL-12 and the like) and the like), colony-stimulating factors (examples: granulocyte colony-stimulating factors, erythropoietin (EPO) and the like) and the like.

Examples of antithrombotic agents include heparin (examples: dalteparin, heparin and the like), warfarin (examples: warfarin and the like), antithrombins (examples: argatroban and the like), thrombolytic agents (examples: urokinase, tisokinase, alteplase, nateplase, monteplase, pamiteplase and the like), platelet aggregation inhibitors (examples: ticlopidine, cilostazol, ethyl icosapentate, beraprost, sarpogrelate and the like) and the like.

Examples of therapeutic agents for dementia include donepezil, galanthamine, rivastigmine, tacrine and the like.

Examples of therapeutic agents for erectile dysfunction include apomorphine, sildenafil and the like.

Examples of therapeutic agents for urinary incontinent/frequent urination include flavoxate, imidafenacin, oxybutynin, propiverine and the like.

Examples for therapeutic agents for dysuria include acetylcholine esterase inhibitors (examples: distigmine and the like) and the like.

Examples of nonsteroidal antiinflammatory agents include acetaminophen, aspirin, indomethacin and the like.

Examples of local anaesthetics include capsaicin, lidocaine and the like.

Examples of vitamins include vitamin B1, vitamin B12 and the like.

Examples of dopamine D2 receptor antagonists include prochlorperazine, levomepromazine, risperidone, metoclopramide, domperidone and the like.

Examples of histamine H1 receptor antagonists include diphenhydramine, chlorpheniramine, dimenhydrinate, promethazine and the like.

Examples of concomitant drugs of histamine H1 receptor antagonists with PDE inhibitors include diphenhydramine/diprophylline concomitant drugs and the like.

Examples of histamine H2 receptor antagonists include famotidine, cimetidine and the like.

Examples of anticholinergic agents include scopolamine and the like.

Examples of serotonin 5HT3 receptor antagonists include tropisetron, granisetron, ondansetron, azasetron, ramosetron, indisetron, palonosetron and the like.

Examples of serotonin 5HT4 receptor antagonists include cisapride, mosapride and the like.

Examples of corticosteroid include dexamethasone, betamethasone, prednisolone and the like.

Examples of NK1 receptor antagonists include aprepitant, fosaprepitant and the like.

Examples of atypical antipsychotics (MARTAs) include olanzapine, quetiapine, perospirone and the like.

Examples of opioid include morphine and the like.

Examples of opioid antagonists include methylnaltrexone and the like.

The combined drug of the present compound and an additional drug may be administered in the form of a concomitant drug containing both components in one formulation, or separate formulations may be administered by the same or different routes of administration. It is not necessary that separate formulations are administered simultaneously and separate formulations may be administered sequentially with a time difference. When the formulations are sequentially administered, the order of administration is not particularly limited and may be appropriately adjusted so that desired efficacy of drugs can be obtained.

The dosage of the additional drug which is used in combination with the present compound may be appropriately increased or decreased according to the clinical dosage thereof or a similar drug. The ratio between the present compound and the additional drug may be appropriately adjusted by considering the age and weight of the subject, the administration method, the time of administration, the target disease and condition and the like. Generally, 1 part by weight of the present compound may be combined with 0.01 to 100 parts by weight of the additional drug. A plurality of the additional drug may be used. The additional drug may be, in addition to those mentioned above, a drug having the same mechanism as those mentioned above. Such an additional drug includes not only the one which has been discovered by now but also the one which will be discovered in future.

The dosage of the present compound may vary according to the age, weight, condition, therapeutic effect, administration method, treatment period and the like. The present compound may be orally administered to an adult once to several times daily at the amount of 1 mg to 300 mg per administration, parenterally administered to an adult once to several times daily at the amount of 0.1 mg to 150 mg per administration or intravenously and continuously administered over 1 hour to 24 hours daily.

As described above, the dosage may vary according to various conditions, and thus the amount less than the dosage described above may be sufficient in some cases and the amount exceeding the above dosage may be required in other cases.

When the present compound is used for prophylaxis and/or therapy of the above diseases as a single drug or a combined drug with the additional drug, the present substance which is an active component is generally formulated with a pharmaceutically acceptable carrier such as various additives or solvents and the obtained formulation is administered systemically or locally and orally or parenterally. The pharmaceutically acceptable carrier as used herein means a substance other than an active component that is generally used for medicinal formulations. The pharmaceutically acceptable carrier preferably does not exhibit pharmacological activity, is harmless and does not prevent the therapeutic effect of the active component at the dosage of the formulation. The pharmaceutically acceptable carrier may also be used in order to increase the usefulness of the active component and the formulation, to facilitate production of the formulation, to stabilize the quality or to improve the usability. Specifically, the substances described in "Iyakuhin Tenkabutsu Jiten", 2000, Yakuji Nippo Ltd. (Ed. IPEC Japan) may be appropriately selected according to the need.

Examples of the dosage form include oral administration formulations (examples: tablets, capsules, granules, powders, oral liquids, syrups, oral jelly formulations and the like), oral cavity formulations (examples: tablets for the oral cavity, spray formulations for the oral cavity, semi-solid formulations for the oral cavity, oral rinse and the like), formulations for injection (examples: injections and the like), formulations for dialysis (examples: agents for dialysis and the like), formulations for inhalation (examples: agents for inhalation and the like), ophthalmic formulations (examples: ophthalmic solutions, ophthalmic ointments and the like), otological formulations (examples: ear drops and the like), nasologic formulations (examples: nasal drops and the like), rectal formulations (examples: suppositories, semi-solid formulations for rectal administration, enema formulations and the like), vaginal formulations (examples: vaginal tablets, vaginal suppositories and the like), skin formulations (examples: topical solid formulations, topical liquids, spray formulations, ointments, creams, gels, plasters and pressure sensitive adhesives and the like) and the like.

[Oral Administration Formulations]

Examples of an oral administration formulation include tablets, capsules, granules, powders, oral liquids, syrups, oral jelly formulations and the like. The oral administration formulation may be classified into rapidly disintegrating formulations for which the release of an active component from the formulations is not particularly controlled and release-controlled formulations for which the release is controlled according to the purposes by adjusting the dosage design and production method, such as enteric formulations and sustained release formulations. The enteric formulations refer to a formulation which is designed to release an active component mainly in the small intestine rather than in the stomach with the purpose of prevention of decomposition of the active component in the stomach or reduction of stimulation of the stomach by the active component. The enteric formulation may be generally produced by providing a coating of an acid-insoluble enteric base. The sustained release formulations refer to a formulation for which the release rate, release time and release site of an active component from the formulation is controlled with the purpose of reduction in the frequency of administration or reduction of side effects. The sustained release formulation may be generally produced by using an appropriate agent for sustained release. Among the oral administration formulations, capsules, granules, tablets may be provided with an appropriate coating film of a saccharide, sugar alcohol, polymer compound and the like with the purpose of easy ingestion or prevention of decomposition of an active component.

(1) Tablets

Tablets are an orally administered solid formulation having a certain shape. Examples thereof include those generally referred to as tablets such as plain tablets, film-coated tablets, sugar-coated tablets, multilayered tablets and dry-coated tablets as well as orally disintegrating tablets, chewable tablets, effervescent tablets, dispersible tablets, soluble tablets and the like. Plain tablets may be generally produced according to the following procedure (a), (b) or (c):

(a) An active component is mixed with an additive such as a vehicle, a binding agent and a disintegrating agent to obtain a homogeneous mixture which is granulated by an appropriate method using water or a solution containing a binding agent, mixed with a lubricant and the like, compressed and moulded;

(b) An active component is mixed with an additive such as a vehicle, a binding agent and a disintegrating agent to obtain a homogeneous mixture which is then directly compressed and moulded, or granules prepared with an additive are mixed with an active component, a lubricant and the like to obtain a homogeneous mixture which is then compressed and moulded;

(c) An active component is mixed with an additive such as a vehicle and a binding agent to obtain a homogeneous mixture which is then wetted and kneaded with a solvent, moulded in a certain mould and dried by an appropriate method. Film-coated tablets may be generally produced by providing appropriate thin coating films of a polymer and the like to plain tablets. Sugar-coated tablets may be generally produced by providing coating films containing a saccharide or sugar alcohol to plain tablets. Multilayerd tablets may be produced by stacking layers of powder granules having different compositions and compressing and moulding the product according to an appropriate method. Dry-coated tablets may be produced by coating inner core tablets with outer layers having different compositions. Tablets may be formed as enteric tablets or sustained release tablets according to appropriate well-known methods. Orally disintegrating tablets, chewable tablets, effervescent tablets, dispersible tablets and soluble tablets are the tablets to which unique functions are imparted by appropriately selecting additives, and may be produced according to the production procedures described above for the tablets. Orally disintegrating tablets refer to a tablet ingested by rapid dissolution or disintegration in the oral cavity; chewable tablets refer to a tablet ingested by chewing; effervescent tablets refer to a tablet which is dissolved or dispersed in water with rapid effervescence; dispersible tablets refer to a tablet which is ingested after dispersion in water; and the soluble tablets refer to a tablet which is ingested after dissolution in water. The effervescent tablets may be produced by using an additive which is an appropriate acidic substance, carbonate salt, hydrogen carbonate salt and the like.

(2) Capsules

Capsules are a formulation containing a capsule shell filled with an active component or an active component coated with a capsule base. Examples thereof include hard capsules, soft capsules and the like. Hard capsules may be produced by mixing an active component with an additive such as a vehicle to obtain a homogeneous mixture, or obtaining granules or moulded substance by an appropriate method, which is then directly, or after appropriately being moulded, added to a capsule shell. Soft capsules may be produced by capsulating and moulding a mixture of an active component and an additive into a certain shape with an appropriate capsule base such as gelatine having an increased plasticity by addition of glycerol, D-sorbitol or the like. Capsules may be formed as enteric capsules or sustained release capsules according to appropriate well-known methods. An capsule base may be added with a colorant, a preservative or the like.

(3) Granules

Granules are a granulated formulation. Examples thereof include those generally referred to as granules as well as effervescent granules. Granules may be generally produced according to the following procedure (a), (b) or (c):

(a) A powder active component is mixed with an additive such as a vehicle, a binding agent or a disintegrating agent to obtain a homogeneous mixture which is then granulated by an appropriate method;

(b) A granulated active component is mixed with an additive such as a vehicle to obtain a homogeneous mixture;

(c) A granulated active component is mixed with an additive such as a vehicle to obtain a homogeneous mixture which is then granulated by an appropriate method. Granules may be optionally provided with a film or may be formed as enteric granules or sustained release granules using appropriate well-known methods. Effervescent granules may be produced by using an additive which is an appropriate acidic substance, carbonate salt, hydrogen carbonate salt and the like. The effervescent granules refer to a granule which is dissolved or dispersed in water with rapid effervescence.

The granules may also be formed as fine granules by controlling the particle size.

(4) Powders

Powders are powdery formulations and may be generally produced by mixing an active component with an additive such as a vehicle to obtain a homogeneous mixture.

(5) Oral Liquids

Oral liquids are a formulation in the form of solution or flowable and viscous gel. Examples thereof include those generally referred to as oral liquids as well as elixirs, suspensions, emulsions, lemonades and the like. Oral liquids may be generally produced by mixing an active component with an additive and purified water to homogeneously dissolve, emulsify or suspend the active component and optionally filtering the product. Elixirs refer to a clear oral liquid containing ethanol having sweet taste and aroma. Elixirs may be generally produced by dissolving a solid active component or an infusion thereof in ethanol, purified water, a flavouring agent and sucrose, an additional saccharide or a sweetening agent and obtaining a clear liquid by filtration or other methods. Suspensions refer to an oral liquid in which an active component is finely and homogeneously suspended. Suspensions may be generally produced by suspending a solid active component in a suspending agent or an additional additive and purified water or oil and homogenising the whole product according to an appropriate method. Emulsions refer to an oral liquid in which an active component is finely and homogeneously emulsified. Emulsions may be generally produced by adding an emulsifying agent and purified water to a liquid active component and emulsifying and homogenising the whole product according to an appropriate method. Lemonades refer to a clear oral liquid having sweet taste and sour taste.

(6) Syrups

Syrups are a viscous liquid or solid formulation containing a saccharide or a sweetening agent. Examples thereof include agents for syrups. Syrups may be generally produced by dissolving, mixing, suspending or emulsifying an active component in a solution of sucrose, other saccharides or a sweetening agent or solely a syrup and optionally boiling the product followed by filtering while heating. Formulations for syrups refer to a granular or powdery formulation to which water is added to provide syrups and may be sometimes referred to as dry syrups. Formulations for syrups may be generally produced according to the production procedures described above for the granules or powders by using a saccharide or a sweetening agent as an additive.

(7) Oral Jelly Formulations

Oral jelly formulations are a shaped gel formulation without flowability. Oral jelly formulations may be generally produced by mixing an active component with an additive and a polymer gel base, allowing formation of gel and shaping into a certain shape according to appropriate methods.

[Oral Cavity Formulations]

(1) Tablets for the Oral Cavity

Tablets for the oral cavity are a formulation having a certain shape which is administered to the oral cavity. Examples thereof include troches, sublingual tablets, buccal tablets, adhering tablets, chewing gum tablets and the like. Tablets for the oral cavity may be generally produced according to the production procedures described for the tablets. Troches refer to a tablet for the oral cavity which is gradually dissolved or disintegrated in the oral cavity and is applied locally to the oral cavity or pharynx; sublingual tablets refer to a tablet for the oral cavity to be rapidly dissolved under the tongue to allow absorption of an active component through oral mucosa; buccal tablets refer to a tablet for the oral cavity to be gradually dissolved between the molars and cheeks to allow absorption of an active component through oral mucosa; adhering tablets refer to a tablet for the oral cavity which is adhered to oral mucosa; and chewing gum tablets refer to a tablet for the oral cavity to be chewed to release an active component.

(2) Spray Formulations for the Oral Cavity

Spray formulations for the oral cavity are a formulation to spray an active component in the form of mist, powder, foam or paste. Spray formulations for the oral cavity may be generally produced by dissolving or suspending an active component and an additive in a solvent or the like, optionally filtering thereof and packing the product into a container together with liquefied gas or compressed gas, or by preparing a solution or suspension with an active component and an additive and packing the product into a container to which a spraying pump is attached.

(3) Semi-Solid Formulations for the Oral Cavity

Semi-solid formulations for the oral cavity are a formulation to be applied to the oral mucosa. Examples thereof include creams, gels, ointments and the like. Semi-solid formulations for the oral cavity may be generally produced by emulsifying an active component together with an additive in purified water and an oil component such as petrolatum, or by mixing an active component and an additive with a base such as a polymer gel or an oil or fat and obtaining a homogeneous mixture. Creams refer to a semi-solid formulation in the form of an oil-in-water or water-in-oil emulsion and lipophilic formulations in the form of a water-in-oil emulsion may also be referred to as oil-based creams. Creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion. Gels refer to a gel formulation and examples thereof include water-based gels, oil-based gels and the like. Water-based gels may be produced by dissolving or suspending an active component in an additive such as a polymer compound and purified water and allowing cross-linking by heating and cooling or addition of a gel-forming agent. Oil-based gels may be produced by mixing an active component with a liquid oil base such as a glycol or a higher alcohol and an additive. Ointments refer to a semi-solid formulation containing an active component dissolved or dispersed in a base. Examples thereof include oil- or fat-based ointments, water-soluble ointments and the like. Oil- or fat-based ointments may be generally produced by melting an oil- or fat-based base such as an oil or fat, a wax and a hydrocarbon including paraffin by heating, dissolving or dispersing an active component therein and mixing and kneading to obtain a homogeneous mixture. Water-soluble ointments may be generally produced by melting a water-soluble base such as macrogol by heating and mixing and kneading an active component therein to obtain a homogeneous mixture.

(4) Oral Rinses

Oral rinses are a liquid formulation to be applied locally to the oral cavity or pharynx and may include solid formulations which are dissolved upon use. Oral rinses may be generally produced by homogeneously dissolving an active component in a solvent and an additive and optionally filtering the solution. Solid formulations which are dissolved upon use may be generally produced according to the production procedures described for the tablets and granules.

[Formulations for Injection]

(1) Injections

Injections are an aseptic formulation in the form of solution, suspension or emulsion or solid to be dissolved or suspended upon use, which are directly administered to body tissues and organs such as under the skin, in the muscle or to a vessel. Examples thereof include those generally referred to as injections as well as lyophilised injections, powder injections, pre-filled syringes, cartridges, transfusions, implantable injections, sustained release injections and the like. Injections may be generally produced according to the following procedure (a) or (b):

(a) An active component or a mixture of an active component with an additive is dissolved, suspended or emulsified in water for injection or another aqueous solvent or a non-aqueous solvent and the product is packed into a container for injection which is then sterilised;

(b) An active component or a mixture of an active component with an additive is dissolved, suspended or emulsified in water for injection or another aqueous solvent or a non-aqueous solvent and the product is subjected to aseptic filtration or the product is homogeneously prepared in an aseptic manner and is charged into a container for injection which is then sealed. Lyophilised injections may be generally produced by dissolving an active component or an active component together with an additive such as a vehicle in water for injection, subjecting the solution to aseptic filtration, charging the solution in a container for injection followed by lyophilisation or lyophilising the solution in a container dedicated for lyophilisation followed by packing the product in a container for injection. Powder injections may be generally produced by aseptic filtration and crystallization to obtain powder which is directly or a mixture thereof with a sterilized additive is charged into a container for injection. Pre-filled syringes may be generally produced by charging an active component or a solution, suspension or emulsion of an active component and an additive into a syringe. Cartridges refer to an injection in the form of a cartridge containing a drug solution to be placed in a dedicated syringe. Cartridges containing a drug solution may be generally produced by charging an active component or a solution, suspension or emulsion of an active component and an additive into a cartridge. Transfusions refer to an injection generally of 100 mL of more which is intravenously administered. Implantable injections refer to an injection in the form of a solid or gel, which is to be applied using an implantable tool or by surgery under the skin or in the muscle in order to release an active component over a long period of time. Implantable injections may be generally produced by forming a pellet, microsphere or gel with a biodegradable polymer compound. Sustained release injections refer to an injection applied in the muscle in order to release an active component over a long period of time and may be generally produced by dissolving or suspending an active component in a vegetable oil or obtaining a microsphere suspension with a biodegradable polymer compound.

[Formulations for Dialysis]

(1) Agents for Dialysis

Agents for dialysis are a liquid formulation or a solid formulation dissolved upon use to be used for peritoneal dialysis or haemodialysis. Examples thereof include agents for peritoneal dialysis, agents for haemodialysis and the like. Agents for peritoneal dialysis refer to an aseptic agent for dialysis used for peritoneal dialysis and may be generally produced by charging a solution of an active component and an additive in a solvent at a certain volume or a mixture of an active component and an additive into a container, sealing the same and optionally sterilizing the same. Solid formulations to be dissolved upon use may be generally produced according to the production procedures described above for the tablets and granules. Agents for haemodialysis refer to an agent for dialysis used for haemodialysis and may be generally produced by charging a solution of an active component and an additive in a solvent at a certain volume or a mixture of an active component and an additive into a container. Solid formulations to be dissolved upon use may be generally produced according to the production procedures described above for the tablets and granules.

[Formulations for Inhalation]

(1) Agents for Inhalation

Agents for inhalation are a formulation applied to the bronchus or lung by inhaling aerosols of an active component. Examples thereof include powder agents for inhalation, liquid agents for inhalation, aerosols for inhalation and the like. Powder agents for inhalation refer to a formulation to be inhaled as aerosols of solid particles at a predetermined amount, and may be generally produced by preparing fine particles of an active component and optionally mixing thereof with an additive such as lactose to obtain a homogeneous mixture. Liquid agents for inhalation refer to a liquid agent for inhalation to be applied by a nebuliser and the like and may be generally produced by homogeneously dissolving or suspending an active component in a solvent, an appropriate tonicity agent, a pH-controlling agent and the like and optionally filtering the product. Aerosols for inhalation refer to a metered-dose agent for inhalation to spray a predetermined amount of active component packed in a container together with a propellant. Aerosols for inhalation may be generally produced by preparing a solution or suspension from an active component, a solvent, an appropriate dispersant, a stabilising agent and the like and charging the product in a pressure resistant container attached with a flow regulating valve together with a liquid propellant.

[Ophthalmic Formulations]

(1) Ophthalmic Solutions

Ophthalmic solutions are a liquid aseptic formulation or a solid aseptic formulation to be dissolved or suspended upon use, which is applied to ophthalmic tissue such as conjunctival sac. Ophthalmic solutions may be generally produced by charging a solution or suspension of an active component and an additive in a solvent or the like at a certain volume or a mixture of an active component and an additive in a container.

(2) Ophthalmic Ointments

Ophthalmic ointments are a semi-solid aseptic formulation to be applied to ophthalmic tissue such as conjunctival sac, and may be generally produced by charging a homogeneous mixture of a base such as petrolatum and a solution or fine powder of an active component in a container.

[Otological Formulations]

(1) Ear Drops

Ear drops are a liquid or semi-solid formulation or a solid formulation to be dissolved or suspended upon use, which is administered to the external ear or middle ear. Ear drops are generally produced by charging a solution or suspension of an active component and an additive in a solvent or like at a certain volume or a mixture of an active component and an additive in a container.

[Nasologic Formulations]

(1) Nasal Drops

Nasal drops are a formulation to be administered to the nasal cavity or nasal mucosa and examples thereof include nasal powders, nasal liquids and the like. Nasal powders refer to a fine powder nasal drop to be administered to the nasal cavity and may be generally produced by making appropriately fine powder of an active component and optionally mixing the active component with an additive to obtain a homogeneous mixture. Nasal liquids refer to a nasal drop which is liquid or solid to be dissolved or suspended upon use and is administered to the nasal cavity. Nasal liquids may be generally produced by dissolving or suspending an active component in a solvent and an additive and optionally filtering the product. An additive for nasal liquids which may be used includes a tonicity agent, a pH controlling agent and the like.

[Rectal Formulations]

(1) Suppositories

Suppositories are a semi-solid formulation having a certain shape, which is applied in the rectum and releases an active component by melting at body temperature or gradually dissolving or dispersing in water. Suppositories may be generally produced by dissolving or homogeneously dispersing a homogeneous mixture of an active component with an additive such as a dispersant and an emulsifying agent in a base liquefied by heating and the like, charging a predetermined amount of the product in a container and solidifying/moulding the same. Abase for suppositories which may be generally used includes oil- or fat-based bases and hydrophilic bases.

(2) Semi-Solid Formulations for Rectal Administration

Semi-solid formulations for rectal administration are a formulation applied around or in the anus and examples thereof include rectal creams, rectal gels, rectal ointments and the like. Semi-solid formulations for rectal administration may be generally produced by emulsifying an active component together with an additive in purified water and an oil component such as petrolatum, or by homogeneously mixing an active component and an additive with a base which is a polymer gel or an oil or fat. Rectal creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion. Rectal gels refer to a gel formulation and examples thereof include water-based gels, oil-based gels and the like. Water-based gels may be produced by dissolving or suspending an active component in an additive such as a polymer compound and purified water and allowing crosslinking by heating and cooling or addition of a gel-forming agent. Oil-based gels may be produced by mixing an active component with a liquid oil base such as a glycol or a higher alcohol and an additive. Rectal ointments refer to a semi-solid formulation containing an active component dissolved or suspended in a base and examples thereof include oil- or fat-based ointments, water-soluble ointments and the like. Oil- or fat-based ointments may be generally produced by melting an oil- or fat-based base such as an oil or fat, a wax and a hydrocarbon including paraffin by heating, dissolving or suspending an active component therein and mixing and kneading to obtain a homogeneous mixture. Water-soluble ointments may be generally produced by melting a water-soluble base such as macrogol by heating and mixing and kneading an active component therein to obtain a homogeneous mixture.

(3) Enema Formulations

Enema formulations are a liquid or viscous gel formulation to be applied through the anus. Enema formulations are generally produced by dissolving or suspending an active component in a solvent or the like at a certain volume using purified water or an appropriate aqueous solvent and charging the product in a container. An additive which may be used for enema formulations includes a dispersant, a stabilising agent, a pH controlling agent and the like.

[Vaginal Formulations]

(1) Vaginal Tablets

Vaginal tablets are a solid formulation having a certain shape, which is applied in the vagina and releases an active component by gradually dissolving or dispersing in water. Vaginal tablets may be generally produced according to the production procedures described above for the tablets.

(2) Vaginal Suppositories

Vaginal suppositories are a semi-solid formulation having a certain shape, which is applied in the vagina and releases an active component by melting at body temperature or gradually dissolving or dispersing in water. Vaginal suppositories may be generally produced according to the production procedures described above for the rectal suppositories and the like.

[Skin Formulations]

(1) Topical Solid Formulations

Topical solid formulations are a solid formulation to be applied or spread on skin including the scalp or nails and examples thereof include topical powders. Topical powders refer to a topical solid powder formulation and may be generally produced by mixing an active component with an additive such as a vehicle to obtain a homogeneous mixture which is then formed into powders.

(2) Topical Liquids

Topical liquids are a liquid formulation to be applied on skin including the scalp or nails and examples thereof include liniments, lotions and the like. Topical liquids may be generally produced by dissolving, emulsifying or suspending an active component in a solvent, an additive and the like and optionally filtering the product. Liniments refer to a liquid or muddy topical liquid to be rubbed into the skin. Lotions refer to a topical liquid containing an active component dissolved, emulsified or finely dispersed in an aqueous liquid. Lotions may be generally produced by preparing a solution, suspension or emulsion of an active component, an additive and purified water to obtain a homogeneous product.

(3) Spray Formulations

Spray formulations are a formulation to spray an active component in the form of mist, powder, foam or paste on the skin and examples thereof include topical aerosols, pump spray formulations and the like. Spray formulations may be generally produced by preparing a solution or suspension of an active component, optionally filtering the product and charging the product in a container. Topical aerosols refer to a spray formulation which sprays an active component together with liquefied gas or compressed gas packed in a container. Topical aerosols may be generally produced by preparing a solution or suspension of an active component and packing the product into a pressure resistant container attached with a continuous injection valve together with a liquid propellant. An additive such as a dispersant and a stabilising agent may be optionally added to topical aerosols. Pump spray formulations refer to a spray formulation which sprays an active component in a container by means of a pump. Pump spray formulations may be generally produced by dissolving or suspending an active component and an additive and charging the product in a container to which a pump is attached.

(4) Ointments

Ointments are a semi-solid formulation to be applied on the skin containing an active component dissolved or dispersed in a base. Examples thereof include oil- or fat-based ointments, water soluble ointments and the like. Oil- or fat-based ointments may be generally produced by melting an oil- or fat-based base such as an oil or fat, a wax and a hydrocarbon including paraffin by heating, dissolving or suspending an active component therein and mixing and kneading to obtain a homogeneous mixture. Water soluble ointments may be generally produced by melting a water-soluble base such as macrogol by heating and mixing and kneading an active component therein to obtain a homogeneous mixture.

(5) Creams

Creams are a semi-solid formulation in the form of an oil-in-water or water-in-oil emulsion to be applied on the skin and lipophilic formulations in the form of a water-in-oil emulsion may also be referred to as oil-based creams. Creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion.

(6) Gels

Gels are a gel formulation to be applied on the skin and examples thereof include water-based gels and oil-based gels. Water-based gels may be generally produced by dissolving or suspending an active component in an additive such as a polymer compound and purified water and allowing crosslinking by heating and cooling or addition of a gel-forming agent. Oil-based gels may be produced by mixing an active component with a liquid oil base such as a glycol or a higher alcohol and an additive.

(7) Plasters and Pressure Sensitive Adhesives

Plasters and pressure sensitive adhesives are a formulation to be adhered on the skin and examples thereof include tapes and cataplasms. Plasters and pressure sensitive adhesives may be generally produced by homogeneously mixing an active component with a base which is a polymer compound or a mixture thereof, spreading the mixture on a support or a liner (release material) and shaping the same. Plasters and pressure sensitive adhesives may be formed as transdermal absorption formulations by using a release-controlled film. An additive such as an adhesive or an absorption-promoting agent may be optionally used for plasters and pressure sensitive adhesives. Tapes refer to a plaster and pressure sensitive adhesive containing abase that contains little water and examples thereof include plasters and the like. Tapes may be generally produced with a base which is a water insoluble natural or synthetic polymer compound such as a resin, a plastic, a rubber or the like by spreading on a fabric or spreading on or incorporating into a plastic film an active component or a homogeneous mixture of an active component and an additive and shaping the product. Tapes may also be produced by incorporating a mixture of an active component and a base or another additive into a release material made of a release-controlled film, a support and a liner (release material) and shaping the same. Cataplasms refer to a plaster and pressure sensitive adhesive containing a base which contains water and may be generally produced by homogeneously mixing an active component with a liquid substance such as purified water or glycerol or homogeneously mixing and kneading a natural or synthetic polymer compound such as a water soluble polymer or a water-absorbable polymer and purified water together with an active component, spreading the mixture on a fabric or the like and shaping the same.

Unless otherwise defined, all technical and scientific terms and abbreviations used herein have the same meanings as those commonly understood by a person skilled in the art to which the present invention belongs.

Contents of all patent literatures and non patent literatures or references explicitly cited herein may be incorporated herein as a part of the present specification.

EXAMPLES

The present invention is hereinafter specifically described by way of Examples and Biological Examples which do not limit the present invention. The present compounds and compounds described in Examples are denominated by using ACD/Name (version 6.00, available from Advanced Chemistry Development Inc.) or Chemdraw Ultra (version 12.0, available from Cambridge Soft).

The solvents described in brackets in the sections of chromatography separation and TLC indicate the elution solvents or developing solvents used and the proportions are represented by volume ratios. The reference to "NH silica" indicates that CHROMATOREX NH TLC PLATE (catalogue No.: 3800003) available from Fuji Silysia Chemical Ltd. was used.

The references to "Hi-flash SI" and "Hi-flash NH" in brackets in the sections of medium pressure preparative liquid chromatography respectively indicate the type of the columns used (Hi-flash SI: silica gel (available from Yamazen Corporation) and Hi-flash NH: aminopropyl group-bonded silica gel (available from Yamazen Corporation)).

LC-MS/ELSD was carried out under the following condition (1):

Condition (1) {column: Waters Xterra MS $C_{18}$ (particle diameter: $5 \times 10^{-6}$ m; column length: 50×4.6 mm I.D.); flow rate: 1.5 mL/min; column temperature: 40° C.; mobile phase (A): 0.1% trifluoroacetic acid aqueous solution; mobile phase (B): 0.1% trifluoroacetic acid-methanol solution; gradient (the ratio of the mobile phase (A):the mobile phase (B)): [0 min.] 95:5; [1 min.] 95:5; [4 min.] 0:100; [4.5 min.] 0:100; [4.51 min.] 95:5; [6 min.] 95:5; detector: UV(PDA), ELSD, MS}.

UPLC-MS/ELSD was carried out under the following condition (2):

Condition (2) {column: Waters ACQUITY $C_{18}$ (particle diameter: $1.7 \times 10^{-6}$ m; column length: 30×2.1 mm I.D.); flow rate: 1.0 mL/min; column temperature: 40° C.; mobile phase (A): 0.1% trifluoroacetic acid aqueous solution; mobile phase (B): 0.1% trifluoroacetic acid-acetonitrile solution; gradient (the ratio of the mobile phase (A):the mobile phase (B)): [0 min.] 95:5; [0.1 min.] 95:5; [1.2 min.] 5:95; [1.4 min.] 5:95; [1.41 min.] 95:5; [1.5 min.] 95:5; detector: UV(PDA), ELSD, MS}.

The numerical values indicated in the sections of NMR are values measured on $^1$H-NMR using the solvents indicated.

In the structural formulae, some functional groups may be indicated with symbols or abbreviations. For example, "Boc" denotes a "tert-butoxycarbonyl group".

Biological Example 2 as described hereinbelow is an example of a test demonstrating the usefulness of the present compounds for acromegaly. However, diseases which the present compounds target are not limited to acromegaly. It has been described above that the present compounds are useful for prophylaxis and/or therapy of all diseases in which somatostatin per se or a hormone modulated by somatostatin is involved.

Reference Example A1 methyl 5-bromo-4-[4-(tert-butoxycarbonylamino)-1-piperidinyl]pyridine-3-carboxylate To a solution of methyl 5-bromo-4-iodopyridine-3-carboxylate (3.0 g) in dimethylformamide (20 mL) produced by the reaction of 5-bromo-4-iodopyridine-3-carboxylic acid (CAS#491588-98-8) with trimethylsilyldiazomethane, triethylamine (1.84 mL) and 4-tert-butoxycarbonylaminopiperidine (CAS#73874-95-0) (2.63 g) were added and the mixture was stirred at 70° C. for 5 hours. The reaction solution was cooled to room temperature, diluted with ethyl acetate and washed with water and a saturated sodium chloride solution. After drying, an organic layer was concentrated. The obtained residue was purified by medium pressure preparative liquid chromatography (available from Yamazen Corporation, YFLC-Wprep-2XY) (Hi-flash SI) (n-hexane:ethyl acetate=1:1) to give a titled compound (2.47 g) having the following physical properties.
Properties: pale yellow-white powder;
TLC (Rf): 0.26 (n-hexane:ethyl acetate=1:2);
NMR (300 MHz, CHLOROFORM-d): δ 8.65 (s, 1H), 8.57 (s, 1H), 4.54 (br. s, 1H), 3.95 (s, 3H), 3.76-3.63 (m, 1H), 3.36-3.25 (m, 2H), 3.16-3.03 (m, 2H), 2.09-1.98 (m, 2H), 1.71-1.59 (m, 2H), 1.47 (s, 9H).

Reference Example A2 methyl 4-[4-(tert-butoxycarbonylamino)-1-piperidinyl]-5-phenylpyridine-3-carboxylate To a solution of the compound (207 mg) produced in Reference Example A1 in 1,4-dioxane (8 mL), tripotassium phosphate (425 mg), phenylboronic acid (CAS#98-80-6) (122 mg) and bis(di-tert-butyl(4-dimethylaminophenyl)phosphine)dichloropalladium(II) (7.1 mg) were added and the mixture was stirred at 90° C. for 2 hours. The reaction solution was cooled to room temperature, diluted with ethyl acetate and washed with water and a saturated sodium chloride solution. After drying, an organic layer was concentrated. The obtained residue was purified by medium pressure preparative liquid chromatography (available from Yamazen Corporation, YFLC-Wprep-2XY) (Hi-flash SI) (n-hexane:ethyl acetate=1:1) to give a titled compound (206 mg) having the following physical properties.
Properties: pale yellow-white oily substance;
TLC (Rf): 0.31 (n-hexane:ethyl acetate=1:2);
MASS (APCI, Pos.): 412 (M+H)$^+$.

Reference Example A3 tert-butyl N-(1-{3-[(3,5-dimethylphenyl)carbamoyl]-5-phenyl-4-pyridyl}-4-piperidinyl)carbamate In an argon atmosphere, a solution of 3,5-dimethylaniline (CAS#108-69-0) (194 mg) in dehydrated tetrahydrofuran (10 mL) was cooled to 0° C., to which a solution of n-butyllithium (1.6 mol) in hexane (2.0 mL) was added and the solution was returned to room temperature and stirred for 10 minutes. The reaction solution was cooled to −78° C. to which a solution of the compound (206 mg) produced in Reference Example A2 in tetrahydrofuran (10 mL) was added. The reaction solution was returned to room temperature over 3 or more hours to which a saturated ammonium chloride aqueous solution was added to terminate the reaction and subjected to extraction with ethyl acetate. An organic layer was washed with a saturated sodium chloride solution, dried and concentrated. The obtained residue was purified by medium pressure preparative liquid chromatography (available from Yamazen Corporation, YFLC-Wprep-2XY) (Hi-flash SI) (n-hexane:ethyl acetate=3:1) to give a titled compound (52 mg) having the following physical properties.
Properties: pale yellow-white powder;
TLC (Rf): 0.33 (n-hexane:ethyl acetate=1:1);
MASS (APCI, Pos.): 501 (M+H)$^+$.

Reference Example B1

4-(4-amino-1-piperidinyl)-N-(3,5-dimethylphenyl)-5-phenyl-pyridine-3-carboxamide To a solution of the compound (52 mg) produced in Reference Example A3 in dichloromethane (2 mL), trifluoroacetic acid (2 mL) was added at room temperature, stirred for 30 minutes and concentrated. The obtained residue was purified by medium pressure preparative liquid chromatography (available from Yamazen Corporation, YFLC-Wprep-2XY) (Hi-flash NH) (ethyl acetate:methanol=95:5) to give a titled compound (26 mg) having the following physical properties.
Properties: beige amorphous;
Purity (LC-MS/ELSD): 100% (retention time: 3.45 min.);
TLC (Rf): 0.24 (ethyl acetate:methanol=9:1, NH silica);
NMR (300 MHz, CHLOROFORM-d): δ 8.94 (br. s, 1H), 8.83 (s, 1H), 8.34 (s, 1H), 7.53-7.28 (m, 7H), 6.81 (s, 1H), 3.21-3.05 (m, 2H), 2.83-2.56 (m, 3H), 2.34 (s, 6H), 1.74-1.59 (m, 2H), 1.48 (br. s, 2H), 1.35-1.18 (m, 2H);
MASS (ESI, Pos.): 401 (M+H)$^+$.

Reference Example 1 tert-butyl N-[1-(3-bromo-5-nitro-4-pyridyl)-4-piperidinyl]carbamate

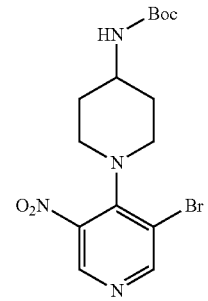 [SMILES: CC(C)(C)OC(=O)NC1CCN(c2c(Br)cncc2[N+](=O)[O-])CC1]

To a solution of 3-bromo-4-chloro-5-nitropyridine (CAS#31872-63-6) (39.18 g) in tetrahydrofuran (200 mL), triethylamine (46 mL) and 4-tert-butoxycarbonylaminopiperidine (CAS#73874-95-0) (36.35 g) were added and the mixture was stirred under ice cooling for 1 hour. The reaction solution was poured into water (800 mL) while stirring and washed thoroughly with water (700 mL). The deposited yellow compound was filtered and dried to give a titled compound (59.78 g) having the following physical properties.

Properties: yellow powder;
TLC (Rf): 0.23 (n-hexane:ethyl acetate=4:1).

Reference Example 1(1)-Reference Example 1(3)

Titled compounds having the following physical properties were obtained in the similar manner as in Reference Example 1 by using, instead of 4-tert-butoxycarbonylaminopiperidine, (4aS,8aS)-tert-butyl octahydro-1H-pyrido[3,4-b][1,4]oxazine-1-carboxylate (CAS#1391733-55-3), tert-butyl (rac-(3R,4R)-3-methoxypiperidin-4-yl)carbamate (CAS#1033748-33-2) or tert-butyl (rac-(3R,4S)-3-methoxypiperidin-4-yl)carbamate (CAS#808739-28-8).

Reference Example 1(1)

(4aS,8aS)-tert-butyl 6-(3-bromo-5-nitropyridin-4-yl)octahydro-1H-pyrido[3,4-b][1,4]oxazine-1-carboxylate

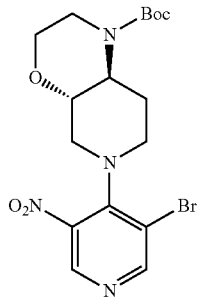 [SMILES: CC(C)(C)OC(=O)N1CCO[C@H]2CN(c3c(Br)cncc3[N+](=O)[O-])CC[C@@H]21]

NMR (300 MHz, CHLOROFORM-d): δ 8.73 (d, J=0.4 Hz, 1H), 8.72 (d, J=0.4 Hz, 1), 4.01-3.81 (m, 2H), 3.81-3.60 (m, 2H), 3.42 (ddd, J=11.9, 4.5, 2.6 Hz, 1H), 3.38-3.19 (m, 3H), 3.06 (td, J=12.6, 2.3 Hz, 1H), 2.95 (dd, J=11.9, 10.1 Hz, 1H), 2.75-2.64 (m, 1H), 2.20-2.03 (m, 1H), 1.47 (s, 9H).

Reference Example 1(2)

tert-butyl (rac-(3R,4R)-1-(3-bromo-5-nitropyridin-4-yl)-3-methoxypiperidin-4-yl)carbamate

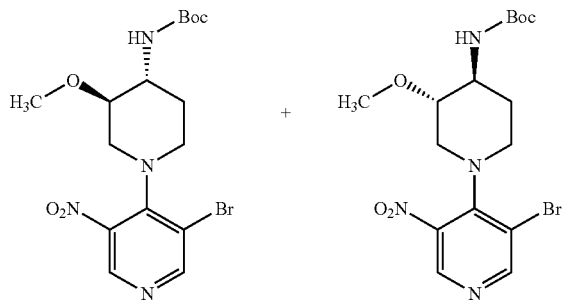

Racemic substances (1:1)

TLC (Rf): 0.46 (n-hexane:ethyl acetate=3:1);
NMR (300 MHz, CHLOROFORM-d): δ 8.74 (s, 1H), 8.73 (s, 1H), 4.63 (br. s, 1H), 3.58 (s, 2H), 3.42 (s, 3H), 3.33 (td, J=9.1, 4.4 Hz, 1H), 3.23-3.04 (m, 2H), 2.85 (dd, J=12.2, 9.1 Hz, 1H), 2.38-2.22 (m, 1H), 1.79-1.61 (m, 1H), 1.46 (s, 9H).

Reference Example 1(3)

tert-butyl (rac-(3R,4S)-1-(3-bromo-5-nitropyridin-4-yl)-3-methoxypiperidin-4-yl)carbamate

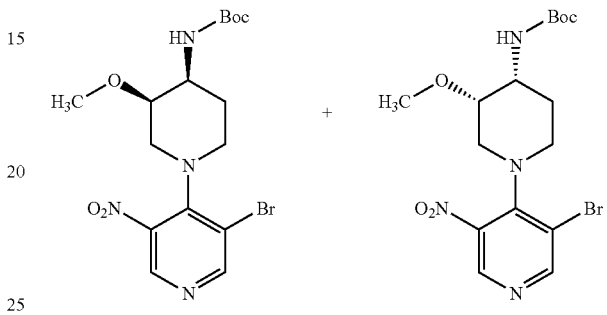

Racemic substances (1:1)

TLC (Rf): 0.64 (n-hexane:ethyl acetate=2:1);
NMR (300 MHz, CHLOROFORM-d): δ 8.74 (s, 1H), 8.72 (s, 1H), 4.99 (d, J=5.7 Hz, 1H), 3.87 (br. s, 1H), 3.59 (s, 1H), 3.47 (q, J=3.3 Hz, 1H), 3.27 (s, 3H), 3.16-2.98 (m, 3H), 2.21 (s, 1H), 1.92-1.76 (m, 1H), 1.47 (s, 9H).

Reference Example 2 tert-butyl N-{1-[3-(3,5-dichlorophenyl)-5-nitro-4-pyridyl]-4-piperidinyl}carbamate

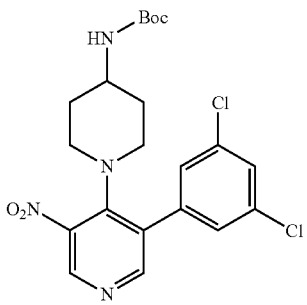

To a solution of the compound (128.35 g) produced in Reference Example 1 in 1,4-dioxane (1283 mL), 2 M tripotassium phosphate aqueous solution (39.72 mL), 3,5-dichlorophenylboronic acid (CAS#67492-50-6) (64.08 g) and tetrakis(triphenylphosphine)palladium(0) (1.84 g) were added and the mixture was stirred at 100° C. for 5 hours. The reaction solution was cooled to room temperature, diluted with ethyl acetate and washed with water and a saturated sodium chloride solution. After drying, an organic layer was concentrated to give a residue (168 g) containing a titled compound having the following physical properties. The obtained residue was used in the next reaction without purification.

Properties: yellow powder;
TLC (Rf): 0.40 (n-hexane:ethyl acetate=4:1);
MASS (ESI, Pos.): 467 (M+H)⁺.

Reference Example 3 tert-butyl N-{1-[3-amino-5-(3,5-dichlorophenyl)-4-pyridyl]-4-piperidinyl}carbamate

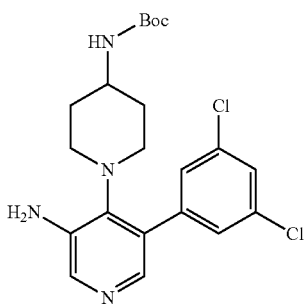 [SMILES: CC(C)(C)OC(=O)NC1CCN(c2c(-c3cc(Cl)cc(Cl)c3)cncc2[N+](=O)[O-])CC1]

A suspension of iron (3.58 g) in acetic acid (80 mL) was heated to 80° C. to which a solution of the compound (6.00 g) produced in Reference Example 2 in acetic acid (10 mL) was added using a dropping funnel and the mixture was stirred for 2 hours. The reaction solution was cooled to room temperature and an insoluble matter was removed by Celite filtration. The filtrate was concentrated and diluted while cooling on ice with tert-butyl methyl ether and 5 N sodium hydroxide aqueous solution to bring the mixture basic. The mixture was again filtered through Celite to remove an insoluble matter and then an organic layer was washed with water and a saturated sodium chloride solution. After drying, the organic layer was concentrated to give a residue (4.40 g) containing a titled compound having the following physical properties. The obtained residue was used in the next reaction without purification.
Properties: brown amorphous;
TLC (Rf): 0.51 (ethyl acetate, NH silica);
MASS (ESI, Pos.): 437 (M+H)⁺.

Reference Example 3(1)

tert-butyl N-{1-[3-amino-5-(3-chloro-5-fluorophenyl)-4-pyridyl]-4-piperidinyl}carbamate

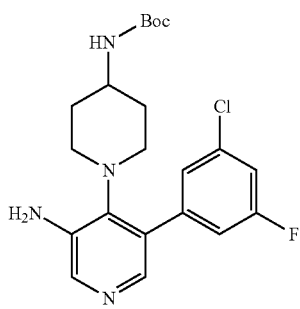 [SMILES: CC(C)(C)OC(=O)NC1CCN(c2c(N)cncc2-c2cc(F)cc(Cl)c2)CC1]

A titled compound having the following physical properties was obtained in the similar procedures as in Reference Examples 2→3 by using, instead of 3,5-dichlorophenylboronic acid, 3-chloro-5-fluorophenylboronic acid (CAS#328956-61-2).

NMR (300 MHz, CHLOROFORM-d): δ 8.09 (s, 1H), 7.75 (s, 1H), 7.16-6.86 (m, 3H), 3.91 (brs, 2H), 3.45 (brs, 1H), 2.96-2.91 (m, 2H), 2.55-2.47 (m, 2H), 1.94-1.91 (m, 2H), 1.43 (s, 9H), 1.47-1.22 (m, 4H); MASS (ESI, Pos.): 421 (M+H)⁺.

Reference Example 4 tert-butyl N-{1-[3-(3,5-dichlorophenyl)-5-iodo-4-pyridyl]-4-piperidinyl}carbamate

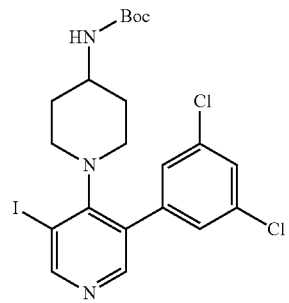 [SMILES: CC(C)(C)OC(=O)NC1CCN(c2c(I)cncc2-c2cc(Cl)cc(Cl)c2)CC1]

A suspension of the compound (1.00 g) produced in Reference Example 3 in acetonitrile was cooled on ice to which boron trifluoride diethyl ether complex (BF₃-Et₂O) (649 mg) and amyl nitrite (0.68 mL) were added using a syringe and the mixture was stirred under ice cooling for 1 hour. To the reaction solution, a solution of sodium iodide (CAS#7681-82-5) (1.02 g) in acetone (5.00 mL) was added and the mixture was heated to room temperature and stirred for 1 hour. To the reaction solution, 1 M sodium hydroxide aqueous solution and a saturated sodium sulphite aqueous solution were added and a deposited target substance was filtered and dried under reduced pressure at room temperature. The dried residue was purified by recrystallisation using acetone and water to give a titled compound (0.85 g) having the following physical properties.
Properties: beige powder;
TLC (Rf): 0.44 (n-hexane:ethyl acetate=4:1).

Example 1

1-{3-(3,5-dichlorophenyl)-5-[4-(trifluoromethyl)phenyl]-4-pyridinyl}-4-piperidineamine

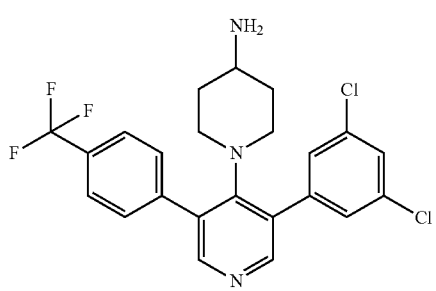 [SMILES: NC1CCN(c2c(-c3ccc(C(F)(F)F)cc3)cncc2-c2cc(Cl)cc(Cl)c2)CC1]

The present compound having the following physical properties was obtained in the similar procedures as in Reference Example 2→ Reference Example B1 by using, instead of the compound produced in Reference Example 1, the compound produced in Reference Example 4 and using, instead of 3,5-dichlorophenylboronic acid, 4-(trifluoromethyl)phenylboronic acid (CAS#128796-39-4).

Properties: white powder;

Purity (UPLC-MS/ELSD): 99.9% (retention time: 0.58 min.);

TLC (Rf): 0.71 (ethyl acetate:methanol=9:1, NH silica);

NMR (300 MHz, METHANOL-d4): δ 8.20 (s, 1H), 8.19 (s, 1H), 7.80 (d, J=8.1 Hz, 1H), 7.62 (d, J=8.1 Hz, 1H), 7.53-7.50 (m, 1H), 7.43 (d, J=1.8 Hz, 2H), 2.91 (br. d, J=13.0 Hz, 2H), 2.52-2.35 (m, 3H), 1.49-1.37 (m, 2H), 1.06-0.88 (m, 2H);

MASS (ESI, Pos.): 466 (M+H)+.

Example 2

1-{3-(3-chloro-5-fluorophenyl)-5-[4-(trifluoromethyl)phenyl]-4-pyridinyl}-4-piperidineamine

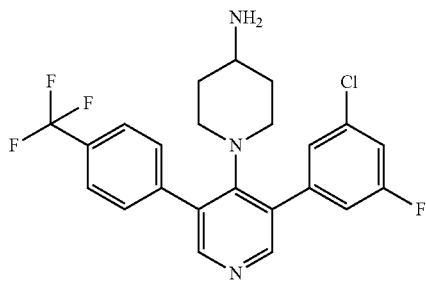 [SMILES: NC1CCN(c2c(-c3ccc(C(F)(F)F)cc3)cncc2-c2cc(F)cc(Cl)c2)CC1]

The present compound having the following physical properties was obtained in the similar procedures as in Reference Example 2→Reference Example 3→Reference Example 4→Example 1 by using, instead of 3,5-dichlorophenylboronic acid, 3-chloro-5-fluorophenylboronic acid (CAS#328956-61-2).

Properties: white powder;

TLC (Rf): 0.32 (ethyl acetate, NH silica);

NMR (300 MHz, CHLOROFORM-d): δ 8.27 (s, 1H), 8.27 (s, 1H), 7.73 (d, J=8.1 Hz, 2H), 7.49 (d, J=8.1 Hz, 2H), 7.24-7.19 (m, 1H), 7.14 (dt, J=8.4, 2.1 Hz, 1H), 7.03 (ddd, J=9.0, 2.1, 1.5 Hz, 1H), 2.85 (d, J=13.0 Hz, 2H), 2.52 (s, 1H), 2.46-2.35 (m, 2H), 1.45 (dd, J=11.6, 2.7 Hz, 2H), 0.94 (qd, J=11.6, 3.9 Hz, 2H);

MASS (ESI, Pos.): 450 (M+H)+.

Example 2(1)-Example 2(7)

The present compounds having the following physical properties were obtained in the similar procedures as in Reference Example 2→Reference Example 3→Reference Example 4→Example 1 by using the compound produced in Reference Example 1 or instead the product produced in Reference Example 1(1), Reference Example 1(2) or Reference Example 1(3), using 3,5-dichlorophenylboronic acid or instead 3-chloro-5-fluorophenylboronic acid, and using 4-(trifluoromethyl)phenylboronic acid or instead a corresponding boronic acid compound.

Example 2(1)

1-{3-(3-chloro-5-fluorophenyl)-5-[4-(difluoromethoxy)phenyl]-4-pyridinyl}-4-piperidineamine

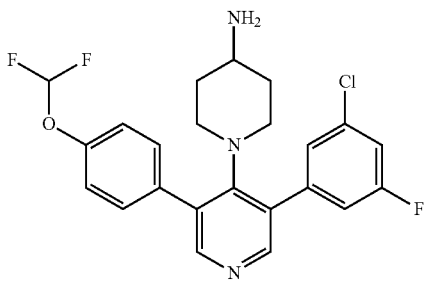 [SMILES: NC1CCN(c2c(-c3ccc(OC(F)F)cc3)cncc2-c2cc(F)cc(Cl)c2)CC1]

Properties: yellow viscous oily substance;

Purity (UPLC-MS/ELSD): 99.3% (retention time: 0.53 min.);

NMR (300 MHz, CHLOROFORM-d): δ 8.26 (s, 1H), 8.25 (s, 1H), 7.33-7.38 (m, 2H), 7.25-7.19 (m, 3H), 7.16-7.10 (m, 1H), 7.06-6.99 (m, 1H), 6.59 (t, J=73.6 Hz, 1H), 2.85 (br. d, J=13.0 Hz, 2H), 2.58-2.32 (m, 3H), 1.52-1.32 (m, 2H), 1.04-0.86 (m, 2H);

MASS (ESI, Pos.): 448 (M+H)+.

Example 2(2)

1-{4-[4-(4-amino-1-piperidinyl)-5-(3,5-dichlorophenyl)-3-pyridinyl]phenyl}cyclopropanecarbonitrile

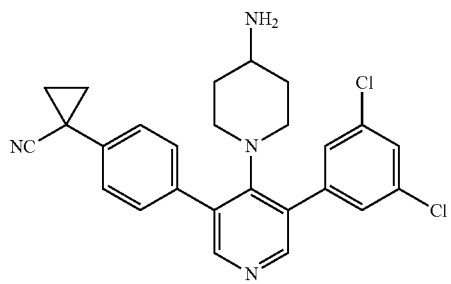 [SMILES: N#CC1(c2ccc(-c3cncc(-c4cc(Cl)cc(Cl)c4)c3N3CCC(N)CC3)cc2)CC1]

Properties: yellow powder;

Purity (UPLC-MS/ELSD): 99.8% (retention time: 0.55 min.);

TLC (Rf): 0.51 (ethyl acetate, NH silica);

NMR (300 MHz, CHLOROFORM-d): δ 8.27-8.20 (m, 2H), 7.43-7.24 (m, 7H), 2.84 (br. d, J=13.0 Hz, 2H), 2.69-2.51 (m, 1H), 2.48-2.30 (m, 2H), 1.83-1.75 (m, 2H), 1.55-1.42 (m, 4H), 1.12-0.93 (m, 2H);

MASS (ESI, Pos.): 449 (M+H)+.

Example 2(3)

1-{3-(3,5-dichlorophenyl)-5-[4-(difluoromethoxy)phenyl]-4-pyridinyl}-4-piperidineamine

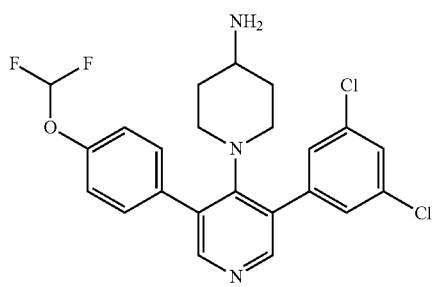 [SMILES: NC1CCN(c2c(-c3ccc(OC(F)F)cc3)cncc2-c2cc(Cl)cc(Cl)c2)CC1]

Purity (UPLC-MS/ELSD): 100% (retention time: 0.54 min.);
TLC (Rf): 0.57 (ethyl acetate:methanol=9:1, NH silica);
NMR (300 MHz, CHLOROFORM-d): δ 8.26 (s, 1H), 8.25 (s, 1H), 7.41-7.30 (m, 5H), 7.26-7.19 (m, 2H), 6.58 (t, J=73.6 Hz, 1H), 2.89-2.78 (m, 2H), 2.57-2.34 (m, 3H), 1.47-1.38 (m, 2H), 1.03-0.86 (m, 2H);
MASS (ESI, Pos.): 464 (M+H)+.

Example 2(4)

2-{4-[4-(4-amino-1-piperidinyl)-5-(3,5-dichlorophenyl)-3-pyridinyl]phenyl}-2-methylpropanenitrile

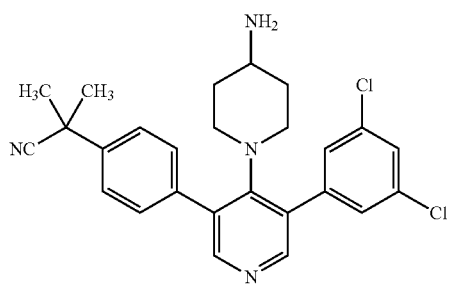 [SMILES: CC(C)(C#N)c1ccc(-c2cncc(-c3cc(Cl)cc(Cl)c3)c2N2CCC(N)CC2)cc1]

Properties: ivory amorphous powder;
Purity (UPLC-MS/ELSD): 94.6% (retention time: 0.70 min.);
TLC (Rf): 0.74 (ethyl acetate:methanol=9:1, NH silica);
NMR (300 MHz, CHLOROFORM-d): δ 8.27 (s, 1H), 8.25 (s, 1H), 7.57 (d, J=8.4 Hz, 2H), 7.41-7.31 (m, 5H), 2.89-2.79 (m, 2H), 2.60-2.32 (m, 3H), 1.79 (s, 6H), 1.50-1.41 (m, 2H), 1.03-0.84 (m, 2H);
MASS (ESI, Pos.): 465 (M+H)+.

Example 2(5)

1-(4-{5-(3,5-dichlorophenyl)-4-[(4aS,8aS)-octahydro-6H-pyrido[3,4-b][1,4]oxazin-6-yl]-3-pyridinyl}phenyl)cyclopropanecarbonitrile

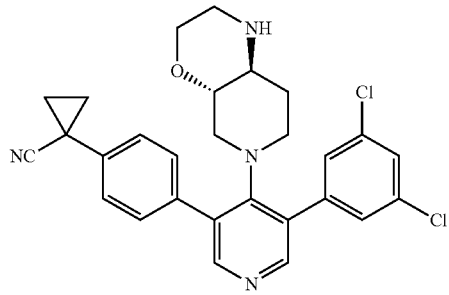 [SMILES: N#CC1(c2ccc(-c3cncc(-c4cc(Cl)cc(Cl)c4)c3N3CC[C@@H]4NCCO[C@H]4C3)cc2)CC1]

Properties: pale yellow powder;
NMR (300 MHz, CHLOROFORM-d): δ 8.27 (s, 2H), 7.42-7.20 (m, 7H), 3.75 (dd, J=11.1, 2.1 Hz, 1H), 3.47 (ddd, J=11.1, 11.1, 2.7 Hz, 1H), 3.00-2.75 (m, 5H), 2.53 (ddd, J=12.6, 12.6, 2.7 Hz, 1H), 2.30-2.18 (m, 2H), 1.84-1.76 (m, 2H), 1.55-1.45 (m, 2H), 1.30 (m, 1H), 1.02 (m, 1H).

Example 2(6)

rac-(3R,4R)-1-{3-(3,5-dichlorophenyl)-5-[4-(trifluoromethyl)phenyl]-4-pyridinyl}-3-methoxy-4-piperidineamine

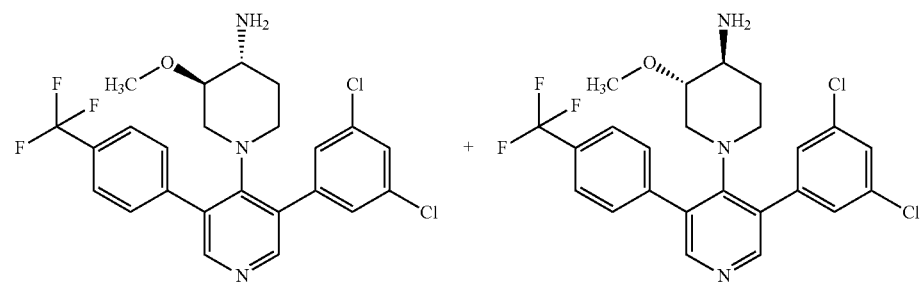

Racemic substances (1:1)

Properties: white powder;
Purity (UPLC-MS/ELSD): 100% (retention time: 0.62 min.);
TLC (Rf): 0.68 (n-hexane:ethyl acetate=1:1, NH silica);
NMR (300 MHz, CHLOROFORM-d): δ 8.29 (s, 1H), 8.28 (s, 1H), 7.74 (d, J=8.1 Hz, 2H), 7.50 (d, J=8.1 Hz, 2H), 7.42 (d, J=1.8 Hz, 2H), 7.39 (t, J=1.8 Hz, 1H), 3.22 (s, 3H), 3.04-2.90 (m, 2H), 2.83-2.67 (m, 2H), 2.59 (s, 1H), 2.24 (dd, J=12.7, 2.1 Hz, 1H), 1.33-1.11 (m, 2H).

Example 2(7)

rac-(3R,4S)-1-{3-(3,5-dichlorophenyl)-5-[4-(trifluoromethyl)phenyl]-4-pyridinyl}-3-methoxy-4-piperidineamine

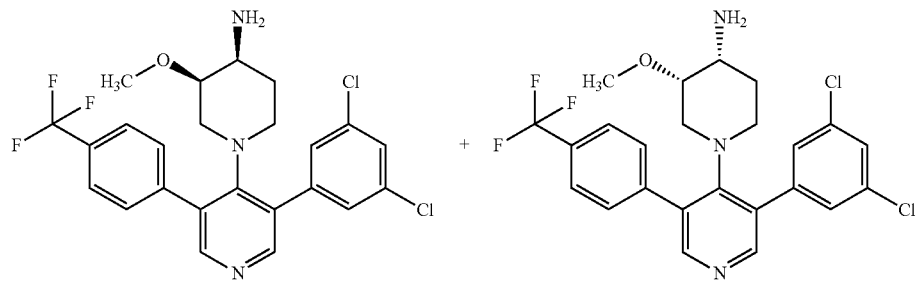

Racemic substances (1:1)

Properties: white powder;
Purity (UPLC-MS/ELSD): 100% (retention time: 0.63 min.);
TLC (Rf): 0.68 (n-hexane:ethyl acetate=1:1, NH silica);
NMR (300 MHz, CHLOROFORM-d): δ 8.30 (s, 1H), 8.29 (s, 1H), 7.76 (d, J=7.9 Hz, 2H), 7.49 (d, J=7.9 Hz, 2H), 7.42 (t, J=1.8 Hz, 1H), 7.28 (d, J=1.8 Hz, 2H), 3.16-3.29 (m, 1H), 2.95 (s, 3H), 2.74-2.61 (m, 1H), 2.45-2.14 (m, 4H), 1.58-1.48 (m, 1H), 1.22-1.03 (m, 1H).

Reference Example 5

2-[(E)-2-(3-fluorophenyl)-1-propenyl]-4,4,5,5-tetramethyl-1,3,2-dioxaborolan

A reaction vessel was dried by heating and purged with argon to which cuprous chloride (206 mg), 4,5-bis(diphenylphosphino)-9,9-dimethylxanthene (1.2 g) and bis(pinacolato)diboron (11.1 g) were added. To the vessel, dehydrated tetrahydrofuran (107 mL) was added and the mixture was stirred at room temperature and added with a solution of sodium t-butoxide in tetrahydrofuran (1 M) (43 mL). To the mixture, 1-ethynyl-3-fluoro-benzene (5.0 g) and methyl iodide (10.4 mL) were added and the mixture was stirred at 35° C. for 18 hours. The reaction solution was filtered through Celite and concentrated. The obtained residue was purified by a silica gel column (n-hexane:ethyl acetate=100:0→4 96:4) to give a titled compound (7.3 g) having the following physical properties.

Properties: pale yellow oily substance;
TLC (Rf): 0.37 (n-hexane:ethyl acetate=12:1).

Example 3

1-{3-(3,5-dichlorophenyl)-5-[(1E)-2-(3-fluorophenyl)-1-propen-1-yl]-4-pyridinyl}-4-piperidineamine

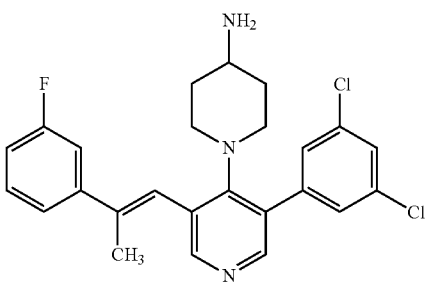 [SMILES: C/C(=C\c1cncc(-c2cc(Cl)cc(Cl)c2)c1N1CCC(N)CC1)c1cccc(F)c1]

The present compound having the following physical properties was obtained in the similar procedures as in Reference Example 2→Reference Example B1 by using, instead of the compound produced in Reference Example 1, the compound produced in Reference Example 4 and using, instead of 3,5-dichlorophenylboronic acid, the compound produced in Reference Example 5.

Properties: white powder;
Purity (UPLC-MS/ELSD): 99.8% (retention time: 0.77 min.);
TLC (Rf): 0.19 (n-hexane:ethyl acetate=2:1, NH silica);
NMR (300 MHz, METHANOL-d4): δ 8.26 (d, J=0.9 Hz, 1H), 8.13 (s, 1H), 7.52-7.50 (m, 1H), 7.39 (m, 5H), 7.09-7.00 (m, 1H), 6.82 (s, 1H), 3.19-3.09 (m, 2H), 2.73-2.53 (m, 3H), 2.22 (d, J=1.3 Hz, 3H), 1.73-1.62 (m, 2H), 1.34-1.18 (m, 2H);
MASS (ESI, Pos.): 456 (M+H)$^+$.

Example 3(1)-Example 3(2)

The present compounds having the following physical properties were obtained in the similar procedures as in Reference Example 2→Reference Example 3→Reference Example 4→Example 3 by using the compound produced in Reference Example 1 or instead the compound produced in Reference Example 1(1), using 3,5-dichlorophenylboronic acid or instead 3-chloro-5-fluorophenylboronic acid and using, instead of the compound produced in Reference Example 5, a corresponding boronic ester.

Example 3(1)

1-{3-(3-chloro-5-fluorophenyl)-5-[(E)-2-(3-chlorophenyl)vinyl]-4-pyridinyl}-4-piperidineamine

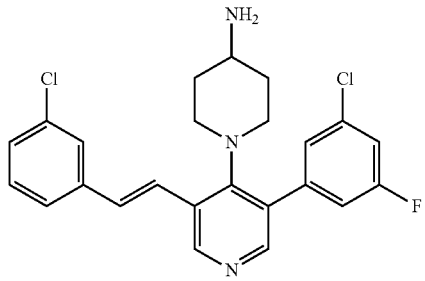 [SMILES: NC1CCN(c2c(/C=C/c3cccc(Cl)c3)cncc2-c2cc(F)cc(Cl)c2)CC1]

Properties: pale yellow powder;
Purity (UPLC-MS/ELSD): 99.9% (retention time: 0.60 min.);
TLC (Rf): 0.65 (ethyl acetate:methanol=9:1, NH silica);
NMR (300 MHz, METHANOL-d4): δ 8.61 (s, 1H), 8.16 (s, 1H), 7.63 (s, 1H), 7.55 (d, J=7.7 Hz, 1H), 7.42-7.05 (m, 6H), 3.23 (br. d, J=13.4 Hz, 2H), 3.15-3.02 (m, 1H), 2.80-2.65 (m, 2H), 1.91 (br. d, J=12.1 Hz, 2H), 1.73-1.54 (m, 2H);
MASS (ESI, Pos.): 442 (M+H)$^+$.

Example 3(2)

(4aS,8aS)-6-{3-(3,5-dichlorophenyl)-5-[(E)-2-(3-fluorophenyl)vinyl]-4-pyridinyl}octahydro-1H-pyrido[3,4-b][1,4]oxazine

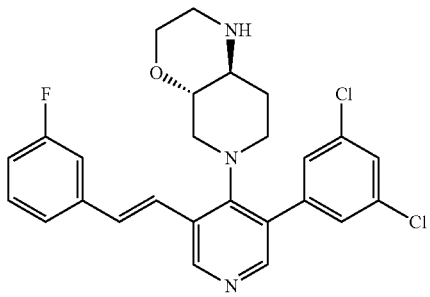 [SMILES: Fc1cccc(/C=C/c2cncc(-c3cc(Cl)cc(Cl)c3)c2N2CC[C@@H]3NCCO[C@H]3C2)c1]

Properties: yellow powder;
Purity (UPLC-MS/ELSD): 99.7% (retention time: 0.78 min.);
TLC (Rf): 0.20 (n-hexane:ethyl acetate=2:1, NH silica);
NMR (300 MHz, METHANOL-d4): δ 8.61 (s, 1H), 8.16 (s, 1H), 7.56-7.52 (m, 1H), 7.47-7.33 (m, 5H), 7.30 (d, J=16.5 Hz, 1H), 7.17 (d, J=16.5 Hz, 1H), 7.09-6.99 (m, 1H), 3.82-3.74 (m, 1H), 3.67-3.55 (m, 1H), 3.23-3.14 (m, 1H), 3.12-3.03 (m, 1H), 3.00-2.70 (m, 3H), 2.47-2.30 (m, 2H), 1.71-1.52 (m, 2H);
MASS (ESI, Pos.): 484 (M+H)$^+$.

Reference Example 6

3-ethynylbenzonitrile

3-Iodobenzonitrile (3.115 g) and copper iodide (103 mg) were mixed and tetrahydrofuran (13 mL) and triethylamine (3.0 mL) were added to the mixture which was stirred at room temperature. After degassing and purging with argon, dichloropalladium triphenylphosphine (191 mg) was added and degassed and purged with argon. To the mixture, ethynyl (trimethyl)silane (2.38 mL) was added dropwise and the mixture was stirred overnight at room temperature. The reaction solution was filtered through Celite and an organic layer was extracted by adding ethyl acetate and water. The resulting organic layer was washed with a saturated ammonium chloride aqueous solution and a sodium chloride solution, dried over anhydrous magnesium sulphate and concentrated. The obtained residue (3.11 g) was dissolved in methanol (20 mL) to which potassium carbonate (1.8 g) was added and the mixture was stirred at room temperature for 30 minutes. The reaction solution was filtered through Celite, washed with methyl tert-butyl ether and concentrated. The obtained residue was purified by a silica gel column (n-hexane:ethyl acetate=100:0→95:5) to give a titled compound (1.22 g) having the following physical properties.

Properties: pale brown liquid;
TLC (Rf): 0.40 (n-hexane:ethyl acetate=13:1).

Reference Example 7

3-[(E)-1-methyl-2-(4,4,5,5-tetramethyl-1,3,2-dioxaborolan-2-yl)vinyl]benzonitrile A titled compound having the following physical properties was obtained in the similar procedure as in Reference Example 5 by using, instead of 1-ethynyl-3-fluoro-benzene, the compound produced in Reference Example 6.

Properties: pale yellow oily substance;
TLC (Rf): 0.32 (n-hexane:ethyl acetate=13:1).

Reference Example 8 tert-butyl N-(1-{3-[(E)-2-(3-cyanophenyl)-1-propenyl]-5-(3,5-dichlorophenyl)-4-pyridyl}-4-piperidinyl)carbamate A titled compound having the following physical properties was obtained in the similar procedure as in Reference Example 2 by using, instead of the compound produced in Reference Example 1, the compound produced in Reference Example 4 and using, instead of 3,5-dichlorophenylboronic acid, the compound produced in Reference Example 7.

TLC (Rf): 0.14 (n-hexane:ethyl acetate=4:1).

Example 4

3-{(1E)-1-[4-(4-amino-1-piperidinyl)-5-(3,5-dichlorophenyl)-3-pyridinyl]-1-propen-2-yl}benzonitrile

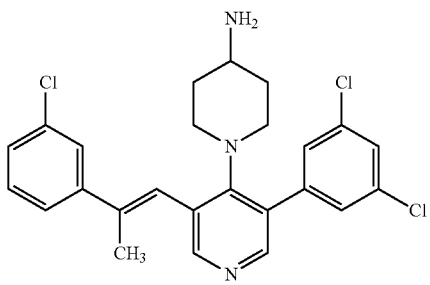 [SMILES: C/C(=C\c1cncc(-c2cc(Cl)cc(Cl)c2)c1N1CCC(N)CC1)c1cccc(Cl)c1]

The present compound having the following physical properties was obtained in the similar procedure as in Reference Example B1 by using, instead of the compound produced in Reference Example A3, the compound produced in Reference Example 8.

Properties: white powder;
Purity (UPLC-MS/ELSD): 100% (retention time: 0.58 min.);
TLC (Rf): 0.31 (n-hexane:ethyl acetate=1:1, NH silica);
NMR (300 MHz, METHANOL-d4): δ 8.30 (s, 1H), 8.17 (s, 1H), 7.97-7.92 (m, 2H), 7.72-7.67 (m, 1H), 7.64-7.57 (m, 1H), 7.53 (t, J=1.9 Hz, 1H), 7.38 (d, J=2.0 Hz, 2H), 6.86 (s, 1H), 3.23-3.13 (m, 2H), 2.90-2.76 (m, 1H), 2.75-2.63 (m, 2H), 2.25 (d, J=1.1 Hz, 3H), 1.79-1.69 (m, 2H), 1.41-1.25 (m, 2H);
MASS (ESI, Pos.): 463 (M+H)+.

Example 4(1)

3-{(E)-2-[4-(4-amino-1-piperidinyl)-5-(3,5-dichlorophenyl)-3-pyridinyl]vinyl}benzonitrile

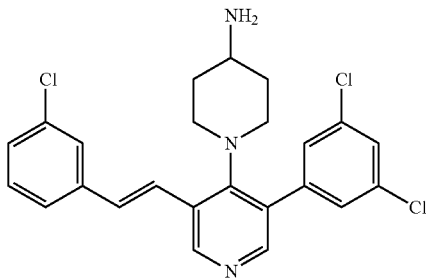 [SMILES: NC1CCN(c2c(/C=C/c3cccc(Cl)c3)cncc2-c2cc(Cl)cc(Cl)c2)CC1]

The present compound having the following physical properties was obtained in the similar procedures as in Reference Example 8→Example 4 by using, instead of the compound produced in Reference Example 7, a corresponding boronic ester.

Properties: yellow powder;
Purity (UPLC-MS/ELSD): 97.7% (retention time: 0.59 min.);
TLC (Rf): 0.51 (ethyl acetate, NH silica);
NMR (300 MHz, CHLOROFORM-d): δ 8.62 (s, 1H), 8.22 (s, 1H), 7.83-7.74 (m, 2H), 7.63-7.46 (m, 2H), 7.43-7.36 (m, 1H), 7.27 (d, J=16.1 Hz, 1H), 7.19 (d, J=1.8 Hz, 2H), 7.04 (s, 1H), 3.08 (br. d, J=13.0 Hz, 2H), 2.87-2.71 (m, 1H), 2.70-2.58 (m, 2H), 1.85-1.72 (m, 2H), 1.50-1.30 (m, 2H);
MASS (ESI, Pos.): 449 (M+H)+.

Reference Example 9 tert-butyl N-(1-{3-[(E)-2-(3-cyanophenyl)-1-propenyl]-5-(3,5-dichlorophenyl)-4-pyridyl}-4-piperidinyl)-N-ethylcarbamate A solution of the compound (82 mg) produced in Reference Example 8 in anhydrous dimethylformamide (1 mL) was stirred in an argon atmosphere at 0° C. To the solution, ethyl iodide (171 microL) and sodium hydride (17 mg) were added and the mixture was stirred at 0° C. The reaction was completed by appropriately adding sodium hydride and then a saturated ammonium chloride aqueous solution was added. An organic layer was extracted by adding to the reaction solution ethyl acetate and water. The resulting organic layer was washed with water and a saturated sodium chloride solution, dried over anhydrous magnesium sulphate and then concentrated. The obtained residue was purified by a silica gel column (n-hexane:ethyl acetate=90:10→70:30) to give a titled compound (10 mg) having the following physical properties.

TLC (Rf): 0.18 (n-hexane:ethyl acetate=4:1).

Example 5

3-[(1E)-1-{5-(3,5-dichlorophenyl)-4-[4-(ethylamino)-1-piperidinyl]-3-pyridinyl}-1-propen-2-yl]benzonitrile

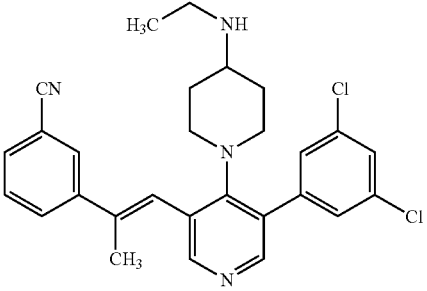 [SMILES: CCNC1CCN(c2c(/C=C(\C)c3cccc(C#N)c3)cncc2-c2cc(Cl)cc(Cl)c2)CC1]

The present compound having the following physical properties was obtained in the similar procedure as in Reference Example B1 by using, instead of the compound produced in Reference Example A3, the compound produced in Reference Example 9.

Properties: brown powder;
Purity (UPLC-MS/ELSD): 97.1% (retention time: 0.62 min.);
TLC (Rf): 0.27 (n-hexane:ethyl acetate=1:1, NH silica);
NMR (300 MHz, METHANOL-d4): δ 8.30 (d, J=0.7 Hz, 1H), 8.16 (s, 1H), 7.99-7.93 (m, 2H), 7.72-7.67 (m, 1H), 7.63-7.56 (m, 1H), 7.53-7.51 (m, 1H), 7.39-7.35 (m, 2H), 6.86 (s, 1H), 3.24-3.14 (m, 2H), 2.77-2.58 (m, 5H), 2.25 (d, J=1.3 Hz, 3H), 1.86-1.76 (m, 2H), 1.39-1.27 (m, 2H), 1.12 (t, J=7.2 Hz, 3H);
MASS (ESI, Pos.): 491 (M+H)+.

Example 5(1)-Example 5(6)

The present compounds having the following physical properties were obtained in the similar procedures as in Reference Example 9→Example 5 by using, instead of the compound produced in Reference Example 8, corresponding compounds.

Example 5(1)

1-{3-(3,5-dichlorophenyl)-5-[4-(trifluoromethyl)phenyl]-4-pyridinyl}-N-ethyl-4-piperidineamine

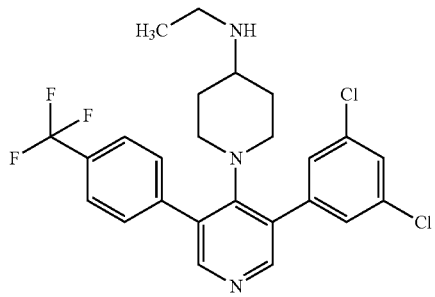 [SMILES: CCNC1CCN(c2c(-c3ccc(C(F)(F)F)cc3)cncc2-c2cc(Cl)cc(Cl)c2)CC1]

Properties: white amorphous powder;
Purity (UPLC-MS/ELSD): 100% (retention time: 0.67 min.);
TLC (Rf): 0.63 (n-hexane:ethyl acetate=1:1, NH silica);
NMR (300 MHz, CHROLOFORM-d): δ 8.26 (s, 1H), 8.25 (s, 1H), 7.73 (d, J=8.1 Hz, 2H), 7.49 (d, J=8.1 Hz, 2H), 7.40 (t, J=1.8 Hz, 1H), 7.29 (d, J=1.8 Hz, 2H), 2.86 (d, J=12.6 Hz, 2H), 2.56 (q, J=7.0 Hz, 2H), 2.40 (dt, J=12.6, 3.2 Hz, 2H), 2.37-2.25 (m, 1H), 1.53-1.41 (m, 2H), 1.05 (t, J=7.0 Hz, 3H), 1.02-0.89 (m, 2H);
MASS (ESI, Pos.): 494 (M+H)$^+$.

Example 5(2)

1-(4-{5-(3,5-dichlorophenyl)-4-[4-(ethylamino)-1-piperidinyl]-3-pyridinyl}phenyl)cyclopropanecarbonitrile

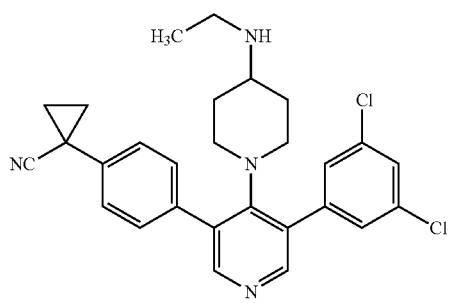 [SMILES: CCNC1CCN(c2c(-c3ccc(C4(C#N)CC4)cc3)cncc2-c2cc(Cl)cc(Cl)c2)CC1]

Properties: yellow amorphous powder;
Purity (UPLC-MS/ELSD): δ 8.2% (retention time: 0.74 min.);
TLC (Rf): 0.75 (ethyl acetate, NH silica);
NMR (300 MHz, CHLOROFORM-d): δ 8.26-8.21 (m, 2H), 7.44-7.25 (m, 7H), 2.87 (br. d, J=12.8 Hz, 2H), 2.58 (q, J=7.1 Hz, 2H), 2.51-2.28 (m, 3H), 1.84-1.76 (m, 2H), 1.59-1.42 (m, 4H), 1.12-0.93 (m, 5H); MASS (ESI, Pos.): 491 (M+H)$^+$.

Example 5(3)

1-{3-(3,5-dichlorophenyl)-5-[4-(difluoromethoxy)phenyl]-4-pyridinyl}-N-ethyl-4-piperidineamine

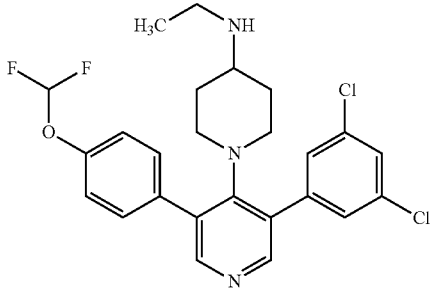 [SMILES: CCNC1CCN(c2c(-c3ccc(OC(F)F)cc3)cncc2-c2cc(Cl)cc(Cl)c2)CC1]

Purity (UPLC-MS/ELSD): 99.9% (retention time: 0.57 min.);
TLC (Rf): 0.60 (ethyl acetate:methanol=9:1, NH silica);
NMR (300 MHz, CHLOROFORM-d): δ 8.25 (s, 1H), 8.23 (s, 1H), 7.40-7.33 (m, 3H), 7.30-7.28 (m, 2H), 7.25-7.20 (m, 2H), 6.59 (t, J=73.7 Hz, 1H), 2.93-2.81 (m, 2H), 2.56 (q, J=7.1 Hz, 2H), 2.47-2.25 (m, 3H), 1.51-1.43 (m, 2H), 1.05 (t, J=7.1 Hz, 3H), 1.01-0.86 (m, 2H); MASS (ESI, Pos.): 492 (M+H)$^+$.

Example 5(4)

2-(4-{5-(3,5-dichlorophenyl)-4-[4-(ethylamino)-1-piperidinyl]-3-pyridinyl}phenyl)-2-methylpropanenitrile

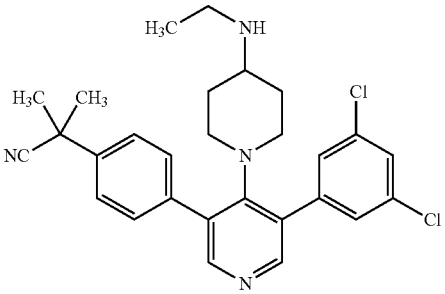 [SMILES: CCNC1CCN(c2c(-c3ccc(C(C)(C)C#N)cc3)cncc2-c2cc(Cl)cc(Cl)c2)CC1]

Properties: pale yellow amorphous powder;
Purity (UPLC-MS/ELSD): 99.4% (retention time: 0.59 min.);
TLC (Rf): 0.42 (n-hexane:ethyl acetate=1:1, NH silica);
NMR (300 MHz, CHLOROFORM-d): δ 8.25 (s, 1H), 8.23 (s, 1H), 7.57 (d, J=8.6 Hz, 2H), 7.42-7.29 (m, 5H), 2.87 (br. d, J=13.0 Hz, 2H), 2.56 (q, J=7.1 Hz, 2H), 2.47-2.24 (m, 3H), 1.79 (s, 6H), 1.58-1.47 (m, 2H), 1.05 (t, J=7.1 Hz, 3H), 1.01-0.88 (m, 2H);
MASS (ESI, Pos.): 493 (M+H)$^+$.

Example 5(5)

1-{3-(3,5-dichlorophenyl)-5-[(1E)-2-(3-fluorophenyl)-1-propen-1-yl]-4-pyridinyl}-N-ethyl-4-piperidineamine

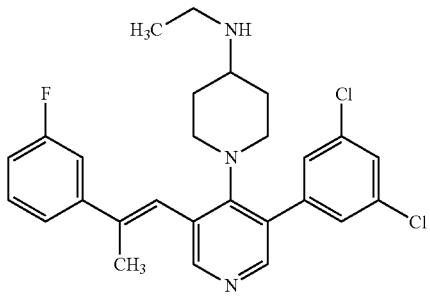

Properties: yellow powder;
Purity (UPLC-MS/ELSD): 100% (retention time: 0.65 min.);
TLC (Rf): 0.30 (n-hexane:ethyl acetate=3:1, NH silica);
NMR (300 MHz, CHLOROFORM-d): δ 8.36 (s, 1H), 8.20 (s, 1H), 7.44-7.33 (m, 3H), 7.24-7.19 (m, 3H), 7.08-6.95 (m, 1H), 6.75 (s, 1H), 3.16-3.05 (m, 2H), 2.75-2.54 (m, 5H), 2.24 (s, 3H), 1.85-1.74 (m, 2H), 1.43-1.31 (m, 2H), 1.11 (t, J=7.1 Hz, 3H);
MASS (ESI, Pos.): 484 (M+H)$^+$.

Example 5(6)

3-[(E)-2-{5-(3,5-dichlorophenyl)-4-[4-(ethylamino)-1-piperidinyl]-3-pyridinyl}vinyl]benzonitrile

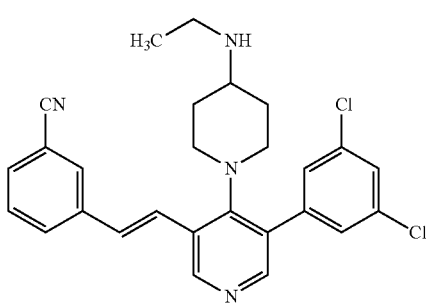 [SMILES: CCNC1CCN(c2c(/C=C/c3cccc(C#N)c3)cncc2-c2cc(Cl)cc(Cl)c2)CC1]

Properties: yellow powder;
Purity (UPLC-MS/ELSD): 100% (retention time: 0.66 min.);
TLC (Rf): 0.52 (n-hexane:ethyl acetate=2:1, NH silica);
NMR (300 MHz, CHLOROFORM-d): δ 8.62 (s, 1H), 8.22 (s, 1H), 7.86-7.79 (m, 1H), 7.78-7.75 (m, 1H), 7.61-7.56 (m, 1H), 7.54-7.48 (m, 1H), 7.42 (t, J=1.9 Hz, 1H), 7.27 (d, J=16.5 Hz, 1H), 7.18 (d, J=1.8 Hz, 2H), 7.02 (d, J=16.5 Hz, 1H), 3.17-3.04 (m, 2H), 2.73 (q, J=7.1 Hz, 2H), 2.68-2.56 (m, 3H), 1.93-1.82 (m, 2H), 1.58-1.41 (m, 2H), 1.15 (t, J=7.1 Hz, 3H);
MASS (ESI, Pos.): 477 (M+H)$^+$.

Reference Example 10 benzyl (3R,4R)-4-[benzyl(tert-butoxycarbonyl)amino]-3-hydroxypiperidine-1-carboxylate To a solution of tert-butyl N-benzyl-N-[(3R,4R)-3-hydroxy-4-piperidinyl]carbamate (Synlett, 2013, 24, 0305-0312; Organic Process Research and Development, 2012, 16, 1558-1565) (5.8 g) in methylene chloride (47 mL), triethylamine (7.9 mL) was added and the mixture was stirred in an argon atmosphere at −5° C. To the mixture, benzyl chloroformate (3.6 g) was added and the mixture was stirred at room temperature for 2 hours. The reaction solution was added with water and extracted with methylene chloride, and the resulting organic layer was washed with a sodium chloride solution. After dried over anhydrous magnesium sulphate, the organic layer was concentrated. The obtained residue was purified by a silica gel column (n-hexane:ethyl acetate=84:16→63:37) to give a titled compound (6.7 g) having the following physical properties.
Properties: pale purple oily substance;
TLC (Rf): 0.68 (n-hexane:ethyl acetate=1:1).

Reference Example 11 benzyl (3R,4R)-4-[benzyl(tert-butoxycarbonyl)amino]-3-methylsulphonyloxy-piperidine-1-carboxylate To a solution of the compound (6.51 g) produced in Reference Example 10 in methylene chloride (50 mL), N,N-diisopropylethylamine (7.7 mL) was added and the mixture was stirred at 0° C. Methanesulphonyl chloride (1.7 mL) was added and the mixture was stirred at room temperature for 30 minutes. The reaction solution was added with water and extracted with methylene chloride. The resulting organic layer was washed with sodium chloride solution, dried over anhydrous magnesium sulphate and concentrated. The obtained residue was purified on a silica gel column (n-hexane:ethyl acetate=90:10→75:25) to give a titled compound (5.4 g) having the following physical properties.
Properties: colourless oily substance;
TLC (Rf): 0.51 (n-hexane:ethyl acetate=3:2).

Reference Example 12 benzyl (3aS,7aR)-1-benzyl-2-oxo-4,6,7,7a-tetrahydro-3aH-oxazolo[5,4-c]pyridine-5-carboxylate A solution of the compound (3.4 g) produced in Reference Example 11 in toluene (20 mL) was stirred at 100° C. for 30 minutes. The reaction solution was left to cool to room temperature, added with water and extracted with ethyl acetate. The resulting organic layer was washed with a sodium chloride solution, dried over anhydrous magnesium sulphate and then concentrated. The obtained residue was purified by a silica gel column (n-hexane:ethyl acetate=75:25→50:50) to give a titled compound (1.2 g) having the following physical properties.
Properties: colourless oily substance;
TLC (Rf): 0.21 (n-hexane:ethyl acetate=1:1).

Reference Example 13

(3aS,7aR)-1-benzyl-3a,4,5,6,7,7a-hexahydrooxazolo[5,4-c]pyridin-2-one

To a solution of the compound (1.2 g) produced in Reference Example 12 in ethanol (10 mL), palladium hydroxide/carbon (Pd 20%) (a wet product with about 50% water) (230 mg) was added and the mixture was stirred in a hydrogen atmosphere at room temperature for 6 hours. The reaction solution was filtered through Celite and the solvent was then distilled off to give a titled compound (0.78 g) having the following physical properties.
Properties: pale yellow solid;
TLC (Rf): 0.19 (ethyl acetate:methanol:28% aqueous ammonia=80:20:2).

Reference Example 14

(3aS,7aR)-1-benzyl-5-(3-bromo-5-nitro-4-pyridyl)-4, 6,7,7a-tetrahydro-3aH-oxazolo[5,4-c]pyridin-2-one A titled compound having the following physical properties was obtained in the similar procedure as in Reference Example 1 by using, instead of 4-tert-butoxycarbonylaminopiperidine, the compound produced in Reference Example 13.
Properties: yellow powder;
TLC (Rf): 0.25 (n-hexane:ethyl acetate=2:1).

Reference Example 15

(3aS,7aR)-1-benzyl-5-[3-(3,5-dichlorophenyl)-5-iodo-4-pyridyl]-4,6,7,7a-tetrahydro-3aH-oxazolo[5, 4-c]pyridin-2-one A titled compound having the following physical properties was obtained in the similar procedures as in Reference Example 2→Reference Example 3→Reference Example 4 by using, instead of the compound produced in Reference Example 1, the compound produced in Reference Example 14.
Properties: yellow powder;
TLC (Rf): 0.46 (n-hexane:ethyl acetate=2:1).

Reference Example 16

(3aS,7aR)-1-benzyl-5-{3-(3,5-dichlorophenyl)-5-[4-(trifluoromethyl)phenyl]-4-pyridyl}-4,6,7,7a-tetrahydro-3aH-oxazolo[5,4-c]pyridin-2-one A titled compound having the following physical properties was obtained in the similar procedure as in Reference Example 2 by using, instead of the compound produced in Reference Example 1, the compound produced in Reference Example 15 and using, instead of 3,5-dichlorophenylboronic acid, 4-(trifluoromethyl)phenylboronic acid (CAS#128796-39-4).
Properties: yellow oily substance;
Retention time (UPLC): 0.99 min.

Reference Example 17

(3S,4R)-4-(benzylamino)-1-{3-(3,5-dichlorophenyl)-5-[4-(trifluoromethyl)phenyl]-4-pyridyl}piperidin-3-ol To a solution of the compound (108 mg) produced in Reference Example 16 in ethanol (2 mL), 5 N sodium hydroxide aqueous solution (0.3 mL) was added and the mixture was stirred at 90° C. for 24 hours. The reaction solution was left to cool to room temperature, added with water and extracted with methylene chloride. After drying, the resulting organic layer was concentrated to give a residue (100 mg) containing a titled compound having the following physical properties. The obtained residue was used in the next reaction without purification.
Retention time (UPLC): 0.72 min.

Example 6

(3S,4R)-4-amino-1-{3-(3,5-dichlorophenyl)-5-[4-(trifluoromethyl)phenyl]-4-pyridinyl}-3-piperidinol

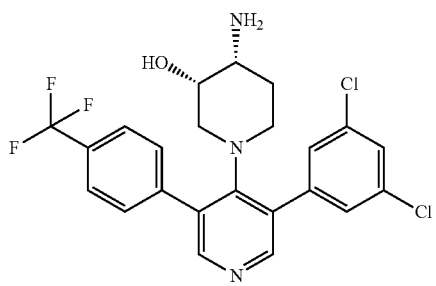 [SMILES: N[C@@H]1CCN(c2c(-c3ccc(C(F)(F)F)cc3)cncc2-c2cc(Cl)cc(Cl)c2)C[C@@H]1O]

To a solution of the compound (100 mg) produced in Reference Example 17 in toluene (2 mL), isopropyl (NE)-N-isopropoxycarbonyliminocarbamate (38 microL) was added and the mixture was stirred at 110° C. for 1 hour. The reaction solution was left to cool to room temperature, added with 1 N hydrochloric acid (1 mL) and stirred at room temperature for 2 hours. The reaction solution was cooled to 0° C., neutralised with 1 N sodium hydroxide aqueous solution added with a saturated aqueous sodium bicarbonate and extracted with ethyl acetate. The resulting organic layer was washed with a sodium chloride solution, dried over anhydrous sodium sulphate and concentrated. The obtained residue was purified by an amino-functionalised silica gel column (n-hexane:ethyl acetate=75:25→0:100, ethyl acetate:methanol=100:0→95:5) to give the present compound (30 mg) having the following physical properties.
Properties: pale yellow powder;
Purity (UPLC-MS/ELSD): 100% (retention time: 0.60 min.);
TLC (Rf): 0.69 (n-hexane:ethyl acetate=1:4, NH silica);
NMR (300 MHz, CHLOROFORM-d): δ 8.29 (s, 1H), 8.29 (s, 1H), 7.74 (d, J=7.9 Hz, 2H), 7.51 (d, J=8.1 Hz, 2H), 7.47 (d, J=1.8 Hz, 2H), 7.43-7.39 (m, 1H), 3.42-3.35 (m, 1H), 3.05-2.94 (m, 1H), 2.80-2.59 (m, 3H), 2.26 (dd, J=12.6, 2.2 Hz, 1H), 1.19-1.07 (m, 2H); MASS (ESI, Pos.): 482 (M+H)$^+$.

Reference Example 18 tert-butyl {1-[3-(3-chloro-5-fluorophenyl)-5-(3-chlorobenzamide)pyridin-4-yl]piperidin-4-yl}carbamate

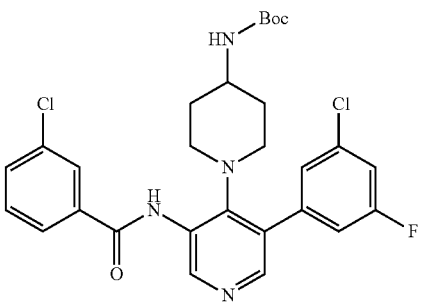 [SMILES: CC(C)(C)OC(=O)NC1CCN(c2c(NC(=O)c3cccc(Cl)c3)cncc2-c2cc(F)cc(Cl)c2)CC1]

To a solution of the compound (150 mg) produced in Reference Example 3(1) in dichloromethane (2 mL), pyridine (0.5 mL) and 3-chlorobenzoyl chloride (72 microL) were added at 0° C. and the mixture was stirred at room temperature for 1 hour. The reaction solution was added with water, extracted with ethyl acetate and then washed with a saturated sodium chloride solution. An organic layer was dried and concentrated. The obtained residue was purified by medium pressure preparative liquid chromatography (available from Yamazen Corporation, YFLC-Wprep-2XY) (Hi-flash SI) (n-hexane:ethyl acetate=1:1) to give a titled compound (198 mg) having the following physical properties.

TLC (Rf): 0.58 (ethyl acetate, NH silica);
MASS (ESI, Pos.): 559 (M+H)$^+$.

Example 7

N-[4-(4-amino-1-piperidinyl)-5-(3-chloro-5-fluorophenyl)-3-pyridinyl]-3-chlorobenzamide

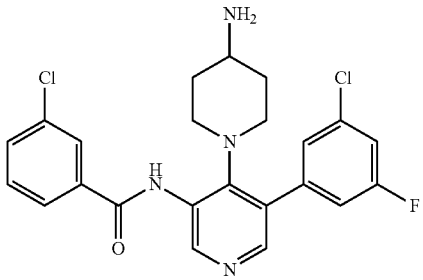 [SMILES: NC1CCN(c2c(NC(=O)c3cccc(Cl)c3)cncc2-c2cc(F)cc(Cl)c2)CC1]

The present compound having the following physical properties was obtained in the similar procedure as in Reference Example B1 by using, instead of the compound produced in Reference Example A3, the compound produced in Reference Example 18.

Properties: pale yellow powder;
Purity (LC-MS/ELSD): 100% (retention time: 0.50 min.);
TLC (Rf): 0.56 (ethyl acetate:methanol=10:1, NH silica);
NMR (300 MHz, CHLOROFORM-d): δ 9.68 (s, 1H), 8.88 (s, 1H), 8.14 (s, 1H), 7.95 (t, J=1.8 Hz, 1H), 7.85-7.77 (m, 1H), 7.64-7.44 (m, 2H), 7.23-7.16 (m, 1H), 7.14-7.09 (m, 1H), 6.99-6.89 (m, 1H), 2.99-2.87 (m, 2H), 2.78-2.51 (m, 3H), 1.93-1.77 (m, 2H), 1.48-1.19 (m, 2H);
MASS (ESI, Pos.): 459 (M+H)$^+$.

Example 7(1)

N-[4-(4-amino-1-piperidinyl)-5-(3,5-dichlorophenyl)-3-pyridinyl]-5-fluoro-2-methoxybenzamide

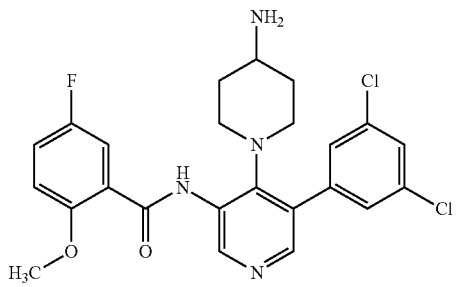 [SMILES: COc1ccc(F)cc1C(=O)Nc1cncc(-c2cc(Cl)cc(Cl)c2)c1N1CCC(N)CC1]

The present compound having the following physical properties was obtained in the same procedures as in Reference Example 18→Example 7 by using, instead of the compound produced in Reference Example 3(1), the compound produced in Reference Example 3 and using, instead of 3-chlorobenzoyl chloride, 5-fluoro-2-methoxybenzoyl chloride (CAS#704-03-0).

Purity (LC-MS/ELSD): 99.9% (retention time: 0.54 min.);
TLC (Rf): 0.64 (ethyl acetate:methanol=9:1, NH silica);
NMR (300 MHz, METHANOL-d4): δ 8.84 (s, 1H), 8.09 (s, 1H), 7.81-7.76 (m, 1H), 7.55 (dd, J=2.00, 1.80 Hz, 1H), 7.41 (d, J=1.83 Hz, 2H), 7.39-7.24 (m, 2H), 4.08 (s, 3H), 3.14-3.02 (m, 2H), 2.76-2.64 (m, 2H), 2.63-2.51 (m, 1H), 1.75-1.64 (m, 2H), 1.35-1.16 (m, 2H); MASS (ESI, Pos.): 489 (M+H)+.

Biological Example 1

Evaluation of SSTR2 Agonistic Activity Using Cells Expressing Human SSTR2

[Procedures]
(1) Isolation of Human SSTR2 Gene

Human brain cDNA was purchased from Ambion (catalogue No.: 7962; Lot No.: 040200121). PCR primers, hSSTR2_F1_XhoI: 5'-CACCCTCGAGGACATGGCG-GATGAGCCACTCAAT-3' (SEQ ID NO: 1) and hSSTR2_R1_EcoRI: 5'-CCTTGAATTCGATACTG-GTTTGGAGGTCTCCATT-3' (SEQ ID NO: 2) were designed on the basis of the sequence GenBank NM_001050.

PCR reaction (95° C. for 2 min.→[98° C. for 10 sec., 60° C. for 30 sec. and 68° C. for 90 sec.]×30 cycles) was carried out using the human brain cDNA as a template and using KOD-plus-(TOYOBO Co., Ltd.). The amplified PCR product was subjected to 1% agarose gel electrophoresis, purified using QIAquick Gel Extraction Kit (QIAGEN) and digested with restriction enzymes XhoI and EcoRI. The digested fragments were ligated to an expression vector (pIRESneo-Myc) using the DNA Ligation Kit Ver. 2 (Takara) and used for transformation of E. coli DH5a. The plasmid pIRESneo-Myc/hSSTR2 was prepared and the DNA sequence thereof was confirmed.

(2) Culture of CHO-K1 Cells

CHO-K1 (−) was cultured in Ham's F-12 medium (containing foetal bovine serum (10%), penicillin (100 U/mL) and streptomycin (0.1 mg/mL)). The transduced cells were cultured in the same medium supplemented with Geneticin (1 mg/mL).

(3) Transduction of CHO-K1 Cells

CHO-K1(−) cells were transduced with the plasmid pIRESneo-Myc/hSSTR2 using Lipofectamine 2000 (Invitrogen). After 48 hours, selection was carried out by replacing the medium with the one containing 1 mg/mL of Geneticin to establish a stable overexpressing cell line (SSTR2-CHO-K1).

(4) Evaluation of SSTR2 Agonistic Activity

The human SSTR2 agonistic activity of a test compound was evaluated according to the following procedures by using a suppression activity of intracellular cyclic AMP (cAMP) production by forskolin stimulation as an index. SSTR2-CHO-K1 cells suspended in Ham's F-12 medium (containing foetal bovine serum (10%), penicillin (100 U/mL) and streptomycin (0.1 mg/mL)) supplemented with 0.25 mg/mL of Geneticin were inoculated into a 96-well plate at a density of 4.0×10$^4$ cells/0.1 mL per well. On the next day, the medium was removed and washed twice with 0.1 mL of wash buffer [0.1% bovine serum albumin (BSA), 20 mmol/L 4-(2-hydroxyethyl)-1-piperazineethane sulphonic acid (HEPES)-containing Hank's balanced salt solution (HBSS)]. An assay buffer [500 nmol/L 3-isobutyl-1-methylxanthine (IBMX), 0.1% BSA, 20 mmol/L HEPES-containing HBSS] was added to the wells at 0.06 mL per well and the plate was incubated for 15 minutes under the conditions of 5% carbon dioxide and 37° C. Thereafter, an assay buffer containing a test compound at a concentration twice as high as the final concentration and 0.02 mmol/L of forskolin was added to wells at 0.06 mL per well and the plate was incubated for 30 minutes under the conditions of 5% carbon dioxide and 37° C. Thereafter, the Assay/Lysis buffer included in the cAMP-Screen® kit (available from Applied Biosystems) was added to wells at 0.12 mL per well and the plate was incubated for 30 minutes under the conditions of 5% carbon dioxide and 37° C. The concentration of cAMP in samples were measured by ELISA according to the instruction of the kit. The 50% effective concentration ($EC_{50}$) of the human SSTR2 agonistic activity was calculated, after determining the percentage (%) of suppression of cAMP production by forskolin stimulation for each sample with the percentage of 1000 nmol/L of octreotide being taken as 100%, by non-linear regression analysis with respect to the independent variable of the common logarithmic concentration of a test compound and the dependent variable of the percentage of the corresponding concentration.

[Results]

The present compounds exhibited strong SSTR2 agonistic activity. The compounds and EC50 values are correlated as follows.

Compound produced in Example 1: 0.031 nmol/L
Compound produced in Example 2: 0.083 nmol/L
Compound produced in Example 2(1): 0.041 nmol/L
Compound produced in Example 2(2): 0.013 nmol/L
Compound produced in Example 2(3): 0.021 nmol/L
Compound produced in Example 2(4): 0.024 nmol/L
Compound produced in Example 2(5): 0.050 nmol/L
Compound produced in Example 2(6): 0.47 nmol/L
Compound produced in Example 2(7): 0.17 nmol/L
Compound produced in Example 3: 0.040 nmol/L
Compound produced in Example 3(1): 0.11 nmol/L
Compound produced in Example 3(2): 0.097 nmol/L
Compound produced in Example 4: 0.034 nmol/L
Compound produced in Example 4(1): 0.038 nmol/L
Compound produced in Example 5: 0.047 nmol/L
Compound produced in Example 5(1): 0.045 nmol/L
Compound produced in Example 5(2): 0.036 nmol/L
Compound produced in Example 5(3): 0.028 nmol/L
Compound produced in Example 5(4): 0.021 nmol/L
Compound produced in Example 5(5): 0.071 nmol/L
Compound produced in Example 5(6): 0.048 nmol/L
Compound produced in Example 6: 0.027 nmol/L
Compound produced in Example 7: 0.34 nmol/L
Compound produced in Example 7(1): 0.26 nmol/L According to the present evaluation system, octreotide, for example, had EC50 of 0.24 nmol/L, the compound represented by the following formula (M):

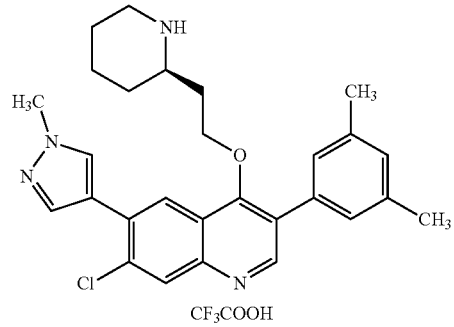

disclosed in WO 2008/051272 had EC50 of 0.06 nmol/L.

Meanwhile the compound disclosed in PTL 3 did not shown any SSTR2 agonistic activity in the present evaluation system even at the concentration of 10 μM.

Biological Example 2

Evaluation of Suppression of Growth Hormone (GH) Secretion Using Rats

[Procedure (A): Administration of a Test Compound 30 Minutes Beforehand]

A medium (distilled water (Otsuka distilled water, Otsuka Pharmaceutical Factory, Inc.)) or a test compound dissolved in the medium was orally administered to rats (7-week old male Crl:CD(SD) IGS rats (Charles River Laboratories Japan, Inc.)) and after 27 minutes, the animals were administered with 50 mg/kg of pentobarbital sodium (Somnopentyl, Kyoritsu Seiyaku Corporation) via the tail vein for anaesthesia. Three minutes after administration of pentobarbital sodium, the rats were administered with 0.01 mg/kg of growth hormone-releasing hormone (GHRH, Bachem) via the tail vein to induce GH secretion. In order to measure the blood GH concentration, 0.2 mL of blood was collected through the jugular vein at 5 minutes after administration of GHRH. The collected blood was centrifuged at 4° C., 13,000×g for 5 minutes to obtain plasma. The blood GH concentration was measured by using Rat/Mouse Growth Hormone ELISA (Millipore) following the instruction of the kit. The percentage (%) of suppression of GH secretion was determined by using the obtained blood GH concentration and the equation {[suppression (%) of GH secretion]= ([blood GH concentration of the group administered with the medium]−[blood GH concentration of the group administered with a test compound])/[blood GH concentration of the group administered with the medium]×100}. In the equation, the group administered with the medium represents the group of animals administered with the medium and the group administered with a test compound represents the group of animals administered with a test compound dissolved in the medium.

[Procedure (B): Administration of a Test Compound 8 Hours Beforehand]

A medium (distilled water (Otsuka distilled water, Otsuka Pharmaceutical Factory, Inc.)) or a test compound dissolved in the medium was orally administered to rats (7-week old male Crl:CD(SD) IGS rats (Charles River Laboratories Japan, Inc.)) and after 7 hours and 57 minutes, the animals were administered with 50 mg/kg of pentobarbital sodium (Somnopentyl, Kyoritsu Seiyaku Corporation) via the tail vein for anaesthesia. Three minutes after administration of pentobarbital sodium, the rats were administered with 0.01 mg/kg of growth hormone-releasing hormone (GHRH, Bachem) via the tail vein to induce GH secretion. The rest of the procedure is the same as in [Procedure (A)] described above.

[Results]

The present compounds exhibited strong suppression of GH secretion. The compounds and the percentage of suppression (procedure; dosage) are correlated as follows.
Compound produced in Example 1: 93% (Procedure (B); 1 mg/kg)
Compound produced in Example 2: 93% (Procedure (B); 1 mg/kg)
Compound produced in Example 2(1): 91% (Procedure (B); 1 mg/kg)
Compound produced in Example 2(2): 93% (Procedure (B); 1 mg/kg)
Compound produced in Example 2(3): 88% (Procedure (B); 1 mg/kg)
Compound produced in Example 2(4): 88% (Procedure (B); 1 mg/kg)
Compound produced in Example 2(5): 85% (Procedure (B); 1 mg/kg)
Compound produced in Example 3: 88% (Procedure (B); 1 mg/kg)
Compound produced in Example 3(1): 86% (Procedure (B); 1 mg/kg)
Compound produced in Example 3(2): 84% (Procedure (B); 1 mg/kg)
Compound produced in Example 4: 84% (Procedure (B); 1 mg/kg)
Compound produced in Example 4(1): 84% (Procedure (B); 1 mg/kg)
Compound produced in Example 5: 90% (Procedure (B); 1 mg/kg)
Compound produced in Example 5(1): 90% (Procedure (B); 1 mg/kg)
Compound produced in Example 5(2): 90% (Procedure (B); 1 mg/kg)
Compound produced in Example 5(3): 96% (Procedure (B); 1 mg/kg)
Compound produced in Example 5(4): 89% (Procedure (B); 1 mg/kg)
Compound produced in Example 5(5): 85% (Procedure (B); 1 mg/kg)
Compound produced in Example 5(6): 89% (Procedure (B); 1 mg/kg)
Compound produced in Example 6: 89% (Procedure (B); 1 mg/kg)
Compound produced in Example 7: 93% (Procedure (B); 10 mg/kg)
Compound produced in Example 7(1): 88% (Procedure (B); 3 mg/kg)

According to the present evaluation system, octreotide, for example, showed the suppression of GH secretion of 98% (Procedure (A)) at a dosage of 0.003 mg/kg (by subcutaneous administration).

Biological Example 3

Evaluation of Cytotoxicity Using Cultured Human Hepatocytes

[Procedures]

Frozen adhesive human hepatocytes were thawed, suspended in a hepatocellular medium (HCM) purchased from Lonza and inoculated to a 96-well plate coated with collagen. The culture medium of the hepatocytes cultured overnight in an incubator (5% carbon dioxide, 95% air, 37° C.) was exchanged to the medium containing a test compound at a concentration of 0, 12.5, 25, 50, 100, 200 or 400 ($\times 10^{-6}$ mol/L) and the cells were further cultured for 24 hours. Cytotoxicity was evaluated by measuring the intracellular ATP concentration. Specifically, using the Promega Celltiter-Glo luminescent assay kit available from Promega, cells were lysed in the assay buffer included in the kit and the concentration of ATP released from the cells was measured according to the luminescence resulting from luciferin-luciferase enzyme activity. The luminescence was measured on the SpectraMax plate reader from Molecular Devices. The extent of cytotoxicity of a test compound is represented by the concentration (IC50) of the compound at which 50% of the luminescence is suppressed.

[Results]

The present compounds had low toxicity on cultured human hepatocytes. The compounds and IC50 values are correlated as follows.
Compound produced in Example 1: 0.019 mmol/L
Compound produced in Example 2: 0.010 mmol/L
Compound produced in Example 2(1): 0.019 mmol/L
Compound produced in Example 2(2): 0.011 mmol/L
Compound produced in Example 2(3): 0.009 mmol/L
Compound produced in Example 2(4): 0.013 mmol/L
Compound produced in Example 2(5): 0.019 mmol/L
Compound produced in Example 3: 0.036 mmol/L
Compound produced in Example 3(1): 0.019 mmol/L
Compound produced in Example 3(2): 0.017 mmol/L
Compound produced in Example 4: 0.017 mmol/L
Compound produced in Example 4(1): Not tested
Compound produced in Example 5: 0.018 mmol/L
Compound produced in Example 5(1): 0.018 mmol/L
Compound produced in Example 5(2): 0.022 mmol/L
Compound produced in Example 5(3): 0.010 mmol/L
Compound produced in Example 5(4): 0.017 mmol/L
Compound produced in Example 5(5): 0.017 mmol/L
Compound produced in Example 5(6): 0.018 mmol/L
Compound produced in Example 7: 0.074 mmol/L
Compound produced in Example 7(1): 0.034 mmol/L According to the present evaluation system, the compound represented by the formula (M) showed IC50 of 0.013 mmol/L. On the basis of the values of the SSTR2 agonistic activity obtained in Biological Example 1 and the results of cytotoxicity obtained in Biological Example 3, it is found that the present compounds have excellent divergence between the activity and the toxicity.

Biological Example 4

Human Hepatic Microsome Stability Test

[Procedures]

To a reaction vessel heated to 37° C. in a water bath, 0.392 mL of phosphate buffer (0.1 mol/L, pH 7.4) containing human hepatic microsomes (1 mg/mL, Xenotech) and NADPH-Co-factor (NADP+1.3 mmol/L, BD-Bioscience) was added and pre-incubated for 5 minutes. A 50% acetonitrile solution (0.008 mL) containing 0.05 mmol/L of a test compound was added thereto to initiate the enzyme reaction (final concentration of the test compound: 0.001 mmol/L). Immediately after initiation of the reaction and at 60 minutes thereafter, 0.050 mL of the reaction solution was respectively collected, which was immediately added to an acetonitrile solution (0.2 mL) containing an internal standard (45 nmol/L, 1-[3-(3,5-dimethylphenyl)-4-quinolinyl]-4-piperidineamine) to terminate the enzyme reaction.

The residual rate (%), which is indicative of stability of the test compound, was calculated using the ratio of peak areas between the test compound and the internal substance determined by LC/MS/MS (TSQ Quantum Discovery MAX, Thermo) analysis of the sample thus prepared by the above procedures followed by filtration, and the equation: {[residual rate (%)=[peak area of a test compound in a sample at 60 minutes after initiation of the reaction/peak area of the internal standard]/[peak area of the test compound in the sample immediately after initiation of the reaction/peak area of the internal standard]×100}.

[Results]

The present compounds were stable in the human hepatic microsome stability test. The compounds and the residual rates are correlated as follows.
Compound produced in Example 1: 94.6(%)
Compound produced in Example 2: 88.0(%)
Compound produced in Example 2(1): 100.0(%)
Compound produced in Example 2(2): 100.0(%)
Compound produced in Example 2(3): 96.4(%)
Compound produced in Example 2(4): 94.0(%)
Compound produced in Example 2(5): 53.1(%)
Compound produced in Example 3: 85.2(%)
Compound produced in Example 3(1): 50.3(%)
Compound produced in Example 3(2): 48.4(%)
Compound produced in Example 4: 100.0(%)
Compound produced in Example 4(1): 49.9(%)
Compound produced in Example 5: 79.7(%)
Compound produced in Example 5(1): 57.6(%)
Compound produced in Example 5(2): 80.3(%)
Compound produced in Example 5(3): 67.7(%)
Compound produced in Example 5(4): 74.9(%)
Compound produced in Example 5(5): 88.6(%)
Compound produced in Example 5(6): 83.9(%)
Compound produced in Example 6: 89.9(%)
Compound produced in Example 7: 100.0(%)
Compound produced in Example 7(1): 92.9(%)

According to the present evaluation system, the compound represented by the following formula (P):

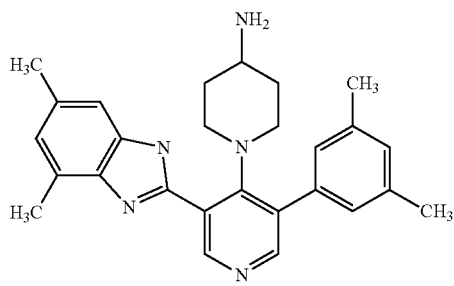

(P)

disclosed in Example 21(1) of International Patent Application No. PCT/JP2013/068084 had a residual rate of 1.2%.

Formulation Example 1

Tablets Containing 5 mg of 1-{3-(3,5-dichlorophenyl)-5-[4-(trifluoromethyl)phenyl]-4-pyridinyl}-4-piperidineamine The following components were mixed and compressed to tablets according to standard methods to obtain 10,000 tablets each containing 5 mg of the active component.

1-{3-(3,5-Dichlorophenyl)-5-[4-(trifluoromethyl)phenyl]-4-pyridinyl}-4-piperidineamine: 50 g Carboxymethylcellulose calcium (disintegrating agent): 20 g Magnesium stearate (lubricant): 10 g Microcrystalline cellulose: 920 g Formulation Example 2

Injections Containing 20 mg of 1-{3-(3,5-dichlorophenyl)-5-[4-(trifluoromethyl)phenyl]-4-pyridinyl}-4-piperidineamine The following components were mixed according to the standard method, and the solution was then sterilised according to the standard method, divided into ampoules at 5-mL aliquot and lyophilised according to the standard method to obtain 10,000 ampoules each containing 20 mg of the active component.

1-{3-(3,5-Dichlorophenyl)-5-[4-(trifluoromethyl)phenyl]-4-pyridinyl}-4-piperidineamine: 200 g Mannitol: 20 g Distilled water: 50 L

INDUSTRIAL APPLICABILITY

The present compound has strong agonistic activity for a somatostatin receptor, particularly for somatostatin receptor subtype 2, and thus is useful as a prophylactic and/or therapeutic agent for various diseases in which somatostatin per se or a hormone modulated by somatostatin is involved, particularly acromegaly and gastrointestinal symptoms accompanying gastrointestinal obstruction.

The invention claimed is:

1. A compound represented by the general formula (I):

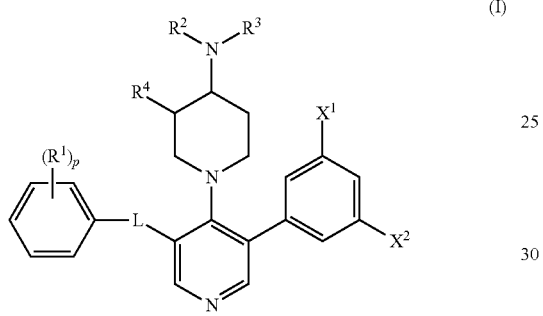

wherein R¹ represents (1) a halogen atom, (2) a cyano group, (3) a C1-4 alkyl, (4) a C1-4 alkoxy or (5) a C3-8 cycloalkyl, wherein the C1-4 alkyl, the C1-4 alkoxy and the C3-8 cycloalkyl may be respectively and independently substituted with 1 to 3 halogen atoms and/or cyano groups; p represents an integer of 0 to 2; when p is 2, a plurality of R¹ may be the same or different; R² and R³ respectively and independently represent a hydrogen atom or a C1-4 alkyl; R⁴ represents a hydrogen atom; or R² and R⁴ together with an atom to which the R² and R⁴ are attached may form a 5- to 8-membered nitrogen-containing saturated heterocycle; L represents (1) a bond, (2) —CR$^A$=CR$^B$→ or (3) —C(=O)—NR$^D$→ (wherein in each group, the arrow indicates the site of binding to the pyridine ring); R$^A$, R$^B$ and R$^D$ respectively and independently represent a hydrogen atom or a C1-4 alkyl; X¹ and X² respectively and independently represent a halogen atom;

a salt thereof, an N-oxide thereof or a solvate thereof, or a prodrug of the foregoing.

2. The compound according to claim 1, represented by the general formula (I-1):

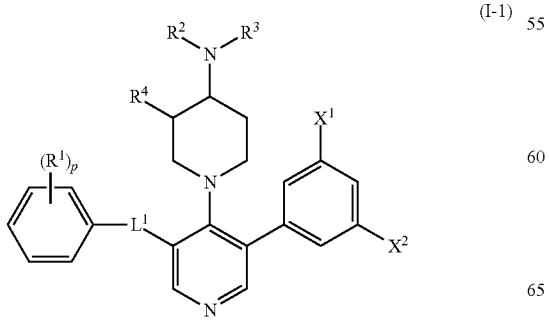

wherein L¹ represents (1) —CR$^A$=CR$^B$→ or (2) —C(=O)—NR$^D$→ (wherein in each group, the arrow indicates the site of binding to the pyridine ring); and other symbols have the same meanings as described in claim 1, a salt thereof, an N-oxide thereof or a solvate thereof, or a prodrug of the foregoing.

3. The compound according to claim 1, represented by the general formula (I-4):

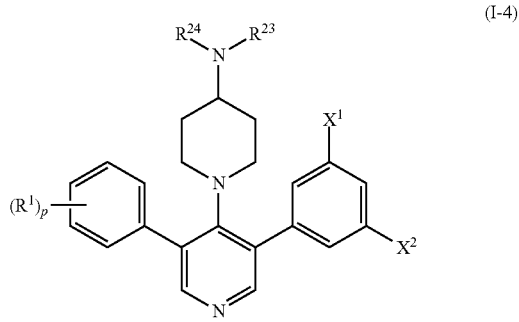

wherein R²⁴ represents a hydrogen atom or a C1-4 alkyl; and other symbols have the same meanings as described in claim 1, a salt thereof, an N-oxide thereof or a solvate thereof, or a prodrug of the foregoing.

4. The compound according to claim 1, which is selected from the group consisting of the following compounds:

(1) N-[4-(4-amino-1-piperidinyl)-5-(3-chloro-5-fluorophenyl)-3-pyridinyl]-3-chlorobenzamide;

(2) 1-{3-(3-chloro-5-fluorophenyl)-5-[(E)-2-(3-chlorophenyl)vinyl]-4-pyridinyl}-4-piperidineamine;

(3) 3-{(E)-2-[4-(4-amino-1-piperidinyl)-5-(3,5-dichlorophenyl)-3-pyridinyl]vinyl}benzonitrile;

(4) (4aS,8aS)-6-{3-(3,5-dichlorophenyl)-5-[(E)-2-(3-fluorophenyl)vinyl]-4-pyridinyl}octahydro-1H-pyrido[3,4-b][1,4]oxazine;

(5) 1-{3-(3,5-dichlorophenyl)-5-[(1E)-2-(3-fluorophenyl)-1-propen-1-yl]-4-pyridinyl}-4-piperidineamine;

(6) 3-[(E)-2-{5-(3,5-dichlorophenyl)-4-[4-(ethylamino)-1-piperidinyl]-3-pyridinyl}vinyl]benzonitrile;

(7) 1-{3-(3,5-dichlorophenyl)-5-[(1E)-2-(3-fluorophenyl)-1-propen-1-yl]-4-pyridinyl}-N-ethyl-4-piperidineamine;
(8) 3-{(1E)-1-[4-(4-amino-1-piperidinyl)-5-(3,5-dichlorophenyl)-3-pyridinyl]-1-propen-2-yl}benzonitrile;
(9) 3-[(1E)-1-{5-(3,5-dichlorophenyl)-4-[4-(ethylamino)-1-piperidinyl]-3-pyridinyl}-1-propen-2-yl]benzonitrile;
(10) N-[4-(4-amino-1-piperidinyl)-5-(3,5-dichlorophenyl)-3-pyridinyl]-5-fluoro-2-methoxybenzamide;
(11) 1-(4-{5-(3,5-dichlorophenyl)-4-[(4aS,8aS)-octahydro-6H-pyrido[3,4-b][1,4]oxazin-6-yl]-3-pyridinyl}phenyl)cyclopropanecarbonitrile;
(12) 1-{3-(3-chloro-5-fluorophenyl)-5-[4-(trifluoromethyl)phenyl]-4-pyridinyl}-4-piperidineamine;
(13) 1-{3-(3,5-dichlorophenyl)-5-[4-(trifluoromethyl)phenyl]-4-pyridinyl}-4-piperidineamine;
(14) 1-{3-(3-chloro-5-fluorophenyl)-5-[4-(difluoromethoxy)phenyl]-4-pyridinyl}-4-piperidineamine;
(15) 1-{4-[4-(4-amino-1-piperidinyl)-5-(3,5-dichlorophenyl)-3-pyridinyl]phenyl}cyclopropanecarbonitrile;
(16) 1-{3-(3,5-dichlorophenyl)-5-[4-(difluoromethoxy)phenyl]-4-pyridinyl}-4-piperidineamine;
(17) 1-(4-{5-(3,5-dichlorophenyl)-4-[4-(ethylamino)-1-piperidinyl]-3-pyridinyl}phenyl)cyclopropanecarbonitrile;
(18) 2-{4-[4-(4-amino-1-piperidinyl)-5-(3,5-dichlorophenyl)-3-pyridinyl]phenyl}-2-methylpropanenitrile;
(19) 2-(4-{5-(3,5-dichlorophenyl)-4-[4-(ethylamino)-1-piperidinyl]-3-pyridinyl}phenyl)-2-methylpropanenitrile;
(20) 1-{3-(3,5-dichlorophenyl)-5-[4-(trifluoromethyl)phenyl]-4-pyridinyl}-N-ethyl-4-piperidineamine; and
(21) 1-{3-(3,5-dichlorophenyl)-5-[4-(difluoromethoxy)phenyl]-4-pyridinyl}-N-ethyl-4-piperidineamine,
a salt thereof, an N-oxide thereof or a solvate thereof, or a prodrug of the foregoing.

5. The compound according to claim 2, which is selected from the group consisting of the following compounds:
(1) N-[4-(4-amino-1-piperidinyl)-5-(3-chloro-5-fluorophenyl)-3-pyridinyl]-3-chlorobenzamide;
(2) 1-{3-(3-chloro-5-fluorophenyl)-5-[(E)-2-(3-chlorophenyl)vinyl]-4-pyridinyl}-4-piperidineamine;
(3) 3-{(E)-2-[4-(4-amino-1-piperidinyl)-5-(3,5-dichlorophenyl)-3-pyridinyl]vinyl}benzonitrile;
(4) (4aS,8aS)-6-{3-(3,5-dichlorophenyl)-5-[(E)-2-(3-fluorophenyl)vinyl]-4-pyridinyl}octahydro-1H-pyrido[3,4-b][1,4]oxazine;
(5) 1-{3-(3,5-dichlorophenyl)-5-[(1E)-2-(3-fluorophenyl)-1-propen-1-yl]-4-pyridinyl}-4-piperidineamine;
(6) 3-[(E)-2-{5-(3,5-dichlorophenyl)-4-[4-(ethylamino)-1-piperidinyl]-3-pyridinyl}vinyl]benzonitrile;
(7) 1-{3-(3,5-dichlorophenyl)-5-[(1E)-2-(3-fluorophenyl)-1-propen-1-yl]-4-pyridinyl}-N-ethyl-4-piperidineamine;
(8) 3-{(1E)-1-[4-(4-amino-1-piperidinyl)-5-(3,5-dichlorophenyl)-3-pyridinyl]-1-propen-2-yl}benzonitrile;
(9) 3-[(1E)-1-{5-(3,5-dichlorophenyl)-4-[4-(ethylamino)-1-piperidinyl]-3-pyridinyl}-1-propen-2-yl]benzonitrile; and
(10) N-[4-(4-amino-1-piperidinyl)-5-(3,5-dichlorophenyl)-3-pyridinyl]-5-fluoro-2-methoxybenzamide,
a salt thereof, an N-oxide thereof or a solvate thereof, or a prodrug of the foregoing.

6. The compound according to claim 3, which is selected from the group consisting of the following compounds:
(1) 1-{3-(3-chloro-5-fluorophenyl)-5-[4-(trifluoromethyl)phenyl]-4-pyridinyl}-4-piperidineamine;
(2) 1-{3-(3,5-dichlorophenyl)-5-[4-(trifluoromethyl)phenyl]-4-pyridinyl}-4-piperidineamine;
(3) 1-{3-(3-chloro-5-fluorophenyl)-5-[4-(difluoromethoxy)phenyl]-4-pyridinyl}-4-piperidineamine;
(4) 1-{4-[4-(4-amino-1-piperidinyl)-5-(3,5-dichlorophenyl)-3-pyridinyl]phenyl}cyclopropanecarbonitrile;
(5) 1-{3-(3,5-dichlorophenyl)-5-[4-(difluoromethoxy)phenyl]-4-pyridinyl}-4-piperidineamine;
(6) 1-(4-{5-(3,5-dichlorophenyl)-4-[4-(ethylamino)-1-piperidinyl]-3-pyridinyl}phenyl)cyclopropanecarbonitrile;
(7) 2-{4-[4-(4-amino-1-piperidinyl)-5-(3,5-dichlorophenyl)-3-pyridinyl]phenyl}-2-methylpropanenitrile;
(8) 2-(4-{5-(3,5-dichlorophenyl)-4-[4-(ethylamino)-1-piperidinyl]-3-pyridinyl}phenyl)-2-methylpropanenitrile;
(9) 1-{3-(3,5-dichlorophenyl)-5-[4-(trifluoromethyl)phenyl]-4-pyridinyl}-N-ethyl-4-piperidineamine; and
(10) 1-{3-(3,5-dichlorophenyl)-5-[4-(difluoromethoxy)phenyl]-4-pyridinyl}-N-ethyl-4-piperidineamine,
a salt thereof, an N-oxide thereof or a solvate thereof, or a prodrug of the foregoing.

7. A pharmaceutical composition comprising the compound according to claim 1, a salt thereof, an N-oxide thereof or a solvate thereof, or a prodrug of the foregoing and a pharmaceutically acceptable carrier.

8. The pharmaceutical composition according to claim 7, which is a therapeutic agent for acromegaly, or a therapeutic agent for a gastrointestinal symptom accompanying gastrointestinal obstruction.

9. A medicament comprising the compound according to claim 1, a salt thereof, an N-oxide thereof or a solvate thereof, or a prodrug of the foregoing in combination with at least one drug selected from the group consisting of pegvisomant, bromocriptine and cabergoline.

10. A medicament comprising the compound according to claim 1, a salt thereof, an N-oxide thereof or a solvate thereof, or a prodrug of the foregoing in combination with at least one drug selected from the group consisting of prochlorperazine, levomepromazine, risperidone, metoclopramide, domperidone, diphenhydramine, chlorpheniramine, dimenhydrinate, promethazine, diprophylline, famotidine, cimetidine, scopolamine, tropisetron, granisetron, ondansetron, azasetron, ramosetron, indisetron, palonosetron, cisapride, mosapride, dexamethasone, betamethasone, prednisolone, olanzapine, quetiapine, perospirone, methylnaltrexone and morphine.

11. A method for therapy of acromegaly or a gastrointestinal symptom accompanying gastrointestinal obstruction, comprising administering to a mammal an effective amount of the compound according to claim 1, a salt thereof, an N-oxide thereof or a solvate thereof, or a prodrug of the foregoing.

12. A method for treating acromegaly, comprising administering to a mammal an effective amount of the compound according to claim 1, a salt thereof, an N-oxide thereof or a solvate thereof, or a prodrug of the foregoing in combination with at least one drug selected from the group consisting of pegvisomant, bromocriptine and cabergoline.

13. A method for treating a gastrointestinal symptom accompanying gastrointestinal obstruction, comprising administering to a mammal an effective amount of the compound according to claim 1, a salt thereof, an N-oxide thereof or a solvate thereof, or a prodrug of the foregoing in combination with at least one drug selected from the group consisting of prochlorperazine, levomepromazine, risperidone, metoclopramide, domperidone, diphenhydramine, chlorpheniramine, dimenhydrinate, promethazine, diprophylline, famotidine, cimetidine, scopolamine, tropisetron, granisetron, ondansetron, azasetron, ramosetron, indisetron, palonosetron, cisapride, mosapride, dexamethasone, betamethasone, prednisolone, olanzapine, quetiapine, perospirone, methylnaltrexone and morphine.

* * * * *